(12) United States Patent
Korte et al.

(10) Patent No.: US 7,122,715 B2
(45) Date of Patent: Oct. 17, 2006

(54) IN VITRO METHOD TO CREATE CIRCULAR MOLECULES FOR USE IN TRANSFORMATION

(75) Inventors: John A. Korte, Westerly, RI (US); Brenda A. Lowe, Mystic, CT (US)

(73) Assignee: Monsanto Technology LLC, St. Louis, MO (US)

( * ) Notice: Subject to any disclaimer, the term of this patent is extended or adjusted under 35 U.S.C. 154(b) by 750 days.

(21) Appl. No.: 09/957,660

(22) Filed: Sep. 20, 2001

(65) Prior Publication Data

US 2003/0100077 A1  May 29, 2003

(51) Int. Cl.
  *C12N 15/10* (2006.01)
  *C12N 15/82* (2006.01)
  *C12N 15/87* (2006.01)
  *C12N 15/33* (2006.01)

(52) U.S. Cl. ............ 800/278; 800/260; 800/279; 800/292; 800/293; 800/300; 800/312; 800/320.1; 800/288; 435/91.2; 435/462; 435/468; 435/470

(58) Field of Classification Search .......... 435/91.2, 435/320.1, 462
See application file for complete search history.

(56) References Cited

U.S. PATENT DOCUMENTS

| 5,658,772 | A |   | 8/1997  | Odell et al.   | 435/172.3 |
|-----------|---|---|---------|----------------|-----------|
| 5,756,708 | A | * | 5/1998  | Karan et al.   | 536/23.1  |
| 5,854,033 | A | * | 12/1998 | Lizardi        | 435/91.2  |
| 5,861,273 | A | * | 1/1999  | Olson et al.   | 435/69.1  |
| 6,040,497 | A |   | 3/2000  | Spencer et al. | 800/288   |
| 6,153,811 | A |   | 11/2000 | Lowe et al.    | 800/278   |
| 6,620,597 | B1|   | 9/2003  | Chen et al.    |           |
| 6,858,412 | B1| * | 2/2005  | Willis et al.  | 435/91.1  |

FOREIGN PATENT DOCUMENTS

WO  WO 99/35281  *  7/1999

OTHER PUBLICATIONS

Wang et al. Somatic Cell and Molecular Genetics 21(6): 429-441 (1995).*
Hasan et al. Gene 150(1): 51-56 (1994).*
van Mellaert et al. Microbiology 144(12): 3351-3358 (1998).*
Won et al. Yonsei Medical Journal 42(2): 204-208 (2001).*
Wang et al. Molecular Vision 7: 89-94 (2001).*
Schroeter et al. Journal of Clinical Microbiology 39 (2): 765-768 (2001).*
Bidle et al. Journal of Bacteriology 183(5): 1688-1693 (2001).*
Albert et al., "Site-specific integration of DNA into wild-type and mutant lox sites placed in the plant genome," *Plant J.*, 7(4):649-659, 1995.
Ausubel et al., Current Protocols in Molecular Biology, pub. John Wiley & Sons, Inc., 1987, including updates to Winter 2001, Table of Contents only.
Futcher, "The μm circle plasmid of Saccharomyces cerevisiae," *Yeast*, 4:27-40, 1988.
Gietz and Woods, "Genetic transformation of yeast," *BioTechniques*, 30:816-831, 2001.
Golic and Lindquist, "The FLP recombinase of yeast catalyzes site-specific recombination in the drosophila genome," *Cell*, 59:499-509, 1989.
Lindberg and Andersson, "Purification of full-length enterovirus cDNA by solid phase hybridization capture facilitates amplification of complete geonmes," *J. Virological Meth.*, 77(2):131-137, 1999.
Ohler and Rose, "Optimization of long-distance PCR using a transposon-based model system," *PCR Methods and Applications*, 2:51-59, 1992.
Ow, "Recombinase-directed chromosome engineering in plants," *Curr. Op. Biotech.*, 7:181-186, 1996.
Sambrook and Russell in *Molecular Cloning: A Laboratory Manual*, Third Edition, Cold Spring Harbor Laboratory, Cold Spring Harbor, New York, 2001, Table of Contents only.
Sternberg et al., "Bacteriophage P1 *cre* gene and its regulatory region. Evidence for multiple promoters and for regulation by DNA methylation," *J. Mol. Biol.*, 187:197-212, 1986.

* cited by examiner

*Primary Examiner*—David T. Fox
(74) *Attorney, Agent, or Firm*—Fulbright & Jaworski LLP.

(57) ABSTRACT

The present invention relates generally to transgenic plants. More specifically, it relates to methods and compositions for the introduction of DNA using circular molecules that are not able to replicate outside a host cell. The circular molecules contain site-specific recombination sequences and allow transformation of host cells with DNA comprising only selected sequences of interest.

45 Claims, 11 Drawing Sheets

IN VITRO METHOD TO CREATE CIRCULAR MOLECULES FOR USE IN TRANSFORMATION

BACKGROUND OF THE INVENTION

1. Field of the Invention

The present invention relates generally to transgenic plants. More specifically, it relates to methods and compositions for the introduction of DNA using circular molecules that are not able to replicate outside a host cell genome.

2. General Description of the Related Art

The production of genetically modified organisms involves the introduction of DNA sequences into, or in addition to, the existing genome of a recipient cell, tissue or organism. This transformation of new genetic material has been reported for a wide variety of organisms including, but not limited to, yeast, bacteria, mammals, plants, viruses and insects. In each case, specialized vectors are required for the proper insertion, maintenance or expression of the introduced DNA.

DNA used for transformation can be either double- or single-stranded, and can be circular or linear in form. In a laboratory, DNA is commonly used for transformation in its double-stranded (ds) form, although DNA in single-stranded form (ssDNA) has been used to transform yeast (see Gietz and Woods, 2001). In nature, single-stranded (ss) DNA intermediates are involved during transformation by *Agrobacterium tumefaciens* and some viruses. Circular, double-stranded DNA (dsDNA) is the most commonly used conformation for transformation (Sambrook and Russell, 2001; Ausubel et al., 2001) although linear ds-DNA may be used as well, for example, for transformation of yeast (Raymond et al., 1999) or microprojectile bombardment of plant cells (see, for example, U.S. Pat. Nos. 6,153,811 and 6,0404,97). Generation of transformable DNA requires that one of ordinary skill in the art perform several operations including, but not limited to, ligation of the proper DNA pieces needed for maintenance of the vector and expression of the desired genes, passage of the completed vector through the proper host cells to increase the number of molecules, purification of the vector in the desired form for transformation and, if using linear DNA molecules, preparation and purification of the linear fragment from a circular molecule or other starting nucleic acid source.

Currently, circular dsDNA molecules are propagated by passage through a bacterial host and typically contain bacterial origins of replication or other associated sequences. It is often undesirable to have "ancillary sequences," such as bacterial origins of replication, in the transformed organism. It would be advantageous to have a means of producing circular DNA molecules that do not contain ancillary sequences, such as origins of replication, in ample numbers for transformation. Circular molecules without ancillary sequences would not require removal of these ancillary sequences in the target host or removal prior to the transformation of the host.

There is a need to simplify the preparation of circular, dsDNA molecules for transformation without the need for ancillary sequences usually associated with maintenance of exogenous sequences in cells typically used for vector production. Furthermore, a method is needed to produce sufficient quantities of circular DNAs for use in direct DNA delivery transformation methods.

SUMMARY OF THE INVENTION

In one aspect, the present invention provides a means for making a non-replicating circular nucleic acid molecule that is useful for transformation. A first circular molecule, or circular template, is generated by joining selected DNA sequences in a desired order in a circular molecule. A plurality of second circular DNA molecules, or transformation-ready circular molecules, is generated in vitro using a polymerase chain reaction amplification method. The second circular molecules, that is, the transformation-ready circular molecules, are substantially identical to the first circular molecule, e.g., the circular template. The oligonucleotide primers used in the polymerase chain reaction (PCR) amplification are non-mutagenizing. A first non-mutagenizing primer is complementary to a selected region of the circular template substrate molecule. A second non-mutagenizing primer is complementary to the first non-mutagenizing primer.

In another aspect, the invention provides an isolated, non-replicating, circular nucleic acid molecule comprising a selected sequence wherein the circular molecule is substantially identical to a substrate molecule. The transformation-ready circular molecule comprises select sequences and does not contain ancillary sequences such as bacterial origins of replication and the like. The circular template and the plurality of transformation-ready circular molecules comprise a site-specific recombination sequence. The site-specific recombination sequence is preferably selected from the group consisting of lox, frt, RS and gix sites, more preferably the recombination sequence is a lox site, and most preferably, the lox sequence is selected from the group consisting of SEQ ID NO:1, SEQ ID NO:2, SEQ ID NO:3 and SEQ ID NO:4. The site-specific recombination sequence is recognized by a recombinase enzyme, preferably selected from the group consisting of CRE, FLP, Gin and R recombinase and more preferably, the enzyme recognizing the site-specific recombination sequence is CRE recombinase.

In yet another aspect, the present invention provides a means of making a transgenic cell comprising the steps of a) providing a non-replicating circular nucleic acid molecule; b) contacting a host cell with the non-replicating circular nucleic acid molecule under conditions wherein the cell acquires the circular nucleic acid molecule; and c) identifying a transgenic cell comprising a transgenic nucleic acid sequence of the circular nucleic acid molecule. The target host cell may be contacted with the non-replicating circular nucleic acid molecule by a variety of means such as PEG mediated transformation of protoplasts, electroporation, or silicon carbide fiber mediated transformation and preferably, microprojectile bombardment. The genome of the target host cell comprises a first site-specific recombination sequence, preferably selected from the group consisting of lox, gix, RS and frt sites, more preferably the site-specific recombination site is a lox site and most preferably, the lox sequence is selected from the group consisting of SEQ ID NO:1, SEQ ID NO:2, SEQ ID NO:3 and SEQ ID NO:4.

The host cell to be transformed with the transformation-ready circular DNA molecule of the invention may be derived from a plant, animal, fungus, virus or bacteria. In one embodiment, the cell is derived from a plant, and preferably is a dicotyledenous plant cell, even more preferably selected from the group consisting of tobacco, tomato, potato, soybean, cotton, canola, alfalfa and sunflower, and most preferably, soybean. In a preferred embodiment, the cell is derived from a plant, and preferably is a monocotyledenous plant cell, even more preferably selected from the group consisting of wheat, maize, rye, rice, oat, barley, turfgrass, sorghum, millet and sugarcane and most preferably, maize. A plant cell or plant may be haploid, diploid or polyploid.

The select sequences to be introduced into the host cell with the transformation-ready circular molecules may comprise any desired sequence. In one embodiment, the select sequence comprises sequences encoding a protein imparting insect resistance, bacterial disease resistance, fungal disease resistance, viral disease resistance, nematode disease resistance, herbicide resistance, enhanced grain composition or quality, enhanced nutrient utilization, enhanced environment or stress resistance, reduced mycotoxin contamination, male sterility, a selectable marker phenotype, a screenable marker phenotype, a negative selectable marker phenotype, or altered plant agronomic characteristics. Where the selected sequences encode a protein imparting a selectable marker phenotype, the protein may be selected from the group consisting of phosphinothricin acetyltransferase, glyphosate resistant EPSPS, aminoglycoside phosphotransferase, hygromycin phosphotransferase, neomycin phosphotransferase, dalapon dehalogenase, bromoxynil resistant nitrilase, anthranilate synthase and glyphosate oxidoreductase.

The selected DNA sequences may further comprise additional sequences. The selected coding region may be operably linked to a promoter sequence, for example, a 35S or rice actin promoter. The selected coding region may be operably linked to a 3' untranslated region, for example, a nos 3' UTR. Benefit may also be realized by including an enhancer with the selected DNA. Examples of such an enhancer include the rice actin 1 intron 1 and rice actin 2 intron 1. The selected DNA may also comprise a sequence encoding a signal peptide. Examples of signal peptides that could be used include a peroxisomal targeting peptide or a chloroplast transit peptide. Examples of a chloroplast transit peptide include the group consisting of chlorophyll a/b binding protein transit peptide, small subunit of ribulose bisphosphate carboxylase transit peptide, EPSPS transit peptide and dihydrodipocolinic acid synthase transit peptide.

In yet another aspect, the present invention provides a transgenic plant comprising a selected DNA prepared in accordance with the invention. The transgenic plant may be potentially any type of plant, including a monocotyledonous or dicotyledonous plant. Examples of monocotyledonous plants include wheat, maize, rye, rice, oat, barley, turfgrass, sorghum, millet and sugarcane. In one embodiment of the invention, the monocotyledonous plant is maize. Examples of dicotyledonous plants include tobacco, tomato, potato, soybean, cotton, canola, alfalfa, sunflower, and cotton. In another embodiment of the invention, the dicotyledonous plant is a soybean plant.

The transgenic plant may comprise any selected DNA sequence. In one embodiment, the selected sequences may encode a protein imparting insect resistance, bacterial disease resistance, fungal disease resistance, viral disease resistance, nematode disease resistance, herbicide resistance, enhanced grain composition or quality, enhanced nutrient utilization, enhanced environment or stress resistance, reduced mycotoxin contamination, male sterility, a selectable marker phenotype, a screenable marker phenotype, a negative selectable marker phenotype, or altered plant agronomic characteristics. Where the selected sequences encode a protein imparting a selectable marker phenotype, the protein is selected from the group consisting of phosphinothricin acetyltransferase, glyphosate resistant EPSPS, aminoglycoside phosphotransferase, hygromycin phosphotransferase, neomycin phosphotransferase, dalapon dehalogenase, bromoxynil resistant nitrilase, anthranilate synthase and glyphosate oxidoreductase. In another embodiment, the transgenic plant comprises selected sequences comprising UIDA, NPT II or EPSPS.

The transgenic plant prepared in accordance with the invention may be of any generation, including a fertile $R_0$ transgenic plant as well as seeds thereof, wherein the seed comprises the selected DNA. Also included within the invention are progeny plants of any generation such a fertile $R_0$ transgenic plant, wherein the progeny plant comprises said selected DNA, as well as seed of a progeny plant, wherein said seed comprises said selected DNA.

In yet another aspect, the invention provides a crossed fertile transgenic plant prepared according to the method comprising the steps of: (i) obtaining a fertile transgenic plant comprising selected DNA transformed into the plant using a non-replicating, transformation-ready circular nucleic acid molecule; (ii) crossing the fertile transgenic plant with itself or with a second plant to prepare the seed of a crossed fertile transgenic plant, wherein said seed comprises said selected DNA; and (iii) planting said seed to obtain a crossed fertile transgenic plant. The second plant crossed to the first fertile transgenic plant may lack a selected DNA. The invention also includes a seed or seeds of such a crossed fertile transgenic plant, wherein said seed comprises said selected DNA.

The crossed fertile transgenic plant may be potentially any type of plant, including a monocotyledonous or dicotyledonous plant. Examples of monocotyledonous plants include wheat, maize, rye, rice, oat, barley, turfgrass, sorghum, millet and sugarcane. In one embodiment of the invention, the monocotyledonous plant is maize. Examples of dicotyledonous plants include tobacco, tomato, potato, soybean, cotton, canola, alfalfa, sunflower, and cotton. In another embodiment of the invention, the dicotyledonous plant is a soybean plant. The selected DNA may have been inherited through a parent used a male or a female at any given generation. In one embodiment of the invention, the second plant is an inbred plant. Where the second plant is an inbred, the crossed fertile transgenic plant may be a hybrid, or also inbred where it is crossed with itself.

The crossed fertile transgenic plant may comprise any selected sequence. Potentially any coding region could be used, including a selected coding region which encodes a protein selected from the group consisting of a protein imparting insect resistance, bacterial disease resistance, fungal disease resistance, viral disease resistance, nematode disease resistance, herbicide resistance, enhanced grain composition or quality, enhanced nutrient utilization, enhanced environment or stress resistance, reduced mycotoxin contamination, male sterility, a selectable marker phenotype, a screenable marker phenotype, a negative selectable marker phenotype, or altered plant agronomic characteristics. In another embodiment, the crossed fertile transgenic plant comprises selected sequences comprising UIDA, NPT II or EPSPS. The crossed fertile transgenic plant may further comprise a selected DNA comprising a promoter, for example, 35S or rice actin. The plant may further comprise a selected DNA comprising an enhancer, for example, a rice actin 1 intron 1 and rice actin 2 intron 1. The selected coding region may be operably linked to a 3' UTR, for example, a nos 3' UTR.

The invention further provides for seed or seeds of a crossed, fertile transgenic plant comprising a selected DNA sequence; for a progeny plant of any generation of a crossed fertile transgenic plant comprising the selected DNA as well as for the seed or seeds of a progeny plant wherein the seed comprises the selected DNA.

DETAILED DESCRIPTION OF THE INVENTION

Figure 1:
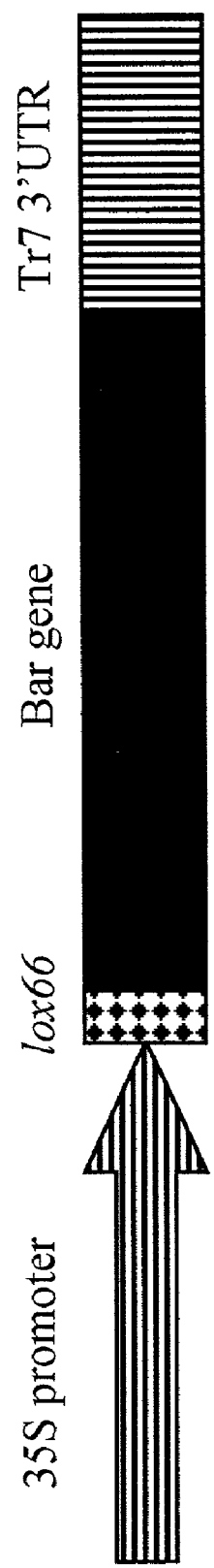
FIG. 1. Diagram of NN03 insertion site. Arrow with horizontal stripes represents a 35S promoter, rectangle with diamond shapes represents a lox66 site (SEQ ID NO:2), solid rectangle represents a bar gene, rectangle with vertical stripes represents a T7 3'UTR sequence.

The in vitro method of the present invention can be used to produce non-replicating, circular dsDNA molecules for use in transformation of host cells. The method provides a means of generating circular molecules in vitro utilizing non-mutagenizing primer pairs and amplification technology. The method overcomes deficiencies in the art as circular DNA molecules are produced which are free of ancillary sequences such as, but not limited to, origins of replication and antibiotic resistance genes, and the circular dsDNA molecule can be used directly for transformation of host cells of a variety of organisms. The present invention is particularly useful in methods of transformation that require use of a circular DNA molecule. The methods of the present invention are particularly useful for the transformation of plants, particularly transformation of plants by site-directed integration which requires a circular molecule as a substrate, and even more particularly, for the transformation of plants involving site-directed integration mediated by lox sites and CRE-recombinase.

I. Preparation of Circles of the Invention

The transformation-ready, in vitro generated dsDNA circular molecules of the invention can be synthesized from a double- or single-stranded circular template DNA containing only the selected sequences of interest. Polymerase chain reaction (PCR) is used to amplify the circular template and to generate dsDNA circular molecules for use in transformation. In brief, the starting template is heat-denatured in the presence of a set of primers. The primers are allowed to anneal to the starting template in the presence of a thermostable DNA polymerase and nucleotides, in the appropriate reaction mixture. The polymerase synthesizes a copy of the starting circular template. The reaction mixture is cycled through a series of heat denaturation, annealing and synthesis steps by which there is an exponential increase in the number of transformation-ready, dsDNA circular molecules.

The non-replicating, starting circular template for use in the PCR reaction may be generated from a variety of DNA source molecules including, but not limited to, circular double-stranded or single-stranded plasmids with or without ancillary sequences, or linear fragments of dsDNA with or without ancillary sequences, RNA or RNA which has been reverse-transcribed into complementary DNA in any of the previously described forms. One of skill in the art could use standard molecular biology techniques (see for example, Ausubel et al., 2001; Sambrook and Russell, 2001; Gelvin et al., 1990) to modify the source RNA or DNA molecules to construct the starting circular template to contain only the sequences of interest for use with the method of the invention. One of skill in the art would recognize that RNA molecules are typically reverse-transcribed into complementary DNA for use with standard molecular biology techniques. For the purposes of this discussion, DNA source molecules used in the practice of this invention may have been derived from RNA sources.

If the DNA source material is a circular dsDNA plasmid or molecule containing ancillary sequences, it is necessary to remove the ancillary sequences to generate the starting circular template. For example, restriction enzymes may be used to digest the starting circular plasmid to remove the ancillary sequences as one or more fragments of DNA while retaining the DNA sequences of interest on a single contiguous DNA fragment. The various digestion products are separated, for example on an agarose gel, and the fragment of interest isolated away from the ancillary sequences. The fragment with the sequences of interest is then self-ligated to form a starting circular template for use in generating circular molecules of the invention. One of skill in the art could also prepare a starting circular template from two or more fragments containing the DNA sequences of interest. One of ordinary skill would recognize that should the fragment or fragments contain restriction sites that are not compatible for ligation, modifications such as but not limited to, preparation of blunt ends on the fragment or the addition of linkers with compatible ends or the introduction of a desired restriction site or sites for the purpose of creating the circular template from the linear part or parts, may be necessary to allow ligation of the desired fragment or fragments. One of skill in the art could use other standard molecular biology methods to remove the ancillary sequences and reform a circular starting template for use in generating the non-replicating, transformation-ready circular nucleic acid molecules of the invention.

If the DNA source material is linear dsDNA containing ancillary sequences, it is necessary to remove the ancillary sequences and prepare starting circular template. For example, restriction enzymes may be used to digest the starting linear dsDNA to remove the ancillary sequences as one or more fragments of DNA while retaining the DNA sequences of interest in one or more DNA fragments. The various digestion products are separated, for example on an agarose gel, and the fragment or fragments of interest isolated away from the ancillary sequences. The fragment with the sequences of interest is then self-ligated to form a starting circular template for use in generating circular molecules of the invention. One of skill in the art could also prepare a starting circular template from two or more fragments containing the DNA sequences of interest. One of ordinary skill would recognize that should the fragment or fragments contain restriction sites that are not compatible for ligation, modifications such as but not limited to, preparation of blunt ends on the fragment or the addition of linkers with compatible ends or the introduction of a desired restriction site or sites for the purpose of creating the circular template from the linear part or parts, may be necessary to allow ligation of the desired fragment or fragments. One of skill in the art could use other standard molecular biology methods to remove the ancillary sequences and reform a circular starting template for use in generating the non-replicating, transformation-ready circular nucleic acid molecules of the invention.

Circular dsDNA or ssDNA templates containing only the sequences of interest, or lacking ancillary sequences, are suitable starting material for use with this invention. Linear dsDNA fragments, including those generated by PCR, lacking ancillary sequences or containing only the sequences of interest, which can be ligated or otherwise joined to form circular dsDNA templates are suitable starting material for use with this invention.

The non-replicating, transformation-ready circular molecules may contain an "expression unit" consisting of a promoter sequence operably linked to a gene of interest further linked to a 3' untranslated region (3'UTR, also known as a 3' end or simply 3'). Promoters which are useful for plant transgene expression include those that are inducible, viral, synthetic, constitutive (Paszkowski et al., 1984; Odell et al., 1985), temporally regulated, spatially regulated, and spatio-temporally regulated (Chau et al., 1989). Examples of promoter sequences that may be useful include, but are not limited to, a constitutive CaMV 35S promoter (Odell et al., 1985), an inducible glyceraldehyde-3-phosphate dehydrogenase gene promoter (Kohler et al., 1995; Quigley et al., 1989; Martinez et al., 1989) and a tissue specific corn alcohol dehydrogenase 1 promoter (Vogel et al., 1989; Dennis et al., 1984). The circular molecule may or may not contain enhancer sequences such as an intron sequence. Examples of intron sequences that may be useful include, but are not limited to, a rice actin 1 intron 1 (McElroy et al., 1990; Zhang et al., 1991) or a rice actin 2 intron 1 (PCT Publication WO 00/70067). The circular molecule may or may not contain a sequence coding for a transit peptide or other targeting signal such as a chloroplast transit peptide (U.S. Pat. Nos. 5,728,925, 5,510,471). The circular molecule may further comprise a 3'UTR, such as a nos 3'UTR (Bevan et al., 1983).

In another aspect of the invention, the non-replicating, transformation-ready circular molecule may be made to contain one, two or a greater number of "expression units" consisting of a promoter operably linked to a selected gene of interest linked to a 3'UTR sequence. An expression unit may or may not contain enhancer sequences such as an intron, or sequences encoding transit or signal peptides. An expression unit may be modified to contain a promoter operably linked to a selected gene of interest. An expression unit may be modified to contain only a promoter as the selected sequence of interest. An expression unit may be modified to contain a selected gene of interest with or without a 3'UTR sequence. One or any such modified expression units may or may not contain enhancer sequences such as an intron, a 3'UTR sequence or sequences encoding transit or signal peptides.

A non-replicating, transformation-ready circular molecule may contain site-specific recombination sites, and preferably one recombination site. For the purposes of this discussion, a site-specific recombination site comprises a sequence that is recognized by and acted upon by an integrase type recombinase to effect DNA recombination, including but not limited to, an insertion, deletion or inversion of sequences directed by the recombination site sequences. Examples of recombinase and recombination site pairs include, but are not limited to, FLP/frt from yeast and CRE/lox from bacteriophage P1. Lox sites allow CRE-recombinase-mediated integration of a circular molecule into the host DNA, preferably into a lox site in the nuclear chromosomal DNA and most preferably, in a location comprising a lox66 or a lox71 site. The inclusion of a first lox site in the circular molecule can result in the insertion of an entire circular molecule into the nucleic acid comprising a second single lox site. The use of one or fewer lox sites each in the circular molecule and the target DNA is thought to reduce or eliminate extraneous recombination events such as deletion, inversion or duplication of a region that may occur when sequences are flanked by lox or other homologous sequences.

Site-specific recombination in a plant plastid genome has been disclosed (PCT Publications WO 01/21768 and WO 01/29241). It is contemplated that CRE-recombinase-mediated, site-specific recombination with mitochondrial or chloroplastic genomic DNA may also occur should these genomes contain lox sites in their nucleic acid sequences.

A primer set that is used to amplify a starting dsDNA circular template in a PCR reaction can be designed to hybridize to one of several different locations on the starting template. A primer set that is used to amplify a starting ssDNA circular template in a PCR reaction can be designed to hybridize to one of several different locations on the single-stranded molecule as well as on the complementary strand to the starting strand. In one embodiment, the primers can share complete complementarity, e.g., overlap by 100% of the bases, share 100% homology to each other, and hybridize to the same region of the starting template (see for example, FIG. 2B). These oligonucleotide primers are designated as non-mutagenizing primers.

In another embodiment, the non-mutagenizing primers may overlap by fewer than 100% of the bases, preferably from about 99% to about 60% of the sequence, more preferably from about 75% to about 99% of the sequence, most preferably from about 90% to about 99% of the sequence and even more preferably from about 95% to about 99% of the sequence. The primers can be of varying lengths, preferably about 5 to about 50 nucleotides in length, more preferably about 7 to about 45 nucleotides in length and even more preferably about 10 to about 40 nucleotides in length. One of skill in the art can design primers of the proper location, length and overlap for the optimum production of transformation-ready circular molecules in the PCR reaction.

In one embodiment of the invention, the starting circular dsDNA or ssDNA template used to make the non-replicating, transformation-ready dsDNA circles of the invention can be added to the PCR reaction as a single variant, that is, containing a single arrangement of selected sequences in one or more expression units, with one set of primer pairs. In another embodiment of the invention, the starting circular dsDNA or ssDNA template used to make the transformation-ready dsDNA circles of the invention can be added to the PCR reaction as two or more variants, with each variety of template containing a unique, single arrangement of selected sequences in one or more expression units. One or more primer sets for each variety of circular template may be added or a single primer set hybridizing to a common region on all circular templates may be added. One of skill in the art could vary the PCR reaction and conditions to accommodate various starting template and primer combinations to allow for the optimum production of transformation-ready circular molecules in the PCR reaction.

Components of the PCR reaction may be varied as needed to accommodate the size or composition of the template molecules added for amplification. For example, molecules of greater length may necessitate a longer extension time during cycling or additional nucleotides may be required. An additional parameter to consider is the choice of thermostable DNA polymerase enzyme. One of skill in the art would recognize that a variety of suppliers offer thermal tolerant, DNA polymerases. One of the most commonly used enzymes is Taq polymerase, isolated from *Thermus aquaticus*. Taq polymerase has been observed to vary widely in fidelity of synthesis, ranging from $\sim 2\times10^{-4}$ to $<1\times10^{-5}$ mutations per nucleotide per cycle (Eckert and Kunkel, 1991; Lundberg et al., 1991).

Fidelity of polymerization may be enhanced by the addition of a 3'–5' exonuclease or "proofreading" enzyme to the PCR reaction. A source of proofreading activity is the DNA polymerase isolated from archaebacterium *Pyrococcus furiosus* (Pfu). Pfu polymerase has been shown to have $\sim$10-fold greater fidelity than Taq polymerase (Lundberg et al., 1991). Another source of a high-fidelity, thermostable DNA polymerase is *Thermococcus litoralis* which has been shown to have an error rate as low as $30\times10^{-6}$ (Mattila et al., 1991). In addition to differences in fidelity, it is known in the art that some polymerases, e.g., Taq polymerase, have terminal transferase activity. It is preferred to use polymerase enzymes without terminal transferase activity in the practice of the present invention. A number of commercial varieties of Taq and Pfu thermostable DNA polymerases, or combinations of these and other enzymes (Cheng et al., 1994; Cline et al., 1996), are available and one of skill in the art would select the appropriate enzyme based upon experimental parameters, including but not limited to, acceptable error rate, length of template, content of template, primers used for extension, and amount of amplified product needed. It is understood that advances in technology may result in DNA polymerases with increased fidelity and ability to synthesize long molecules which would be beneficial to the execution of the present invention. A plurality of non-replicating, transformation-ready circular molecules generated by PCR amplification is considered to be substantially identical, that is, when using non-mutagenizing primers and optimal PCR reaction conditions, all PCR products are identical with the exception of any errors introduced by the amplification process.

Several references in the literature discuss methods and parameters which can be varied to optimize for the production of accurate, long DNA molecules (Ohler and Rose, 1992; Cheng et al., 1994; Takita et al., 1997; Fang et al., 1998; Lindberg and Andersson, 1999). One of skill in the art would recognize that parameters for particular templates may need to be investigated and optimized as needed to generate the transformation-ready circular molecules of the invention.

II. Recombination Systems

Site-specific integrase recombinase systems have been identified in several organisms including, but not limited to, the CRE/lox system of bacteriophage P1 (Abremski et al., 1983; U.S. Pat. Nos. 4,959,317; 5,658,772), the FLP/frt system of yeast (Golic and Lindquist, 1989), the Pin recombinase of *E. coli* (Enomoto et al., 1983), the Gin/gix recombinase of phage Mu (Maeser et al., 1991) and the R/RS system of the pSR1 plasmid from *Xygosaccharomyces rouxii* (Onouchi et al., 1991; Araki et al., 1992). All of these systems have been shown to function in plants (O'Gorman et al., 1991; Maeser et al., 1991; Onouchi et al., 1991; Dale and Ow, 1991). It is believed that site-directed integration systems like CRE/lox or FLP/frt require a circular DNA intermediate. Of these systems, CRE/lox and FLP/frt have been widely utilized.

The FLP/frt system is native to the yeast *Saccharomyces cerevisiae* (Golic and Lindquist, 1989; reviewed in Futcher, 1988). In yeast, the recombinase enzyme (FLP) resides on a 2μm plasmid and recognizes 599 base pair (bp) inverted repeats (frt) as target sites. The minimal functional sequence unit within the 599 bp repeats includes only 34 bp; two 13 bp inverted repeats separated by an asymmetric 8 bp spacer region although a third, non-essential repeat of the 13 bp sequence is often present (Sauer, 1994). FLP-mediated rearrangement of DNA flanked by inverted repeats of frt sequence often results in the inversion of the DNA between the frt target sites. In this case, both frt sites are retained. FLP recombinase can also recognize directly repeated frt target sites. FLP-mediated rearrangements of DNA flanked by directly repeated frt sites often results in the excision of the DNA located between the frt target sites. In this case, the excised DNA is released in circular form comprising one frt site while the second frt site remains on the template DNA molecule. FLP recombinase can also mediate recombination between frt sites on different DNA molecules; for example, FLP recombinase can mediate recombination between frt sites on different chromosomes. Sadowski (1995) has shown that recombination catalyzed by FLP/frt is reversible in nature.

The DNA exchange catalyzed by FLP/frt can be carried out in vitro as purified FLP recombinase has been shown to mediate recombination between frt sites (Meyer-Leon et al., 1984). The yeast FLP/frt combination has also been used to direct site-specific recombination, both excision and amplification of sequences flanked by frt sites, in *Escherichia coli* (Cox, 1983) as well as in *Drosophila* genomes (Golic and Lindquist, 1989; Golic, 1994). FLP/frt has also been employed to direct site-specific excision of parts of transgenes from plasmid DNA in maize and rice protoplasts by homologous recombination (see, for example, U.S. Pat. No. 5,527,695). FLP/frt has also been utilized in stably transformed maize for site-directed excision of sequences inserted into the maize genome which are flanked by frt sites (U.S. Pat. Nos. 5,929,301 and 6,175,058). Site-specific chromosomal targeting of foreign DNA into bacterial and mammalian chromosomes can also be effected by FLP/frt (Huang et al., 1991; O'Gorman et al., 1991) and this insertion by FLP into frt sites has been shown to be reversible in non-yeast genomes (Huang et al., 1997). It is possible to sufficiently alter frt sites such that recombination occurs but is not reversible (U.S. Pat. No. 6,187,994) or favors a forward reaction relative to a reverse reaction (Senecoff et al., 1988).

A second well characterized recombination system is that of CRE/lox from bacteriophage P1 (Abremski et al., 1983; reviewed in Craig, 1988; Sauer, 1994; Ow, 1996). CRE recombinase (<u>c</u>ausing <u>re</u>combination) recognizes lox (<u>lo</u>cus of crossing <u>o</u>ver (<u>x</u>)) target sequences and mediates site-specific recombination between compatible lox sites. Compatible sites may or may not comprise identical sequences. Lox sites are 34 base pairs in length, comprising two 13 bp inverted repeats separated by 8 bp of other spacer nucleotides. Lox sequences include loxP from bacteriophage P1 (Albert et al., 1995) as well as loxB, loxL, and loxR sites which are nucleotide sequences isolated from *E. coli* (Hoess et al., 1982). Functional variants of loxP sites reported include, but are not limited to, lox66, lox71 and lox72 (Albert et al., 1995). Lox sequences can also be produced by a variety of synthetic techniques which are known in the art.

Examples of synthetic techniques for producing functional lox sites are disclosed by Ogilvie et al. (1981) and Ito et al. (1982).

The lox site is an asymmetrical nucleotide sequence and as such, lox sites on the same DNA molecule can have the same or opposite orientation with respect to each other. Recombination between lox sites in the same orientation results in a deletion of the DNA segment located between the two lox sites. In this case, ligation between the resulting ends of the original DNA molecule occurs and a lox site is retained. The deleted DNA segment forms a circular molecule of DNA which also contains a single lox site. Recombination between lox sites in opposite orientations on the same DNA molecule results in an inversion of the nucleotide sequence of the DNA segment located between the two lox sites. In addition, reciprocal exchange of DNA segments proximate to lox sites located on two different DNA molecules can occur. All of these recombination events are catalyzed by the product of the CRE coding region and are reversible. It is possible, however, to sufficiently alter lox sites such that recombination events occur but are resistant to the reverse recombination reaction (Albert et al., 1995; Araki et al., 1997; PCT Publication WO 01/11058) or such that two sites are "non-compatible" recombination substrates for the recombinase (Hoess et al., 1986; Trinh and Morrison, 2000; Lee and Saito, 1988; EP 1 035 208). It is also possible to prevent the reverse reaction from occurring be removing the source of recombinase, for example, by breeding or use of particular regulatory promoters.

CRE recombinase also effects site-directed integration. For example, a lacZ reporter gene was integrated into the genome of Chinese Hamster Ovary (CHO) cells using CRE-recombinase, a single lox site on the lacZ targeting vector and a single lox site previously located within the CHO genomic DNA (Fukushige and Sauer, 1992). CRE recombinase has been shown to mediate recombination between lox sites in yeast (Sauer, 1987) and plants, such as tobacco and *Arabidopsis* (see, for example, U.S. Pat. No. 5,658,772; Medberry, et al., 1995; Albert et al., 1995) as well as in mammalian cells such as mice (Sauer and Henderson, 1988; Fukushige and Sauer, 1992; Sauer, 1998). Site-specific integration of large BAC (bacterial artificial chromosome) fragments into plant and fungal genomes utilizing a CRE/lox recombination system has also been reported (Choi et al., 2000). It is believed that in order to achieve site-directed integration into a single genomic lox site, a circular DNA molecule comprising a single lox site must be introduced into the cell. Therefore, the methods of the present invention make it possible to achieve site-directed integration of DNA molecules lacking ancillary sequences that are often present in order to replicate and maintain the circular molecules in a bacterial host cell. Wallace et al., (2000) and Day et al., (2000) discuss the use of site-directed integration as a method to pre-select sites in the genome for repeatable expression of transgenes in embryonic stem cells or tobacco, respectively.

CRE recombinase can contact and effect recombination utilizing a number of lox sites including, but not limited to loxP (wild type; SEQ ID NO:1) and a number of variants of the wild type loxP site such as lox66 (Albert et al., 1995; SEQ ID NO:2). The DNA exchange directed by the lox sites occurs in the 8 bp spacer region and essentially effects an exchange of the 13 bp inverted repeats of the two lox sites involved. For example, site-directed recombination in which a single lox site on one DNA molecule recombines with a second single lox site on a second DNA molecule generates a sequence in which the integrated DNA is flanked by a lox site on either side. When the single lox sites on the separate molecules involved are identical, the two resultant lox sites adjacent to the inserted DNA are also identical. If, however, the two single lox sites on the starting molecules are non-identical in the 13 bp inverted repeats, the two resultant lox sites adjacent to the inserted DNA will differ from the starting lox sites. For example, if a first single lox66 site (SEQ ID NO:2) is involved in site-directed integration with a second single lox71 site (SEQ ID NO:3), the resultant lox sites flanking the inserted DNA comprise sequences of loxP and lox72 sites (Albert et al., 1995; SEQ ID NO:1 and SEQ ID NO:4).

Site-directed integration utilizing identical lox or frt sites on the two recombining molecules results in the inserted DNA being flanked by identical recombination sites, a reaction that is easily reversed by the recombinase. To prevent the deletion of the inserted sequence, it is often desirable to remove the source of recombinase enzyme, for example, by segregation or by placing the recombinase gene under the control of an inducible promoter and removing the inducing source. Alternatively, one of skill in the art may use site-specific recombination sequences designed such that after the integration reaction, the resultant sites are non-compatible for a reverse reaction or recombine at a reduced rate.

One of skill in the art will recognize that the integrase enzyme, such as CRE or FLP recombinase, can be provided to the target site or sites, such as lox or frt, by any means known in the art. For example, the recombinase can be transiently supplied by expression from a gene, and appropriate control sequences, that reside on a separately maintained plasmid within the host cells. The recombinase gene and appropriate control sequences can be inserted into the genome of the organism and stably expressed in the host cells. Alternatively, sexual crossing or breeding may be used to introduce the recombinase to cells containing the target lox or frt site or sites; in this instance, an organism such as plant containing the recombinase gene could be crossed to a plant containing the target lox or frt sites and progeny from this union would contain both the recombinase and the target site or sites. In some cases, mRNA coding for the desired recombinase can be introduced into the host cells to encode and provide the recombinase protein. In other cases, one may introduce isolated recombinase protein into a host cell comprising a target recombination site. In any of these cases, the promoter directing recombinase expression may be, but not limited to, constitutive or inducible in manner. One of skill in the art will also recognize that the genes for recombinase genes such as CRE or FLP may be isolated from bacteriophage P1 or *Saccharomyces cerevisiae,* respectively, and utilized directly in a new host system or the gene sequence may be optimized for codon usage for expression in the transgenic host. In a similar fashion, one of skill in the art will recognize that naturally occurring as well as synthetic target sites may be recognized and mediate recombination with an appropriate recombinase.

Examples of recombinase mediated gene replacement or gene excision typically utilize two target sites flanking the sequence to be replaced or excised. For example, Odell et al. (U.S. Pat. No. 5,658,772) disclose the use of two loxP sites and CRE-recombinase to generate specific gene replacements in tobacco. The CRE/lox system has also been used in an inducible manner to activate and to remove transgenes in transgenic plants (PCT Publication WO 01/40492). Baszczynski et al. (U.S. Pat. No. 6,187,994) disclose the use of multiple, non-identical frt sites and FLP-recombinase to generate a variety of gene alterations in maize. Baszczynski et al. (U.S. Pat. No. 6,262,341) also disclose the use of a chimeric CRE/FLP recombinase with dual target site specificity to effect recombination of DNA sequences flanked by a lox sequence on one side and a frt sequence on another side. In each of these cases, the integration or excision of sequences generates extraneous DNA fragments as part of the recombination schema. Site-directed integration, however, may utilize only one target site in the recipient genome. The present invention proposes CRE-mediated, targeted integration of a non-replicating, in vitro generated, transformation-ready circular molecule containing a first single lox site into a second single lox site previously introduced into the target genome.

III. Plant Transformation Constructs

The construction of molecular starting materials, circular templates or transformation-ready circular molecules which may be employed in conjunction with plant transformation techniques according to the invention will be known to those of skill of the art in light of the present disclosure (see, for example, Ausubel et al., 2001; Sambrook and Russell, 2001; Gelvin et al., 1990). The techniques of the current invention are thus not limited to any particular DNA sequences. One important use of the sequences of the invention will be in creating cells expressing a selected coding region which encodes a particular protein or polypeptide product. The inventors also contemplate that, where both an expressible gene that is not necessarily a marker gene is employed in combination with a marker gene, one may employ the separate genes on either the same or different transformation-ready circular molecules for transformation. In the latter case, the different circular molecules are delivered concurrently to recipient cells to maximize cotransformation.

Non-replicating, transformation-ready circular molecules used for transforming plant cells will, of course, generally comprise the cDNA, gene or genes which one desires to introduced into and have expressed in the host cells. These DNA molecules can include sequences such as promoters, enhancers, 3'UTRs, polylinkers, or even regulatory genes as desired. The transformation-ready circular DNA molecules chosen for cellular introduction may encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with transformation-ready circular molecules used in the current invention are as follows.

A. Regulatory Elements

Several types of regulatory sequences may be used in the preparation of non-replicating, transformation-ready circular molecules. One such application in accordance with the instant invention will be the preparation of transformation molecules comprising a promoter operably linked to a selected coding region. Promoters are usually located 5' to the selected coding region or other sequence of interest and can direct expression of the selected sequence in a variety of manners. For example, promoters which are useful for plant transgene expression include those that are inducible, viral, synthetic or constitutive (Paszkowski et al., 1984; Odell et al., 1985). Other promoters useful for plant transgene expression may be temporally regulated, spatially regulated, or spatio-temporally regulated (Chau et al., 1989). There are several plant promoters identified that are useful for expression transgenes in plants including, but are not limited to, a constitutive CaMV 35S promoter (Odell et al., 1985), an inducible glyceraldehyde-3-phosphate dehydrogenase gene promoter (Kohler et al., 1995; Quigley et al., 1989; Martinez et al., 1989) and a tissue specific corn alcohol dehydrogenase 1 promoter (Vogel et al., 1989; Dennis et al., 1984).

By including an enhancer sequence with such constructs, the expression of the selected protein may be enhanced. These enhancers often are found 5' to the start of transcription in a promoter that functions in eukaryotic cells, but can often be inserted in the forward or reverse orientation 5' or 3' to the coding sequence. In some instances, these 5' enhancing elements are introns. Deemed to be particularly useful as enhancers are the 5' introns of the rice actin 1 and rice actin 2 genes. Examples of other enhancers which could be used in accordance with the invention include elements from the CaMV 35S promoter, octopine synthase genes (Ellis et al., 1987), the maize alcohol dehydrogenase gene, the maize shrunken 1 gene and promoters from non-plant eukaryotes (e.g., yeast; Ma et al., 1988).

Where an enhancer is used in conjunction with a promoter for the expression of a selected protein, it is believed that it will be preferred to place the enhancer between the promoter and the start codon of the selected coding region. However, one also could use a different arrangement of the enhancer relative to other sequences and still realize the beneficial properties conferred by the enhancer. For example, the enhancer could be placed 5' of the promoter region, within the promoter region, within the coding sequence (including within any other intron sequences which may be present), or 3' of the coding region.

In addition to introns with enhancing activity, other types of elements can influence gene expression. For example, untranslated leader sequences predicted to enhance gene expression as well as "consensus" and preferred leader sequences have been made (Joshi, 1987). Preferred leader sequences are contemplated to include those which have sequences predicted to direct optimum expression of the attached coding region, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants, and in maize in particular, will be most preferred, for example, sequences derived from the small subunit of ribulose bisphosphate carboxylase (rubisco).

Enhancer elements, such as the ocs enhancer element, may also be used in transformation-ready circular molecules in accordance with the present invention. This element was first identified as a 16 bp palindromic enhancer from the octopine synthase (ocs) gene of *Agrobacterium* (Ellis et al., 1987), and is present in at least 10 other promoters (Bouchez et al., 1989). It is proposed that the use of an enhancer element, such as the ocs element and particularly multiple copies of the element, may be used to increase the level of transcription from adjacent promoters when applied in the context of monocot transformation.

Ultimately, the most desirable DNA segments for introduction into a plant genome may be homologous genes or gene families which encode a desired trait, and which are introduced under the control an appropriate promoter, whereby the expression is enhanced by an actin 1 intron 1 or actin 2 intron 1.

It also is contemplated that expression of one or more transgenes may be eliminated upon induction of a promoter operably linked to a gene or sequence of interest. In particular, by operably linking a promoter to a particular coding sequence in antisense orientation, accumulation of the respective protein encoded by the sense transcript could be eliminated or decreased upon induction or expression of the introduced promoter. This could allow, for example, inducible elimination of a particular gene product which would contribute to the ill effects of osmotic stress or attack by pests, disease, or other conditions.

It is particularly contemplated in this invention that it may be useful to target DNA within a cell. For example, it may be useful to target introduced DNA to the nucleus and, within the nucleus itself, it would be useful to target a gene in order to achieve site-specific integration. For example, it would be useful to have a gene introduced through transformation replace an existing gene in the cell. Furthermore, it would be useful to target a transgene to integrate into the genome at a predetermined site from which it is known that gene expression occurs. Several site-specific recombination systems exist which are known, including CRE/lox (U.S. Pat. No. 4,959,317) and FLP-FRT (U.S. Pat. No. 5,527,695). Both of these cited site-specific recombination systems have been shown to function in plants (Albert et al., 1995; Lyznik et al., 1996). In one embodiment of the invention, it would be desirable to insert into the target genome a regulatory element such as, but not limited to, a promoter, enhancer, untranslated sequence or intron, adjacent to a target site, such as a lox site. Site-specific integration of a transformation-ready circular molecule with a gene of interest into a lox site proximal to such regulatory sequences would operably link the gene of interest to the regulatory sequence and allow expression of the integrated DNA.

B. 3' Untranslated Regions

Transformation-ready circular molecules prepared in accordance with the invention will typically include a 3' end DNA sequence that acts as a signal to cease transcription and allow for the poly-adenylation of the mRNA produced by coding sequences operably linked to a promoter. This 3' end sequence is often called a 3'UTR, 3' end or simply 3'. One type of 3'UTR sequence which may be used is a 3'UTR from the nopaline synthase gene of *Agrobacterium tumefaciens* (nos 3' end; Bevan et al., 1983). Where a 3' end other than a nos 3'UTR is used in accordance with the invention, the most preferred 3' ends are contemplated to be those from a gene encoding the small subunit of a ribulose-1,5-bisphosphate carboxylase-oxygenase (rbcS), and more specifically, from a rice rbcS gene (PCT Publication WO 00/70066), the 3'UTR for the T7 transcript of *Agrobacterium tumefaciens* (Dhaese et al., 1983), the 3' end of the protease inhibitor I or II genes from potato (Graham et al., 1986) or tomato (Pearce et al., 1991), and the 3' region isolated from Cauliflower Mosaic Virus (Timmermans et al., 1990). Alternatively, one also could use a gamma coixin, oleosin 3 or other 3'UTRs from the genus Coix (PCT Publication WO 99/58659).

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus, peroxisomes or glyoxysomes, and outside of the cellular membrane). By facilitating the transport of the protein into compartments inside and outside the cell, these sequences may increase the accumulation of a gene product protecting the protein from intracellular proteolytic degradation. These sequences also allow for additional mRNA sequences from highly expressed genes to be attached to the coding sequence of the genes. Since mRNA being translated by ribosomes is more stable than naked mRNA, the presence of translatable mRNA 5' of the gene of interest may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

A particular example of such a use concerns the direction of a protein conferring herbicide resistance, such as a mutant EPSPS protein, to a particular organelle such as the chloroplast rather than to the cytoplasm. This is exemplified by the use of the rbcS transit peptide, the chloroplast transit peptide described in U.S. Pat. No. 5,728,925, or the optimized transit peptide described in U.S. Pat. No. 5,510,471, which confers plastid-specific targeting of proteins. In addition, it may be desirable to target certain genes responsible for male sterility to the mitochondria, or to target certain genes for resistance to phytopathogenic organisms to the extracellular spaces, or to target proteins to the vacuole. A further use concerns the direction of enzymes involved in amino acid biosynthesis or oil synthesis to the plastid. Such enzymes include dihydrodipicolinic acid synthase which may contribute to increasing lysine content of a feed.

Additionally, transformation-ready circular molecules may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. An intracellular targeting DNA sequence may be operably linked 5' or 3' to the coding sequence depending on the particular targeting sequence. The resultant transit, or signal, peptide will transport the protein to a particular intracellular, or extracellular destination, respectively, and will then be post-translationally removed.

D. Marker Genes

One application of the non-replicating, transformation-ready circular molecules of the current invention will be in the expression of marker proteins. By employing a selectable or screenable marker gene as, or in addition to, the gene of interest, one can provide or enhance the ability to identify transformants. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening"' (e.g., the green fluorescent protein). Of course, many examples of suitable marker genes are known to the art and can be employed in the practice of the invention.

Included within the terms selectable or screenable marker genes also are genes which encode a "secretable marker"

whose secretion can be detected as a means of identifying or selecting for transformed cells. Examples include marker genes which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). The use of maize HPRG (Steifel et al., 1990) is preferred, as this molecule is well characterized in terms of molecular biology, expression and protein structure. However, any one of a variety of extensins and/or glycine-rich wall proteins (Keller et al., 1989) could be modified by the addition of an antigenic site to create a screenable marker.

One exemplary embodiment of a secretable screenable marker concerns the use of a HPRG sequence modified to include a 15 residue epitope from the pro-region of murine interleukin-1β (IL-1β). However, virtually any detectable epitope may be employed in such embodiments, as selected from the extremely wide variety of antigen:antibody combinations known to those of skill in the art. The unique extracellular epitope, whether derived from IL-1β or any other protein or epitopic substance, can then be straightforwardly detected using antibody labeling in conjunction with chromogenic or fluorescent adjuncts.

1. Selectable Markers

Many selectable marker coding regions may be used in connection with a transformation-ready circular molecule of the present invention including, but not limited to, neo (Potrykus et al., 1985) which provides kanamycin resistance and can be selected for using kanamycin, G418, paromomycin, etc.; bar, which confers bialaphos or pbosphinothricin resistance (Murakami et al., 1986; Thompson et al., 1987 De Block et al., 1987; De Block et al., 1989; U.S. Pat. No. 5,550,318); a glyphosate resistant EPSP synthase protein (Hinchee et al., 1988); a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (EP 0 154 204); a methotrexate resistant DHFR (Thillet et al., 1988), a dalapon dehalogenase that confers resistance to the herbicide dalapon; or a mutated anthranilate synthase that confers resistance to 5-methyl tryptophan or other anthranilate synthase inhibiting compounds. Where a glyphosate resistant EPSP synthase is employed, additional benefit may be realized through the incorporation of a suitable chloroplast transit peptide, CTP (U.S. Pat. No. 5,188,642) or OTP (U.S. Pat. No. 5,633,448).

An illustrative example of an herbicide which is useful for selection of transformed cell lines in the practice of the invention is the broad spectrum herbicide glyphosate. Glyphosate affects the aromatic amino acid biosynthetic pathway of plants by inhibiting the enzyme 5-enolpyruvylshikimate 3-phosphate synthase or EPSPS. Inhibition of this enzyme leads to starvation for the amino acids phenylalanine, tyrosine, and tryptophan and secondary metabolites derived thereof. Mutations of EPSPS conferring glyphosate resistance on the *Salmonella typhimurium* gene for EPSPS, aroA, have been disclosed (U.S. Pat. No. 4,535,060). The EPSPS gene was cloned from *Zea mays* and mutations similar to those found in a glyphosate resistant aroA gene were introduced in vitro. Mutant genes encoding glyphosate resistant EPSPS enzymes are described in, for example, PCT Publication WO 97/04103. Naturally occurring glyphosate resistant EPSPS exist and are preferably used, e.g., the CP4 gene isolated from *Agrobacterium* encodes a glyphosate resistant EPSPS (U.S. Pat. No. 5,627,061).

2. Screenable Markers

Screenable markers that may be employed include a β-glucuronidase or uidA gene (Jefferson et al., 1986; the protein product is commonly referred to as GUS), isolated from *E. coli*, which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; PCT Publication WO 97/41228).

Genes from the maize R gene complex are contemplated to be useful as screenable markers. The R gene complex in maize encodes a protein that acts to regulate the production of anthocyanin pigments in most seed and plant tissue. Maize strains can have one, or as many as four, R alleles which combine to regulate pigmentation in a developmental and tissue specific manner. Thus, an R gene introduced into such cells will cause the expression of a red pigment and, if stably incorporated, can be visually scored as a red sector. If a maize line carries dominant alleles for genes encoding for the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which has the genotype r-g, b, P1. Alternatively, any genotype of maize can be utilized if the C1 and R alleles are introduced together.

It further is proposed that R gene regulatory regions may be employed in chimeric constructs in order to provide mechanisms for controlling the expression of chimeric genes. More diversity of phenotypic expression is known at the R locus than at any other locus (Coe et al., 1988). It is contemplated that regulatory regions obtained from regions 5' to the structural R gene would be valuable in directing the expression of genes for, e.g., insect resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

Other screenable markers provide for visible light emission as a screenable phenotype. A screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is contemplated as a particularly useful reporter gene (Sheen et al., 1995; Haseloff et al., 1997; Reichel et al., 1996; Tian et al., 1997; PCT Publication WO 97/41228). Expression of green fluorescent protein may be visualized in a cell or plant as fluorescence following illumination by particular wavelengths of light. Where use of a screenable marker gene such as lux or GFP is desired, the inventors contemplated that benefit may be realized by creating a gene fusion between the screenable marker gene and a selectable marker gene, for example, a GFP-NPTII gene fusion (PCT Publication WO 99/60129). This could allow, for example, selection of transformed cells followed by screening of transgenic plants or seeds. In a similar manner, it is possible to utilize other readily available fluorescent proteins such as red fluorescent protein (CLONTECH, Palo Alto, Calif.).

IV. Exogenous Genes for Modifications of Plant Phenotypes

A particularly important advantage of the present invention is that it provides methods and compositions for the efficient expression of selected genes in plant cells. In particular, the current invention provides a means of generating transformation-ready circular molecules for site-directed integration into plants and subsequent expression of selected genes of interest. Use of preselected, characterized integration sites will allow reproducible expression of transformed sequences.

The choice of a selected gene for expression in a plant host cell in accordance with the invention will depend on the purpose of the transformation. One of the major purposes of transformation of crop plants is to add commercially desirable, agronomically important or end-product traits to the plant. Such traits include, but are not limited to, herbicide resistance or tolerance, insect resistance or tolerance, disease resistance or tolerance (viral, bacterial, fungal, nematode), stress tolerance and/or resistance, as exemplified by resistance or tolerance to drought, heat, chilling, freezing, excessive moisture, salt stress and oxidative stress, increased yield, food or feed content and value, physical appearance, male sterility, drydown, standability, prolificacy, starch quantity and quality, oil quantity and quality, protein quality and quantity, amino acid composition, and the like.

In certain embodiments of the invention, transformation of a recipient cell by non-replicating, transformation-ready circular molecules may be carried out with more than one selected gene. As used herein, an "exogenous coding region" or "selected coding region" is a coding region not normally found in the host genome in an identical context. By this, it is meant that the coding region may be isolated from a different species than that of the host genome, or alternatively, isolated from the host genome, but is operably linked to one or more regulatory regions which differ from those found in the unaltered, native gene. Two or more exogenous coding regions also can be supplied in a single transformation event using distinct transgene-encoding transformation-ready circular molecules comprising distinct, non-compatible lox sites, or using transformation-ready circular molecules in a mixture with other transformation vectors, molecules or cassettes, or preferably using a single variant of transformation-ready circular molecule incorporating two or more selected coding sequences. For example, circular molecules bearing a gene encoding a selectable marker, such as npt II or glyphosate resistant EPSP synthase (e.g., CP4 (U.S. Pat. No. 5,627,061)) and a gene conferring a desirable phenotype in either convergent, divergent, or colinear orientation, are considered to be particularly useful. Genes conferring desirable phenotypes included those conferring insect resistance, such as a *Bacillus thuringiensis* gene (BT gene) or those conferring herbicide, insect, disease (viral, bacterial, fungal, nematode) or drought resistance, male sterility, drydown, standability, prolificacy, starch properties, oil quantity and quality, or those increasing yield or nutritional quality.

A. Herbicide Resistance

The DNA segments encoding phosphinothricin acetyltransferase (bar and pat), EPSP synthase encoding genes conferring resistance to glyphosate, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP synthase or EPSPS), is inhibited by the herbicide N-(phosphonomethyl) glycine (glyphosate) in most plants and microorganisms. However, genes are known that encode glyphosate-resistant EPSP synthase enzymes, including mutated EPSPS genes, e.g., the *Salmonella typhimurium* aroA CT7 mutant (Comai et al., 1985) and the naturally occurring glyphosate resistant EPSPS from *Agrobacterium*, CP4 (U.S. Pat. No. 5,627,061). These genes are particularly contemplated for use in plant transformation. The deh gene encodes the enzyme dalapon dehalogenase and confers resistance to the herbicide dalapon (U.S. Pat. No. 5,780,708). The bxn gene codes for a specific nitrilase enzyme that converts bromoxynil to a non-herbicidal degradation product.

B. Insect Resistance

Potential insect resistance genes that can be introduced include *Bacillus thuringiensis* crystal toxin genes or Bt genes (Watrud et al., 1985). Bt genes may provide resistance to economically important lepidopteran or coleopteran pests such as European Corn Borer (ECB) and Western Corn Rootworm, respectively. It is contemplated that preferred Bt genes for use in the transformation methods disclosed herein will be those in which the coding sequence has been modified to effect increased expression in plants, and more particularly, in maize. Means for preparing synthetic genes are well known in the art and are disclosed in, for example, U.S. Pat. Nos. 5,500,365 and 5,689,052, each of the disclosures of which are specifically incorporated herein by reference in their entirety. Examples of such modified Bt toxin genes include a synthetic Bt CryIA(b) gene (Perlak et al., 1991), and the synthetic CryIA(c) gene termed 1800b (PCT Publication WO 95/06128). Some examples of other Bt toxin genes known to those of skill in the art are given in Table 1 below.

TABLE 1

Bacillus thuringiensis δ-Endotoxin Genes[a]

| New Nomenclature | Old Nomenclature | GenBank Accession |
|---|---|---|
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | 722513 |
| Cry1Hb |  | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K |  | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |
| Cry13A | CryVC | L07023 |
| Cry14A | CryVD | U13955 |
| Cry15A | 34kDa | M76442 |
| Cry16A | cbm71 | X94146 |
| Cry17A | cbm71 | X99478 |

TABLE 1-continued

Bacillus thuringiensis δ-Endotoxin Genes[a]

| New Nomenclature | Old Nomenclature | GenBank Accession |
|---|---|---|
| Cry18A | CryBP1 | X99049 |
| Cry19A | Jeg65 | Y08920 |
| Cyt1Aa | CytA | X03182 |
| Cyt1Ab | CytM | X98793 |
| Cyt2A | CytB | Z14147 |
| Cyt2B | CytB | U52043 |

[a]Adapted from: http://epunix.biols.susx.ac.uk/Home/Neil_Crickmore/Bt/index.html Protease inhibitors also may provide insect resistance (Johnson et al., 1989), and thus will have utility in plant transformation. The use of a protease inhibitor II gene, pinII, from tomato or potato is envisioned to be useful. Even more advantageous is the use of a pinII gene in combination with a Bt toxin gene, the combined effect of which has been discovered to produce synergistic insecticidal activity. Other genes which encode inhibitors of the insect's digestive system, or those that encode enzymes or co-factors that facilitate the production of inhibitors, also may be useful. This group may be exemplified by oryzacystatin and amylase inhibitors such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock et al., 1990; Czapla & Lang, 1990). Lectin genes contemplated to be useful include, for example, barley and wheat germ agglutinin (WGA) and rice lectins (Gatehouse et al., 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, also may result in insecticidal activity, or perhaps cause cessation of metamorphosis (Hammock et al., 1990).

Transgenic plants expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant plants. Genes that code for activities that affect insect molting, such as those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests also are encompassed by the present invention. It may be possible, for instance, to confer insecticidal activity on a plant by altering its sterol composition. Sterols are obtained by insects from their diet and are used for hormone synthesis and membrane stability. Therefore, alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson and Guss, 1972). It further is anticipated that other cereal, monocot or dicot plant species may have genes encoding proteins that are toxic to insects which would be useful for producing insect resistant corn plants.

Further genes encoding proteins characterized as having potential insecticidal activity also may be used as transgenes in accordance herewith. Such genes include, for example, the cowpea trypsin inhibitor (CpTI; Hilder et al., 1987) which may be used as a rootworm deterrent; genes encoding avermectin (Campbell, 1989; Ikeda et al., 1987) which may prove particularly useful as a corn rootworm deterrent; ribosome inactivating protein genes; and even genes that regulate plant structures. Transgenic maize including anti-insect antibody genes and genes that code for enzymes that can convert a non-toxic insecticide (pro-insecticide) applied to the outside of the plant into an insecticide inside the plant also are contemplated.

C. Environment or Stress Resistance

Improvement of a plants ability to respond to various environmental signals, such as but not limited to, light, $CO_2$ or nitrogen, or to tolerate various environmental stresses such as, but not limited to, drought, excess moisture, chilling, freezing, high temperature, salt, and oxidative stress, also can be effected through expression of novel genes. Genes conferring resistance to these conditions may find use with the circular molecules of this invention.

It is proposed that benefits may be realized in terms of increased resistance to freezing temperatures through the introduction of an "antifreeze" protein such as that of the Winter Flounder (Cutler et al., 1989) or synthetic gene derivatives thereof Improved chilling tolerance also may be conferred through increased expression of glycerol-3-phosphate acetyltransferase in chloroplasts (Wolter et al., 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., 1992). Such strategies may allow for tolerance to freezing in newly emerged fields as well as extending later maturity higher yielding varieties to earlier relative maturity zones.

It is proposed that expression of a gene encoding hemoglobin may enhance a plant's ability to assimilate and utilize oxygen, resulting in quicker germination, faster growing or maturing crops, or higher crop yields (Holmberg et al. 1997).

It is contemplated that the expression of novel genes that favorably effect plant water content, total water potential, osmotic potential, and turgor will enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments. In this aspect of the invention it is proposed, for example, that the expression of genes encoding for the biosynthesis of osmotically-active solutes, such as polyol compounds, may impart protection against drought. Within this class are genes encoding for mannitol-L-phosphate dehydrogenase (Lee and Saier, 1983), trehalose-6-phosphate synthase (Kaasen et al., 1992), and myo-inositol O-methyl transferase (U.S. Pat. No. 5,563, 324). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., 1992, 1993). Altered water utilization in transgenic corn producing mannitol also has been demonstrated (U.S. Pat. No. 5,780,709).

Similarly, the efficacy of other metabolites in protecting either enzyme function (e.g., alanopine or propionic acid) or membrane integrity (e.g., alanopine) has been documented (Loomis et al., 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., 1992), sorbitol, dulcitol (Karsten et al., 1992), glucosylglycerol (Reed et al., 1984; Erdmann et al., 1992), sucrose, stachyose (Koster and Leopold, 1988; Blackman et al., 1992), raffinose (Bernal-Lugo and Leopold, 1992), proline (Rensburg et al., 1993), glycine betaine, ononitol and pinitol (Vernon and Bohnert, 1992). Continued canopy growth and increased reproductive fitness during times of stress will be augmented by introduction and expression of genes such as those controlling the osmotically active compounds discussed above and other such compounds. Currently preferred genes which promote the synthesis of an osmotically active polyol compound are genes which encode the enzymes mannitol-1-phosphate dehydrogenase, trehalose-6-phosphate synthase and myo-inositol 0-methyltransferase.

It is contemplated that the expression of specific proteins also may increase drought tolerance. Three classes of Late Embryogenic Proteins have been assigned based on structural similarities (see Dure et al., 1989). All three classes of LEAs have been demonstrated in maturing (i.e., desiccating) seeds. Within these 3 types of LEA proteins, the Type-II (dehydrin-type) have generally been implicated in drought and/or desiccation tolerance in vegetative plant parts (i.e., Mundy and Chua, 1988; Piatkowski et al., 1990; Yamaguchi-Shinozaki et al., 1992). Recently, expression of a Type-III LEA (HVA-1) in tobacco was found to influence plant height, maturity and drought tolerance (Fitzpatrick, 1993). In rice, expression of the HVA-1 gene influenced tolerance to water deficit and salinity (Xu et al., 1996). Expression of structural genes from all three LEA groups may therefore confer drought tolerance. Other types of proteins induced during water stress include thiol proteases, aldolases and transmembrane transporters (Guerrero et al., 1990), which may confer various protective and/or repair-type functions during drought stress. It also is contemplated that genes that effect lipid biosynthesis and hence membrane composition might also be useful in conferring drought resistance on the plant.

Many of these genes for improving drought resistance have complementary modes of action. Thus, it is envisaged that combinations of these genes might have additive and/or synergistic effects in improving drought resistance in crop plants such as, for example, corn, soybean, cotton, or wheat. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al., 1990 and Shagan and Bar-Svi, 1993, which are incorporated herein by reference) or an ABA-inducible promoter such as the promoter of the present invention. Inducible, spatial and temporal expression patterns of these genes may enable plants to better withstand stress.

It is proposed that expression of genes that are involved with specific morphological traits that allow for increased water extractions from drying soil would be of benefit. For example, introduction and expression of genes that alter root characteristics may enhance water uptake. It also is contemplated that expression of genes that enhance reproductive fitness during times of stress would be of significant value. For example, expression of genes that improve the synchrony of pollen shed and receptiveness of the female flower parts, i.e., silks, would be of benefit. In addition it is proposed that expression of genes that minimize kernel abortion during times of stress would increase the amount of grain to be harvested and hence be of value.

Given the overall role of water in determining yield, it is contemplated that enabling corn and other crop plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

D. Disease Resistance

It is proposed that increased resistance to diseases may be realized through introduction of genes into plants, for example, into monocotyledonous plants such as maize. It is possible to produce resistance to diseases caused by viruses, bacteria, fungi and nematodes. It also is contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo et al., 1988, Hemenway et al., 1988, Abel et al., 1986). It is contemplated that expression of antisense genes targeted at essential viral functions also may impart resistance to viruses. For example, an antisense gene targeted at the gene responsible for replication of viral nucleic acid may inhibit replication and lead to resistance to the virus. It is believed that interference with other viral functions through the use of antisense genes also may increase resistance to viruses. Similarly, ribozymes could be used in this context. Further, it is proposed that it may be possible to achieve resistance to viruses through other approaches, including, but not limited to the use of satellite viruses. Examples of viral and viral-like diseases, for which one could introduce resistance to in a transgenic plant in accordance with the instant invention, are listed below, in Table 2.

TABLE 2

Plant Virus and Virus-like Diseases

| DISEASE | CAUSATIVE AGENT |
|---|---|
| American wheat striate (wheat striate mosaic) | American wheat striate mosaic (AWSMV) |
| Barley stripe mosaic | Barley stripe mosaic virus (BSMV) |
| Barley yellow dwarf | Barley yellow dwarf virus (BYDV) |
| Brome mosaic | Brome mosaic virus (BMV) |
| Cereal chlorotic mottle* | Cereal chlorotic mottle virus (CCMV) |
| Corn chlorotic vein banding (Brazilian maize mosaic)[1] | Corn chlorotic vein banding virus (CCVBV) |
| Corn lethal necrosis | Virus complex (Maize chlorotic mottle virus(MCMV) and Maize dwarf mosaic virus (MDMV) A or B or Wheat streak mosaic virus(WSMV)) |
| Cucumber mosaic | Cucumber mosaic virus (CMV) |
| Cynodon chlorotic streak*,[1] | Cynodon chlorotic streak virus (CCSV) |
| Johnsongrass mosaic | Johnsongrass mosaic virus (JGMV) |
| Maize bushy stunt | Mycoplasma-like organism (MLO) associated |
| Maize chlorotic dwarf | Maize chlorotic dwarf virus (MCDV) |
| Maize chlorotic mottle | Maize chlorotic mottle virus (MCMV) |
| Maize dwarf mosaic | Maize dwarf mosaic virus (MDMV) strains A, D, E and F |
| Maize leaf fleck | Maize leaf fleck virus (MLFV) |
| Maize line* | Maize line virus (MLV) |
| Maize mosaic (corn leaf stripe, enanismo rayado) | Maize mosaic virus (MMV) |
| Maize mottle and chlorotic stunt[1] | Maize mottle and chlorotic stunt virus* |
| Maize pellucid ringspot* | Maize pellucid ringspot virus (MPRV) |
| Maize raya gruesa*,[1] | Maize raya gruesa virus (MRGV) |
| maize rayado fino* (fine striping disease) | Maize rayado fino virus (MRFV) |
| Maize red leaf and red stripe* | Mollicute? |
| Maize red stripe* | Maize red stripe virus (MRSV) |
| Maize ring mottle* | Maize ring mottle virus (MRMV) |
| Maize rio IV* | Maize rio cuarto virus (MRCV) |
| Maize rough dwarf* (nanismo ruvido) | Maize rough dwarf virus (MRDV) (=Cereal tillering disease virus*) |
| Maize sterile stunt* | Maize sterile stunt virus (strains of barley yellow striate virus) |
| Maize streak* | Maize streak virus (MSV) |
| Maize stripe (maize chlorotic stripe, maize hoja blanca) | Maize stripe virus |
| Maize stunting*,[1] | Maize stunting virus |
| Maize tassel abortion* | Maize tassel abortion virus (MTAV) |
| Maize vein enation* | Maize vein enation virus (MVEV) |
| Maize wallaby ear* | Maize wallaby ear virus (MWEV) |
| Maize white leaf* | Maize white leaf virus |
| Maize white line mosaic | Maize white line mosaic virus (MWLMV) |
| Millet red leaf* | Millet red leaf virus (MRLV) |
| Northern cereal mosaic* | Northern cereal mosaic virus (NCMV) |
| Oat pseudorosette* (zakuklivanie) | Oat pseudorosette virus |
| Oat sterile dwarf* | Oat sterile dwarf virus (OSDV) |
| Rice black-streaked dwarf* | Rice black-streaked dwarf virus (RBSDV) |
| Rice stripe* | Rice stripe virus (RSV) |
| Sorghum mosaic | Sorghum mosaic virus (SrMV), formerly sugarcane mosaic virus (SCMV) strains H, I and M |
| Sugarcane Fiji disease* | Sugarcane Fiji disease virus (FDV) |
| Sugarcane mosaic | Sugarcane mosaic virus (SCMV) strains A, B, D, E, SC, BC, Sabi and MB (formerly MDMV-B) |
| Vein enation*,[1] | Virus ? |
| Wheat spot mosaic [1] | Wheat spot mosaic virus (WSMV) |

*Not known to occur naturally on corn in the United States.
[1]Minor viral disease.

It is proposed that increased resistance to diseases caused by bacteria and fungi also may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in monocotyledonous plants such as maize may be useful in conferring resistance to bacterial disease. These genes are induced following pathogen attack on a host plant and have been divided into at least five classes of proteins (Bol et al., 1990). Included amongst the PR proteins are β-1, 3-glucanases, chitinases, and osmotin and other proteins that are believed to function in plant resistance to disease organisms. Other genes have been identified that have antifungal properties, e.g., UDA (stinging nettle lectin), hevein (Broakaert et al., 1989; Barkai-Golan et al., 1978), and sor1 conferring resistance to photosensitizing toxins (Ehrenshaft et al., 1999). It is known that certain plant diseases are caused by the production of phytotoxins. It is proposed that resistance to these diseases would be achieved through expression of a novel gene that encodes an enzyme capable of degrading or otherwise inactivating the phytotoxin. It also is contemplated that expression of novel genes that alter the interactions between the host plant and pathogen may be useful in reducing the ability of the disease organism to invade the tissues of the host plant, e.g., an increase in the waxiness of the leaf cuticle or other morphological characteristics. Examples of bacterial and fungal diseases, including downy mildews, for which one could introduce resistance to in a transgenic plant in accordance with the instant invention, are listed below, in Tables 3, 4 and 5.

TABLE 3

Plant Bacterial Diseases

| DISEASE | CAUSATIVE AGENT |
|---|---|
| Bacterial leaf blight and stalk rot | *Pseudomonas avenae* subsp. *avenae* |
| Bacterial leaf spot | *Xanthomonas campestris* pv. *holcicola* |
| Bacterial stalk rot | *Enterobacter dissolvens* = *Erwinia dissolvens* |
| Bacterial stalk and top rot | *Erwinia carotovora* subsp. *carotovora*, *Erwinia chrysanthemi* pv. *zeae* |
| Bacterial stripe | *Pseudomonas andropogonis* |
| Chocolate spot | *Pseudomonas syringae* pv. *coronafaciens* |
| Goss's bacterial wilt and blight (leaf freckles and wilt) | *Clavibacter michiganensis* subsp. *nebraskensis* = *Corynebacterium michiganense* pv. *nebraskense* |
| Holcus spot | *Pseudomonas syringae* pv. *syringae* |
| Purple leaf sheath | Hemiparasitic bacteria + (See under Fungi) |
| Seed rot-seedling blight | *Bacillus subtilis* |
| Stewart's disease (bacterial wilt) | *Pantoea stewartii* = *Erwinia stewartii* |
| Corn stunt (achapparramiento, maize stunt, Mesa Central or Rio Grande maize stunt) | *Spiroplasma kunkelii* |

TABLE 4

Plant Fungal Diseases

| DISEASE | PATHOGEN |
|---|---|
| Anthracnose leaf blight and anthracnose stalk rot | *Colletotrichum graminicola* (teleomorph: *Glomerella graminicola* Politis), *Glomerella tucumanensis* (anamorph: *Glomerella falcatum* Went) |

TABLE 4-continued

Plant Fungal Diseases

| DISEASE | PATHOGEN |
|---|---|
| Aspergillus ear and kernel rot | *Aspergillus flavus* Link:Fr. |
| Banded leaf and sheath spot* | *Rhizoctonia solani* Kühn = *Rhizoctonia microsclerotia* J. Matz (teleomorph: *Thanatephorus cucumeris*) |
| Black bundle disease | *Acremonium strictum* W. Gams = *Cephalosporium acremonium* |
| Black kernel rot* | Auct. non Corda *Lasiodiplodia theobromae* = *Botryodiplodia theobromae* |
| Borde blanco* | *Marasmiellus* sp. |
| Brown spot (black spot, stalk rot) | *Physoderma maydis* |
| Cephalosporium kernel rot | *Acremonium strictum* = *Cephalosporium acremonium* |
| Charcoal rot | *Macrophomina phaseolina* |
| Corticium ear rot* | *Thanatephorus cucumeris* = *Corticium sasakii* |
| Curvularia leaf spot | *Curvularia clavata*, *C. eragrostidis*, = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |
| Didymella leaf spot* | *Didymella exitalis* |
| Diplodia ear rot and stalk rot | *Diplodia frumenti* (teleomorph: *Botryosphaeria festucae*) |
| Diplodia ear rot, stalk rot, seed rot and seedling blight | *Diplodia maydis* = *Stenocarpella maydis* |
| Diplodia leaf spot or leaf streak | *Stenocarpella macrospora* = *Diplodia macrospora* |

*Not known to occur naturally on corn in the United States.

TABLE 5

Plant Downy Mildews

| DISEASE | CAUSATIVE AGENT |
|---|---|
| Brown stripe downy mildew* | *Sclerophthora rayssiae* var. *zeae* |
| Crazy top downy mildew | *Sclerophthora macrospora* = *Sclerospora macrospora* |
| Green ear downy mildew (graminicola downy mildew) | *Sclerospora graminicola* |
| Java downy mildew* | *Peronosclerospora maydis* = *Sclerospora maydis* |
| Philippine downy mildew* | *Peronosclerospora philippinensis* = *Sclerospora philippinensis* |
| Sorghum downy mildew | *Peronosclerospora sorghi* = *Sclerospora sorghi* |
| Spontaneum downy mildew* | *Peronosclerospora spontanea* = *Sclerospora spontanea* |
| Sugarcane downy mildew* | *Peronosclerospora sacchari* = *Sclerospora sacchari* |
| Dry ear rot (cob, kernel and stalk rot) | *Nigrospora oryzae* (teleomorph: *Khuskia oryzae*) |
| Ear rots, minor | *Alternaria alternata* = *A. tenuis*, *Aspergillus glaucus*, *A. niger*, *Aspergillus* spp., *Botrytis cinerea* (teleomorph: *Botryotinia fuckeliana*), *Cunninghamella* sp., *Curvularia pallescens*, *Doratomyces stemonitis* = *Cephalotrichum stemonitis*, *Fusarium culmorum*, *Gonatobotrys simplex*, *Pithomyces maydicus*, *Rhizopus microsporus* Tiegh., *R. stolonifer* = *R. nigricans*, *Scopulariopsis brumptii*. |

TABLE 5-continued

Plant Downy Mildews

| DISEASE | CAUSATIVE AGENT |
|---|---|
| Ergot* (horse's tooth, diente de caballo) | *Claviceps gigantea* (anamorph: *Sphacelia* sp.) |
| Eyespot | *Aureobasidium zeae* = *Kabatiella zeae* |
| Fusarium ear and stalk rot | *Fusarium subglutinans* = *F. moniliforme* var. *subglutinans* |
| Fusarium kernel, root and stalk rot, seed rot and seedling blight | *Fusarium moniliforme* (teleomorph: *Gibberella fujikuroi*) |
| Fusarium stalk rot, seedling root rot | *Fusarium avenaceum* (teleomorph: *Gibberella avenacea*) |
| Gibberella ear and stalk rot | *Gibberella zeae* (anamorph: *Fusarium graminearum*) |
| Gray ear rot | *Botryosphaeria zeae* = *Physalospora zeae* (anamorph: *Macrophoma zeae*) |
| Gray leaf spot (Cercospora leaf spot) | *Cercospora sorghi* = *C. sorghi* var. *maydis*, *C. zeae-maydis* |
| Helminthosporium root rot | *Exserohilum pedicellatum* = *Helminthosporium pedicellatum* (teleomorph: *Setosphaeria pedicellata*) |
| Hormodendrum ear rot (Cladosporium rot) | *Cladosporium cladosporioides* = *Hormodendrum cladosporioides*, *C. herbarum* (teleomorph: *Mycosphaerella tassiana*) |
| Hyalothyridium leaf spot* | *Hyalothyridium maydis* |
| Late wilt* | *Cephalosporium maydis* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot, Helminthosporium ear rot (race 1) | *Cochliobolus carbonum* (anamorph: *Bipolaris zeicola* = *Helminthosporium carbonum*) |
| Penicillium ear rot (blue eye, blue mold) | *Penicillium* spp., *P. chrysogenum*, *P. expansum*, *P. oxalicum* |
| Phaeocytostroma stalk rot and root rot | *Phaeocytostroma ambiguum*, = *Phaeocytosporella zeae* |
| Phaeosphaeria leaf spot* | *Phaeosphaeria maydis* = *Sphaerulina maydis* |
| Physalospora ear rot (Botryosphaeria ear rot) | *Botryosphaeria festucae* = *Physalospora zeicola* (anamorph: *Diplodia frumenti*) |
| Purple leaf sheath | Hemiparasitic bacteria and fungi |
| Pyrenochaeta stalk rot and root rot | *Phoma terrestris* = *Pyrenochaeta terrestris* |
| Pythium root rot | *Pythium* spp., *P. arrhenomanes*, *P. graminicola* |
| Pythium stalk rot | *Pythium aphanidermatum* = *P. butleri* L. |
| Red kernel disease (ear mold, leaf and seed rot) | *Epicoccum nigrum* |
| Rhizoctonia ear rot (sclerotial rot) | *Rhizoctonia zeae* (teleomorph: *Waitea circinata*) |
| Rhizoctonia root rot and stalk rot | *Rhizoctonia solani*, *Rhizoctonia zeae* |
| Root rots, minor | *Alternaria alternata*, *Cercospora sorghi*, *Dictochaeta fertilis*, *Fusarium acuminatum* (teleomorph: *Gibberella acuminata*), *F. equiseti* (teleomorph: *G. intricans*), *F. oxysporum*, *F. pallidoroseum*, *F. poae*, *F. roseum*, *G. cyanogena*, (anamorph: *F. sulphureum*), *Microdochium bolleyi*, *Mucor* sp., *Periconia circinata*, *Phytophthora cactorum*, *P. drechsleri*, *P. nicotianae* var. *parasitica*, *Rhizopus arrhizus* |
| Rostratum leaf spot (Helminthosporium leaf disease, ear and stalk rot) | *Setosphaeria rostrata*, (anamorph: *Exserohilum rostratum* = *Helminthosporium rostratum*) |
| Rust, common corn | *Puccinia sorghi* |
| Rust, southern corn | *Puccinia polysora* |
| Rust, tropical corn | *Physopella pallescens*, *P. zeae* = *Angiopsora zeae* |
| Sclerotium ear rot* (southern blight) | *Sclerotium rolfsii* Sacc. (teleomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicillatum*, *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| Selenophoma leaf spot* | *Selenophoma* sp. |
| Sheath rot | *Gaeumannomyces graminis* |
| Shuck rot | *Myrothecium gramineum* |
| Silage mold | *Monascus purpureus*, *M. ruber* |
| Smut, common | *Ustilago zeae* = *U. maydis*) |
| Smut, false | *Ustilaginoidea virens* |
| Smut, head | *Sphacelotheca reiliana* = *Sporisorium holcisorghi* |
| Southern corn leaf blight and stalk rot | *Cochliobolus heterostrophus* (anamorph: *Bipolaris maydis* = *Helminthosporium maydis*) |
| Southern leaf spot | *Stenocarpella macrospora* = *Diplodia macrospora* |
| Stalk rots, minor | *Cercospora sorghi*, *Fusarium episphaeria*, *F. merismoides*, *F. oxysporum* Schlechtend, *F. poae*, *F. roseum*, *F. solani* (teleomorph: *Nectria haematococca*), *F. tricinctum*, *Mariannaea elegans*, *Mucor* sp., *Rhopographus zeae*, *Spicaria* sp. |
| Storage rots | *Aspergillus* spp., *Penicillium* spp. and other fungi |
| Tar spot* | *Phyllachora maydis* |
| Trichoderma ear rot and root rot | *Trichoderma viride* = *T. lignorum* teleomorph: *Hypocrea* sp. |
| White ear rot, root and stalk rot | *Stenocarpella maydis* = *Diplodia zeae* |
| Yellow leaf blight | *Ascochyta ischaemi*, *Phyllosticta maydis* (teleomorph: *Mycosphaerella zeae-maydis*) |
| Zonate leaf spot | *Gloeocercospora sorghi* |

*Not known to occur naturally on corn in the United States.

Plant parasitic nematodes are a cause of disease in many plants, including maize. It is proposed that it would be possible to make plants resistant to these organisms through the expression of novel gene products. It is anticipated that control of nematode infestations would be accomplished by altering the ability of the nematode to recognize or attach to a host plant and/or enabling the plant to produce nematicidal compounds, including but not limited to proteins. It is known that certain endotoxins derived from *Bacillus thuringiensis* are nematicidal (Bottjer et al., 1985; U.S. Pat. No. 5,831,011). Examples of nematode-associated plant diseases, for which one could introduce resistance to in a transgenic plant in accordance with the invention are given below, in Table 6.

TABLE 6

Parasitic Nematodes

| DISEASE | PATHOGEN |
| --- | --- |
| Awl | Dolichodorus spp., *D. heterocephalus* |
| Bulb and stem (Europe) | *Ditylenchus dipsaci* |
| Burrowing | *Radopholus similis* |
| Cyst | *Heterodera avenae, H. zeae, Punctodera chalcoensis* |
| Dagger | Xiphinema spp., *X. americanum, X. mediterraneum* |
| False ro0ot-knot | *Nacobbus dorsalis* |
| Lance, Columbia | *Hoplolaimus columbus* |
| Lance | Hoplolaimus spp., *H. galeatus* |
| Lesion | Pratylenchus spp., *P. brachyurus, P. crenatus, P. hexincisus, P. neglectus, P. penetrans, P. scribneri, P. thornei, P. zeae* |
| Needle | Longidorus spp., *L. breviannulatus* |
| Ring | Criconemella spp., *C. ornata* |
| Root-knot | Meloidogyne spp., *M. chitwoodi, M. incognita, M. javanica* |
| Spiral | Helicotylenchus spp. |
| Sting | Belonolaimus spp., *B. longicaudatus* |
| Stubby-root | Paratrichodorus spp., *P. christiei, P. minor, Quinisulcius acutus,* Trichodorus spp. |
| Stunt | *Tylenchorhynchus dubius* |

E. Mycotoxin Reduction/Elimination

Production of mycotoxins, including aflatoxin and fumonisin, by fungi associated with monocotyledonous plants such as maize is a significant factor in rendering the grain not useful. These fungal organisms do not cause disease symptoms and/or interfere with the growth of the plant, but they produce chemicals (mycotoxins) that are toxic to animals. It is contemplated that inhibition of the growth of these fungi would reduce the synthesis of these toxic substances and therefore reduce grain losses due to mycotoxin contamination. It also is proposed that it may be possible to introduce novel genes into monocotyledonous plants such as maize that would inhibit synthesis of the mycotoxin. Further, it is contemplated that expression of a novel gene which encodes an enzyme capable of rendering the mycotoxin nontoxic would be useful in order to achieve reduced mycotoxin contamination of grain. The result of any of the above mechanisms would be a reduced presence of mycotoxins on grain.

F. Grain Composition or Quality

Genes may be introduced into monocotyledonous plants, particularly commercially important cereals such as maize, to improve the grain for which the cereal is primarily grown. A wide range of novel transgenic plants produced in this manner may be envisioned depending on the particular end use of the grain.

The largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes, but in no way provide an exhaustive list of possibilities.

The protein of cereal grains including maize is suboptimal for feed and food purposes especially when fed to monogastric animals such as pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after corn is supplemented with other inputs for feed formulations. For example, when corn is supplemented with soybean meal to meet lysine requirements methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, direct the storage of amino acids in proteins comprising a nutritionally enhanced balance of amino acids, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway which are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyze steps in the catabolic pathways such as the enzyme lysine-ketoglutarate reductase. It is anticipated that it may be desirable to target expression of genes relating to amino acid biosynthesis to the endosperm or embryo of the seed. More preferably, the gene will be targeted to the embryo. It will also be preferable for genes encoding proteins involved in amino acid biosynthesis to target the protein to a plastid using a plastid transit peptide sequence.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. Examples may include the introduction of DNA that decreases the expression of members of the zein family of storage proteins. This DNA may encode ribozymes or antisense sequences directed to impairing expression of zein proteins or expression of regulators of zein expression such as the opaque-2 gene product. It also is proposed that the protein composition of the grain may be modified through the phenomenon of co-suppression, i.e., inhibition of expression of an endogenous gene through the expression of an identical structural gene or gene fragment introduced through transformation (Goring et al., 1991; PCT Publication WO 98/26064). Additionally, the introduced DNA may encode enzymes which degrade zeins. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD delta zein or 20 kD delta zein or 27 kD gamma zein of maize and a promoter or other regulatory sequence designed to elevate expression of said protein. The coding sequence of the gene may include additional or replacement codons for essential amino acids. Further, a coding sequence obtained from another species, or, a partially or completely synthetic sequence encoding a completely unique peptide sequence designed to enhance the amino acid composition of the seed may be employed. It is anticipated that it may be preferable to target expression of these transgenes encoding proteins with superior composition to the endosperm of the seed.

The introduction of genes that alter the oil content of the grain may be of value. Increases in oil content may result in increases in metabolizable-energy-content and density of the seeds for use in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, β-ketoacyl-ACP synthase, plus other well known fatty acid biosynthetic activities. Other possibilities are genes that encode proteins that do not possess enzymatic activity such as acyl carrier protein. Genes may be introduced that alter the balance of fatty acids present in the oil providing a more healthful or nutritive feedstuff. The introduced DNA also may encode sequences that block expression of enzymes involved in fatty acid biosynthesis, altering the proportions of fatty acids present in the grain such as described below. Some other examples of genes specifically contemplated by the inventors for use in creating transgenic plants with altered oil composition traits include 2-acetyltransferase, oleosin, pyruvate dehydrogenase complex, acetyl CoA synthetase, ATP citrate lyase, ADP-glucose pyrophosphorylase and genes of the carnitine-CoA-acetyl-CoA shuttles. It is anticipated that expression of genes related to oil biosynthesis will be targeted to the plastid, using a plastid transit peptide sequence and preferably expressed in the seed embryo.

Genes may be introduced that enhance the nutritive value of the starch component of the grain, for example by increasing the degree of branching, resulting in improved utilization of the starch, for example, in cows by delaying its metabolism. It is contemplated that alteration of starch structure may improve the wet milling properties of grain or may produce a starch composition with improved qualities for industrial utilization. It is anticipated that expression of genes related to starch biosynthesis will preferably be targeted to the endosperm of the seed.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA which blocks or eliminates steps in pigment production pathways.

Most of the phosphorous content of the grain is in the form of phytate, a form of phosphate storage that is not metabolized by monogastric animals. Therefore, in order to increase the availability of seed phosphate, it is anticipated that one will desire to decrease the amount of phytate in seed and increase the amount of free phosphorous. It is anticipated that one can decrease the expression or activity of one of the enzymes involved in the synthesis of phytate. For example, suppression of expression of the gene encoding inositol phosphate synthetase (INOPS) may lead to an overall reduction in phytate accumulation. It is anticipated that antisense or sense suppression of gene expression may be used. Alternatively, one may express a gene in corn seed which will be activated, e.g., by pH, in the gastric system of a monogastric animal and will release phosphate from phytate, e.g., phytase. It is further contemplated that one may provide an alternate storage form for phosphate in the grain, wherein the storage form is more readily utilized by a monogastric animal.

Feed or food comprising primarily maize or other cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like. Maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase which enhances phytic acid breakdown. These genes would increase levels of available phosphate in the diet, reducing the need for supplementation with mineral phosphate.

Numerous other examples of improvement of maize or other cereals for feed and food purposes might be described. The improvements may not even necessarily involve the grain, but may, for example, improve the value of the corn for silage. Introduction of DNA to accomplish this might include sequences that alter lignin production such as those that result in the "brown midrib" phenotype associated with superior feed value for cattle.

In addition to direct improvements in feed or food value, genes also may be introduced which improve the processing of corn and improve the value of the products resulting from the processing. The primary method of processing corn is via wetmilling. Maize may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, rheological properties, and the like. To accomplish these changes in properties, genes that encode granule-bound or soluble starch synthase activity or branching enzyme activity may be introduced alone or in combination. DNA such as antisense constructs also may be used to decrease levels of endogenous activity of these enzymes. The introduced genes or constructs may possess regulatory sequences that time their expression to specific intervals in starch biosynthesis and starch granule development. Furthermore, it may be worthwhile to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn, the value of which may be improved by introduction and expression of genes. The quantity of oil that can be extracted by wetmilling may be elevated by approaches as described for feed and food above. Oil properties also may be altered to improve its performance in the production and use of cooking oil, shortenings, lubricants or other oil-derived products or improvement of its health attributes when used in the food-related applications. Novel fatty acids also may be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively, DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids. Another example is the blockage of elongation steps resulting in the accumulation of $C_8$ to $C_{12}$ saturated fatty acids.

Improvements in the other major corn wetmilling products, corn gluten meal and corn gluten feed, also may be achieved by the introduction of genes to obtain novel corn plants. Representative possibilities include but are not limited to those described above for improvement of food and feed value.

In addition, it may further be considered that the corn plant be used for the production or manufacturing of useful biological compounds that were either not produced at all, or not produced at the same level, in the corn plant previously. The novel corn plants producing these compounds are made possible by the introduction and expression of genes by corn transformation methods. The vast array of possibilities include but are not limited to any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, and industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance γ-zein synthesis, popcorn with improved popping quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken 1 gene (encoding sucrose synthase) or shrunken 2 gene (encoding ADPG pyrophosphorylase) for sweet corn.

G. Plant Agronomic Characteristics

Two of the factors determining where crop plants can be grown are the average daily temperature during the growing season and the length of time between frosts. Within the areas where it is possible to grow a particular crop, there are varying limitations on the maximal time the crop has available to grow to maturity and be harvested. For example, maize to be grown in a particular area is selected for its ability to mature and dry down to harvestable moisture content within the required period of time with maximum possible yield. Therefore, corn of varying maturities is developed for different growing locations. Apart from the need to dry down sufficiently to permit harvest, it is desirable to have maximal drying take place in the field to minimize the amount of energy required for additional post-harvest drying. Also, the more readily the grain can dry down, the more time there is available for growth and seed maturation. It is considered that genes that influence maturity and/or dry down can be identified and introduced into corn or other plants using transformation techniques to create new varieties adapted to different growing locations or the same growing location, but having improved yield to moisture ratio at harvest. Expression of genes that are involved in regulation of plant development may be especially useful, e.g., the liguleless and rough sheath genes that have been identified in corn.

It is contemplated that genes may be introduced into plants that would improve standability and other plant growth characteristics. Expression of novel genes in maize which confer stronger stalks, improved root systems, or prevent or reduce ear droppage would be of great value to the farmer. It is proposed that introduction and expression of genes that increase the total amount of photoassimilate available by, for example, increasing light distribution and/or interception would be advantageous. In addition, the expression of genes that increase the efficiency of photosynthesis and/or the leaf canopy would further increase gains in productivity. It is contemplated that expression of a phytochrome gene in corn may be advantageous. Expression of such a gene may reduce apical dominance, confer semi-dwarfism on a plant, and increase shade tolerance (U.S. Pat. No. 5,268,526). Such approaches would allow for increased plant populations in the field.

Delay of late season vegetative senescence would increase the flow of assimilate into the grain and thus increase yield. It is proposed that overexpression of genes within corn that are associated with "stay green" or the expression of any gene that delays senescence would be advantageous. For example, a nonyellowing mutant has been identified in *Festuca pratensis* (Davies et al., 1990). Expression of this gene as well as others may prevent premature breakdown of chlorophyll and thus maintain canopy function.

H. Nutrient Utilization

The ability to utilize available nutrients may be a limiting factor in growth of monocotyledonous plants such as maize. It is proposed that it would be possible to alter nutrient uptake, tolerate pH extremes, mobilization through the plant, storage pools, and availability for metabolic activities by the introduction of novel genes. These modifications would allow a plant such as maize to more efficiently utilize available nutrients. It is contemplated that an increase in the activity of, for example, an enzyme that is normally present in the plant and involved in nutrient utilization would increase the availability of a nutrient. An example of such an enzyme would be phytase. It further is contemplated that enhanced nitrogen utilization by a plant is desirable. Expression of a glutamate dehydrogenase gene in corn, e.g., *E. coli* gdhA genes, may lead to increased fixation of nitrogen in organic compounds. Furthermore, expression of gdhA in corn may lead to enhanced resistance to the herbicide glufosinate by incorporation of excess ammonia into glutamate, thereby detoxifying the ammonia. It also is contemplated that expression of a novel gene may make a nutrient source available that was previously not accessible, e.g., an enzyme that releases a component of nutrient value from a more complex molecule, perhaps a macromolecule.

I. Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani et al., 1990).

A number of mutations were discovered in maize that confer cytoplasmic male sterility. One mutation in particular, referred to as T cytoplasm, also correlates with sensitivity to Southern corn leaf blight. A DNA sequence, designated TURF-13 (Levings, 1990), was identified that correlates with T cytoplasm. It is proposed that it would be possible through the introduction of TURF-13 via transformation, to separate male sterility from disease sensitivity. As it is necessary to be able to restore male fertility for breeding purposes and for grain production, it is proposed that genes encoding restoration of male fertility also may be introduced.

J. Negative Selectable Markers

Introduction of genes encoding traits that can be selected against may be useful for eliminating undesirable linked genes. It is contemplated that when two or more genes are introduced together by cotransformation, that the genes will be linked together on the host chromosome. For example, a gene encoding Bt that confers insect resistance on the plant may be introduced into a plant together with an EPSPS encoding gene that is useful as a selectable marker and confers resistance to the herbicide glyphosate on the plant. However, it may not be desirable to have an insect resistant plant that also is resistant to the herbicide glyphosate. It is proposed that one also could introduce an antisense sequence specific to the glyphosate resistant EPSPS coding region that is expressed in those tissues where one does not want expression of the EPSPS gene product, e.g., in whole plant parts. Hence, although the EPSPS gene is expressed and is useful as a selectable marker, it is not useful to confer herbicide resistance on the whole plant. The EPSPS antisense gene is a negative selectable marker.

It also is contemplated that negative selection is necessary in order to screen a population of transformants for rare homologous recombinants generated through gene targeting. For example, a homologous recombinant may be identified through the inactivation of a gene that was previously expressed in that cell. The antisense construct for neomycin phosphotransferase II (NPT II) has been investigated as a negative selectable marker in tobacco (*Nicotiana tabacum*) and *Arabidopsis thaliana* (Xiang and Guerra, 1993). In this example, both sense and antisense NPT II genes are introduced into a plant through transformation and the resultant plants are sensitive to the antibiotic kanamycin. An introduced gene that integrates into the host cell chromosome at the site of the antisense NPT II gene, and inactivates the antisense gene, will make the plant resistant to kanamycin and other aminoglycoside antibiotics. Therefore, rare, site-specific recombinants may be identified by screening for antibiotic resistance. The site-directed integration methodology of the current invention may facilitate this gene replacement strategy in planta. Similarly, any gene, native to the plant or introduced through transformation, that when inactivated confers resistance to a compound, may be useful as a negative selectable marker.

It is contemplated that negative selectable markers also may be useful in other ways. One application is to construct transgenic lines in which one could select for transposition to unlinked sites. In the process of tagging it is most common for the transposable element to move to a genetically linked site on the same chromosome. A selectable marker for recovery of rare plants in which transposition has occurred to an unlinked locus would be useful. For example, the enzyme cytosine deaminase may be useful for this purpose. In the presence of this enzyme the non-phytotoxic compound 5-fluorocytosine is converted to 5-fluorouracil which is toxic to plant and animal cells. If a transposable element is linked to the gene for the enzyme cytosine deaminase, one may select for transposition to unlinked sites by selecting for transposition events in which the resultant plant is now resistant to 5-fluorocytosine. The parental plants and plants containing transpositions to linked sites will remain sensitive to 5-fluorocytosine. Resistance to 5-fluorocytosine is due to loss of the cytosine deaminase gene through genetic segregation of the transposable element and the cytosine deaminase gene. Other genes that encode proteins that render the plant sensitive to a certain compound will also be useful in this context. For example, T-DNA gene 2 from *Agrobacterium tumefaciens* encodes a protein that catalyzes the conversion of α-naphthalene acetamide (NAM) to α-naphthalene acetic acid (NAA) renders plant cells sensitive to high concentrations of NAM (Depicker et al., 1988). Also, the pch gene catalyzes the conversion of glyceryl glyphosate to glyphosate thereby rendering cells sensitive to glyceryl glyphosate (U.S. Pat. No. 5,254,801).

It also is contemplated that negative selectable markers may be useful in the construction of transposon tagging lines. For example, by marking an autonomous transposable element such as Ac, Mu, or En/Spn with a negative selectable marker, one could select for transformants in which the autonomous element is not stably integrated into the genome. It is proposed that this would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

K. Non-Protein-Expressing Sequences

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes. However, as detailed below, DNA need not be expressed to effect the phenotype of a plant.

1. Antisense RNA

Genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

2. Ribozymes

Genes also may be constructed or isolated, which when transcribed, produce RNA enzymes (ribozymes) which can act as endoribonucleases and catalyze the cleavage of RNA molecules with selected sequences. The cleavage of selected messenger RNAs can result in the reduced production of their encoded polypeptide products. These genes may be used to prepare novel transgenic plants which possess them. The transgenic plants may possess reduced levels of polypeptides including, but not limited to, the polypeptides cited above.

Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes.

Several different ribozyme motifs have been described with RNA cleavage activity (Symons, 1992). Examples include sequences from the Group I self splicing introns including Tobacco Ringspot Virus (Prody et al., 1986), Avocado Sunblotch Viroid (Palukaitis et al., 1979; Symons, 1981), and Lucerne Transient Streak Virus (Forster and Symons, 1987). Sequences from these and related viruses are referred to as hammerhead ribozyme based on a predicted folded secondary structure.

Other suitable ribozymes include sequences from RNase P with RNA cleavage activity (Yuan et al., 1992, Yuan and Altman, 1994, U.S. Pat. Nos. 5,168,053 and 5,624,824), hairpin ribozyme structures (Berzal-Herranz et al., 1992; Chowrira et al., 1993) and hepatitis delta virus based ribozymes (U.S. Pat. No. 5,625,047). The general design and optimization of ribozyme directed RNA cleavage activity has been discussed in detail (Haseloff and Gerlach, 1988, Symons, 1992, Chowrira et al., 1994; Thompson et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A,C or U) (Perriman et al., 1992; Thompson et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in down regulating a given gene is simply a matter of preparing and testing a given sequence, and is a routinely practiced "screening" method known to those of skill in the art.

3. Induction of Gene Silencing

It also is possible that genes may be introduced to produce novel transgenic plants which have reduced expression of a native gene product by the mechanism of co-suppression. It has been demonstrated in tobacco, tomato, petunia, and corn (Goring et al., 1991; Smith et al., 1990; Napoli et al., 1990; van der Krol et al., 1990; PCT Publication WO 98/26064) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

4. Non-RNA-Expressing Sequences

DNA elements including those of transposable elements such as Ds, Ac, or Mu, may be inserted into a gene to cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer target sequence together with PCR gene cloning techniques (Shapiro, 1983; Dellaporta et al., 1988). Once identified, the entire gene(s) for the particular trait, including control or regulatory regions where desired, may be isolated, cloned and manipulated as desired. The utility of DNA elements introduced into an organism for purposes of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element which may be introduced is a matrix attachment region element (MAR), such as the chicken lysozyme A element (Stief et al., 1989), which can be positioned around an expressible gene of interest to effect an increase in overall expression of the gene and diminish position dependent effects upon incorporation into the plant genome (Stief et al., 1989; Phi-Van et al., 1990).

V. Assays of Transgene Expression

A variety of assays may be employed with the instant invention for determination of the relative efficiency of transgene expression. For example, assays may be used to determine the level of RNA expression of the selected sequence or sequences in the transformed host. Alternatively, assays may be used to determine the level of protein expression of the selected sequence or sequences in the transformed host. One could also carry out assays to determine the efficacy of a given promoter in directing protein expression when used in conjunction with various different enhancers, 3'UTRs or other types of elements which may be used in the preparation of transformation-ready circular molecules or other constructs or vectors.

For plants, expression assays may comprise a system utilizing embryogenic or non-embryogenic cells, or alternatively, whole plants. An advantage of using cellular assays is that regeneration of large numbers of plants is not required. However, the systems are limited in that promoter activity in the non-regenerated cells may not directly correlate with expression in a plant. Additionally, assays of tissue or developmental specific promoters may not be possible.

The biological sample to be assayed may comprise nucleic acids isolated from the cells of any plant material according to standard methodologies (Sambrook and Russell, 2001; Ausubel et al., 2001). The nucleic acid may be genomic DNA or fractionated or whole cell RNA. Where RNA is used, it may be desired to convert the RNA to a complementary DNA. In one embodiment of the invention, the RNA is whole cell RNA; in another, it is poly-$A^+$RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given plant with a statistically significant reference group of non-transformed control plants. Typically, the non-transformed control plants will be of a genetic background similar to the transformed plants. In this way, it is possible to detect differences in the amount or kind of protein detected in various transformed plants. Alternatively, clonal cultures of cells, for example, callus or an immature embryo, may be compared to other cells samples.

As indicated, a variety of different assays are contemplated in the screening of cells or plants of the current invention and associated promoters. These techniques may in cases be used to detect for both the presence and expression of the particular genes as well as rearrangements that may have occurred in the gene construct. The techniques include but are not limited to, fluorescent in situ hybridization (FISH), direct DNA sequencing, pulsed field gel electrophoresis (PFGE) analysis, Southern or Northern blotting, single-stranded conformation analysis (SSCA), RNase protection assay, allele-specific oligonucleotide (ASO), dot blot analysis, denaturing gradient gel electrophoresis, RFLP and PCR-SSCP.

A. Quantitation of Gene Expression with Relative Quantitative RT-PCR

Reverse transcription (RT) of RNA to cDNA followed by relative quantitative PCR (RT-PCR) can be used to determine the relative concentrations of specific mRNA species isolated from plants. By determining that the concentration of a specific mRNA species varies, it is shown that the gene encoding the specific mRNA species is differentially expressed. In this way, a promoter's expression profile can be rapidly identified, as can the efficacy with which the promoter directs transgene expression. Similarly, the expression profiles of a number of genomic target sites can be identified and compared to allow for selection of target sites with the most desirable expression characteristics. It is contemplated that RT-PCR may be quantitated using TaqMan™ methods (Applied Biosystems, Foster City, Calif.).

In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of an mRNA species can be determined by RT-PCR for a collection of RNA populations is that the concentrations of the amplified PCR products must be sampled when the PCR reactions are in the linear portion of their curves.

The second condition that must be met for an RT-PCR study to successfully determine the relative abundances of a particular mRNA species is that relative concentrations of the amplifiable cDNAs must be normalized to some independent standard. The goal of an RT-PCR study is to determine the abundance of a particular mRNA species relative to the average abundance of all mRNA species in the sample.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for plant tissue. The problems inherent in plant tissue samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR product in the linear range of the amplification curve, thus increasing the sensitivity of the assay. Another reason is that with only one PCR product, display of the product on an electrophoretic gel or another display method becomes less complex, has less background and is easier to interpret.

B. Marker Gene Expression

Marker genes represent an efficient means for assaying the expression of transgenes. Using, for example, a selectable marker gene, one could quantitatively determine the resistance conferred upon a plant or plant cell by a construct comprising the selectable marker coding region operably linked to the promoter to be assayed. Alternatively, various plant parts could be exposed to a selective agent and the relative resistance provided in these parts quantified, thereby providing an estimate of the tissue specific expression of the promoter.

Screenable markers constitute another efficient means for quantifying the expression of a given transgene. Potentially any screenable marker could be expressed and the marker gene product quantified, thereby providing an estimate of the efficiency with which the promoter directs expression of the transgene. Quantification can readily be carried out using either visual means, or, for example, a photon counting device.

A preferred screenable marker gene assay for use with the current invention constitutes the use of the screenable marker gene β-glucuronidase (Jefferson et al., 1986; uidA gene; the product of which is commonly referred to as GUS). Detection of GUS activity can be performed histochemically using 5-bromo-4-chloro-3-indolyl glucuronide (X-gluc) as the substrate for the GUS enzyme, yielding a blue precipitate inside of cells containing GUS activity. This assay has been described in detail (Jefferson, 1987). The blue coloration can then be visually scored, and estimates of expression efficiency thereby provided. GUS activity also can be determined by immunoblot analysis or a fluorometric GUS specific activity assay (Jefferson, 1987).

C. Purification and Assays of Proteins

One means for determining the efficiency with which a particular transgene is expressed is to purify and quantify a polypeptide expressed by the transgene. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; and isoelectric focusing. A particularly efficient method of purifying peptides is fast protein liquid chromatography or even HPLC.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide being assayed always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

VI. Methods for Plant Transformation

Suitable methods for plant transformation for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No.5,302,523, specifically incorporated herein by reference in its entirety; and U.S. Pat. No. 5,464,765, specifically incorporated herein by reference in its entirety), by *Agrobacterium*-mediated transformation (U.S.

Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety). Through the application of techniques such as these, maize cells as well as those of virtually any other plant species may be stably transformed, and these cells developed into fertile transgenic plants. In certain embodiments, acceleration methods are preferred and include, for example, microprojectile bombardment and the like.

A. Electroporation

Where one wishes to introduce DNA by means of electroporation, it is contemplated that the method of Krzyzek et al. (U.S. Pat. No. 5,384,253, incorporated herein by reference in its entirety) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in PCT Publication WO 92/17598 (specifically incorporated herein by reference). Other examples of species for which protoplast transformation has been described include barley (Lazerri, 1995), sorghum (Battraw and Hall, 1991), maize (Bhattacharjee et al., 1997), wheat (He et al., 1994) and tomato (Tsukada, 1989).

B. Microprojectile Bombardment

A preferred method for delivering transforming DNA segments to plant cells in accordance with the invention is microprojectile bombardment (U.S. Pat. Nos. 5,550,318; 5,538,880; 5,610,042; and PCT Publication WO 95/06128; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells, such as callus tissue, may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

For microprojectile bombardment, one will attach (i.e., "coat") DNA to the microprojectiles such that it is delivered to recipient cells in a form suitable for transformation thereof In this respect, at least some of the transforming DNA must be available to the target cell for transformation to occur, while at the same time during delivery the DNA must be attached to the microprojectile. Therefore, availability of the transforming DNA from the microprojectile may comprise the physical reversal of bonds between transforming DNA and the microprojectile following delivery of the microprojectile to the target cell. This need not be the case, however, as availability to a target cell may occur as a result of breakage of unbound segments of DNA or of other molecules which comprise the physical attachment to the microprojectile. Availability may further occur as a result of breakage of bonds between the transforming DNA and other molecules, which are either directly or indirectly attached to the microprojectile. It further is contemplated that transformation of a target cell may occur by way of direct recombination between the transforming DNA and the genomic DNA of the recipient cell. Therefore, as used herein, a "coated" microprojectile will be one which is capable of being used to transform a target cell, in that the transforming DNA will be delivered to the target cell, yet will be accessible to the target cell such that transformation may occur.

Any technique for coating microprojectiles which allows for delivery of transforming DNA to the target cells may be used. Methods for coating microprojectiles which have been demonstrated to work well with the current invention have been specifically disclosed herein. DNA may be bound to microprojectile particles using alternative techniques, however. For example, particles may be coated with streptavidin and DNA end labeled with long chain thiol cleavable biotinylated nucleotide chains. The DNA adheres to the particles due to the streptavidin-biotin interaction, but is released in the cell by reduction of the thiol linkage through reducing agents present in the cell.

Alternatively, particles may be prepared by functionalizing the surface of a gold oxide particle, providing free amine groups. DNA, having a strong negative charge, binds to the functionalized particles. Furthermore, charged particles may be deposited in controlled arrays on the surface of mylar flyer disks used in the PDS-1000 Biolistics device, thereby facilitating controlled distribution of particles delivered to target tissue.

As disclosed above, it further is proposed, that the concentration of DNA used to coat microprojectiles may influence the recovery of transformants containing a single copy of the transgene. For example, a lower concentration of DNA may not necessarily change the efficiency of the transformation, but may instead increase the proportion of single copy insertion events. In this regard, approximately 1 ng to 2000 ng of transforming DNA may be used per each 1.8 mg of starting microprojectiles. In other embodiments of the invention, approximately 2.5 ng to 1000 ng, 2.5 ng to 750 ng, 2.5 ng to 500 ng, 2.5 ng to 250 ng, 2.5 ng to 100 ng, or 2.5 ng to 50 ng of transforming DNA may be used per each 1.8 mg of starting microprojectiles.

Microprojectile bombardment techniques are widely applicable, and may be used to transform virtually any plant species. Examples of species for which have been transformed by microprojectile bombardment include monocot species such as maize (PCT Publication WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (Van Eck et al. 1995), and legumes in general (U.S. Pat. No. 5,563,055, specifically incorporated herein by reference in its entirety).

For microprojectile bombardment transformation in accordance with the current invention, both physical and biological parameters may be optimized. Physical factors are those that involve manipulating the DNA/microprojectile precipitate or those that affect the flight and velocity of either the macro- or microprojectiles. Biological factors include all steps involved in manipulation of cells before and immediately after bombardment, such as the osmotic adjustment of target cells to help alleviate the trauma associated with bombardment, the orientation of an immature embryo or other target tissue relative to the particle trajectory, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as DNA concentration, gap distance, flight distance, tissue distance, and helium pressure. It further is contemplated that the grade of helium may effect transformation efficiency. One also may optimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation.

C. Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cell are punctured. This technique has been used successfully with, for example, the monocot cereals maize (PCT Publication WO 95/06128, specifically incorporated herein by reference in its entirety; Thompson, 1995) and rice (Nagatani, 1997).

VII. Recipient Cells for Transformation

Tissue culture requires media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid. Table 7 illustrates the composition of various media useful for creation of recipient cells and for plant regeneration.

Recipient cell targets include, but are not limited to, meristem cells, Type I, Type II, and Type III callus, immature embryos and gametic cells such as microspores, pollen, sperm and egg cells. It is contemplated that any cell from which a fertile plant may be regenerated is useful as a recipient cell. Type I, Type II, and Type III callus may be initiated from tissue sources including, but not limited to, immature embryos, seedling apical meristems, microspores and the like. Those cells which are capable of proliferating as callus also are recipient cells for genetic transformation. The present invention provides techniques for transforming immature embryos and subsequent regeneration of fertile transgenic plants. Transformation of immature embryos obviates the need for long term development of recipient cell cultures. Pollen, as well as its precursor cells, microspores, may be capable of functioning as recipient cells for genetic transformation, or as vectors to carry foreign DNA for incorporation during fertilization. Direct pollen transformation would obviate the need for cell culture. Meristematic cells (i.e., plant cells capable of continual cell division and characterized by an undifferentiated cytological appearance, normally found at growing points or tissues in plants such as root tips, stem apices, lateral buds, etc.) may represent another type of recipient plant cell. Because of their undifferentiated growth and capacity for organ differentiation and totipotency, a single transformed meristematic cell could be recovered as a whole transformed plant.

Cultured plant cells that can serve as recipient cells for transforming with desired DNA segments may be any plant cells including corn cells, and more specifically, cells from *Zea mays* L. Somatic cells are of various types. Embryogenic cells are one example of somatic cells which may be induced to regenerate a plant through embryo formation. Non-embryogenic cells are those which typically will not respond in such a fashion. An example of non-embryogenic cells are certain Black Mexican Sweet (BMS) corn cells.

The development of embryogenic maize calli and suspension cultures useful in the context of the present invention, e.g., as recipient cells for transformation, has been described in U.S. Pat. Nos. 5,134,074; 5,489,520; and PCT Publication WO 95/06128 each of which is incorporated herein by reference in its entirety.

Certain techniques may be used that enrich recipient cells within a cell population. For example, Type II callus development, followed by manual selection and culture of friable, embryogenic tissue, generally results in an enrichment of recipient cells for use in, microprojectile transformation. Manual selection techniques which can be employed to select recipient cells may include, e.g., assessing cell morphology and differentiation, or may use various physical or biological means.

Manual selection of recipient cells, e.g., by selecting embryogenic cells from the surface of a Type II callus, is one means that may be used in an attempt to enrich for recipient cells prior to culturing (whether cultured on solid media or in suspension). The preferred cells may be those located at the surface of a cell cluster, and may further be identifiable by their lack of differentiation, their size and dense cytoplasm. The preferred cells will generally be those cells which are less differentiated, or not yet committed to differentiation. Thus, one may wish to identify and select those cells which are cytoplasmically dense, relatively unvacuolated with a high nucleus to cytoplasm ratio (e.g., determined by cytological observations), small in size (e.g., 10–20 µm), and capable of sustained divisions and somatic proembryo formation.

It is proposed that other means for identifying such cells also may be employed. For example, through the use of dyes, such as Evan's blue, which are excluded by cells with relatively non-permeable membranes, such as embryogenic cells, and taken up by relatively differentiated cells such as root-like cells and snake cells (so-called due to their snake-like appearance).

Other possible means of identifying recipient cells include the use of isozyme markers of embryogenic cells, such as glutamate dehydrogenase, which can be detected by cytochemical stains (Fransz et al., 1989). However, it is cautioned that the use of isozyme markers including glutamate dehydrogenase may lead to some degree of false positives from non-embryogenic cells such as rooty cells which nonetheless have a relatively high metabolic activity.

A. Culturing Cells to be Recipients for Transformation

A variety of different types of media have been previously developed and may be employed in carrying out various aspects of the invention. The following table, Table 7, sets forth the composition of the media preferred by the inventor for carrying out these aspects of the invention. One of skill in the art would realize that a variety of media and supplements added to media may be used to achieve results in keeping with the scope of this invention.

TABLE 7

Plant Tissue Culture Media and Supplements

| MEDIA NO. | BASAL MEDIUM | SUCROSE | pH | OTHER COMPONENTS** (Amount/L) |
|---|---|---|---|---|
| 105 | MS | — | 5.8 | 0.04 mg NAA<br>3 mg BAP<br>1 mg thiamine.HCl<br>0.5 mg nicotinic acid<br>0.91 g/L-asparagine monohydrate<br>100 mg myo-inositol<br>100 mg casein hydrolysate<br>1.4 g L-proline<br>20 g sorbitol<br>2.0 g GELGRO ™ |
| 110 | 0.5 × MS | 6% | 5.8 | 0.5 mg thiamine.HCl<br>0.5 mg niacin<br>3.6 g GELGRO ™ |
| 127 | MS | — | 5.8 | MS salts<br>0.65 mg/L niacin,<br>0.125 mg/L pyridoxine-HCl<br>0.125 mg/L thiamine-HCl<br>0.125 mg/L Ca pantothenate<br>150 mg L-asparagine<br>100 mg myo-inositol<br>10 g glucose<br>20 g L-maltose<br>6 g PHYTAGAR ™ |
| 201 | N6 | 2% | 5.8 | N6 vitamins<br>2 mg/L-glycine<br>1 mg/L 2,4-D<br>100 mg casein hydrolysate<br>2.9 g L-proline<br>2 g GELGRO ™ |
| 211 | N6 | 2% | 5.8 | 1 mg 2,4-D<br>0.5 mg nicotinic acid<br>1.0 mg thiamine<br>0.91 g L-asparagine<br>100 mg myo-inositol<br>0.5 g MES<br>100 mg/L casein hydrolysate<br>1.6 g $MgCl_2$—$6H_2O$<br>0.69 g L-proline<br>2 g GELGRO ™ |
| 217 | N6 | 2% | 5.8 | N6 salts<br>1 mg/L thiamine-HCl<br>0.5 mg/L nicotinic acid<br>3.52 mg/L benzylaminopurine,<br>0.91 g/L L-asparagine monohydrate<br>100 mg/L myo-inositol<br>0.5 g/L MES<br>1.6 g/L $MgCl_2$—$6H_2O$<br>100 mg/L casein hydrolysate<br>0.69 g/L L-proline<br>20 g/L sucrose<br>2 g/L GELGRO ™ |

TABLE 7-continued

Plant Tissue Culture Media and Supplements

| MEDIA NO. | BASAL MEDIUM | SUCROSE | pH | OTHER COMPONENTS** (Amount/L) |
|---|---|---|---|---|
| (media#)EE*** | — | — | — | Media supplemented with 100 mg/L kanamycin |
| (media#)F | — | — | — | Media supplemented with 200 mg/L kanamycin |
| (media#)G | — | — | — | Media supplemented with 50 mg/L paromomycin |
| (media#)H | — | — | — | Media supplemented with 25 mg/L paromomycin |
| (media#)J | — | — | — | Media supplemented with 1 mM glyphosate |
| (media#)K | — | — | — | Media supplemented with 3 mM glyphosate |
| (media#)L | — | — | — | Media supplemented with 500 mg/L paromomycin |
| (media#)S | — | 12% | — | Media supplemented with 12% sucrose |
| (media#)T | — | — | — | Media supplemented with 100 mg/L paromomycin |
| (media#)V | — | — | — | Media supplemented with 16.9 mg/L silver nitrate |

*Basic MS medium described in Murashige and Skoog (1962). This medium is typically modified by decreasing the $NH_4NO_3$ from 1.64 g/l to 1.55 g/l, and omitting the pyridoxine HCl, nicotinic acid, myo-inositol and glycine.
**NAA = Napthol Acetic Acid
2,4-D = 2,4-Dichlorophenoxyacetic Acid
BAP = 6-Benzyl aminopurine
MES = 2-(4-morpholino)-ethane sulfonic acid
***Supplements are assigned a letter code; combination of a media with a supplement appends the supplement letter to the media number. Thus, media #201 containing 16.9 mg/L silver nitrate (code V) is abbreviated #201V.

A number of exemplary maize cultures which may be used for transformation have been developed and are disclosed in PCT publication WO 95/06128, the disclosure of which is specifically incorporated herein by reference.

B. Media

In certain embodiments of the current invention, recipient cells may be selected following growth in culture. Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components (see Table 7), but may differ in the composition and proportions of their ingredients depending on the particular application envisioned. For example, various cell types usually grow in more than one type of media, but will exhibit different growth rates and different morphologies, depending on the growth media. In some media, cells survive but do not divide.

Various types of media suitable for culture of plant cells previously have been described. Examples of these media include, but are not limited to, the N6 medium described by Chu et al. (1975) and MS media (Murashige and Skoog, 1962). It has been discovered that media such as MS which have a high ammonia/nitrate ratio are counterproductive to the generation of recipient cells in that they promote loss of morphogenic capacity. N6 media, on the other hand, has a somewhat lower ammonia/nitrate ratio, and is contemplated to promote the generation of recipient cells by maintaining cells in a proembryonic state capable of sustained divisions.

C. Maintenance

The method of maintenance of cell cultures may contribute to their utility as sources of recipient cells for transformation. Manual selection of cells for transfer to fresh culture medium, frequency of transfer to fresh culture medium, composition of culture medium, and environmental factors including, but not limited to, light quality and quantity and temperature are all important factors in maintaining callus and/or suspension cultures that are useful as sources of recipient cells. It is contemplated that alternating callus between different culture conditions may be beneficial in enriching for recipient cells within a culture. For example, it is proposed that cells may be cultured in suspension culture, but transferred to solid medium at regular intervals. After a period of growth on solid medium cells can be manually selected for return to liquid culture medium. It is proposed that by repeating this sequence of transfers to fresh culture medium it is possible to enrich for recipient cells. It also is contemplated that passing cell cultures through a 1.9 mm sieve is useful in maintaining the friability of a callus or suspension culture and may be beneficial in enriching for transformable cells.

D. Cryopreservation Methods

Cryopreservation is important because it allows one to maintain and preserve a known transformable cell culture for future use, while eliminating the cumulative detrimental effects associated with extended culture periods.

Cell suspensions and callus were cryopreserved using modifications of methods previously reported (Finkle, 1985; Withers and King, 1979). The cryopreservation protocol comprised adding a pre-cooled (0° C.) concentrated cryoprotectant mixture stepwise over a period of one to two hours to pre-cooled (0° C.) cells. The mixture was maintained at 0° C. throughout this period. The volume of added cryoprotectant was equal to the initial volume of the cell suspension (1:1 addition), and the final concentration of cryoprotectant additives was 10% dimethyl sulfoxide, 10% polyethylene glycol (6000 MW), 0.23 M proline and 0.23 M glucose. The mixture was allowed to equilibrate at 0° C. for 30 minutes, during which time the cell suspension/cryoprotectant mixture was divided into 1.5 ml aliquot (0.5 ml packed cell volume) in 2 ml polyethylene cryo-vials. The tubes were cooled at 0.5° C./minute to −8° C. and held at this temperature for ice nucleation.

Once extracellular ice formation had been visually confirmed, the tubes were cooled at 0.5° C./minute from −8° C. to −35° C. They were held at this temperature for 45 minutes (to insure uniform freeze-induced dehydration throughout the cell clusters). At this point, the cells had lost the majority of their osmotic volume (i.e., there is little free water left in the cells), and they could be safely plunged into liquid nitrogen for storage. The paucity of free water remaining in the cells in conjunction with the rapid cooling rates from −35° C. to −196° C. prevented large organized ice crystals from forming in the cells. The cells are stored in liquid nitrogen, which effectively immobilizes the cells and slows metabolic processes to the point where long-term storage should not be detrimental.

Thawing of the extracellular solution was accomplished by removing the cryo-tube from liquid nitrogen and swirling it in sterile 42° C. water for approximately 2 minutes. The tube was removed from the heat immediately after the last ice crystals had melted to prevent heating the tissue. The cell suspension (still in the cryoprotectant mixture) was pipetted onto a filter, resting on a layer of BMS cells (the feeder layer which provided a nurse effect during recovery). The cryoprotectant solution is removed by pipetting. Culture medium comprised a callus proliferation medium with increased osmotic strength. Dilution of the cryoprotectant occurred slowly as the solutes diffused away through the filter and nutrients diffused upward to the recovering cells. Once subsequent growth of the thawed cells was noted, the growing tissue was transferred to fresh culture medium. If initiation of a suspension culture was desired, the cell clusters were transferred back into liquid suspension medium as soon as sufficient cell mass had been regained (usually within 1 to 2 weeks). Alternatively, cells were cultured on solid callus proliferation medium. After the culture was reestablished in liquid (within 1 to 2 additional weeks), it was used for transformation experiments. When desired, previously cryopreserved cultures may be frozen again for storage.

VIII. Production and Characterization of Stably Transformed Plants

After effecting delivery and integration of transformation-ready circular molecules to recipient cells, the next steps generally concern identifying the transformed cells for further culturing and plant regeneration. As mentioned herein, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Transformed cells are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One example of a herbicide which is useful for selection of transformed cell lines in the practice of the invention is the broad spectrum herbicide glyphosate. Glyphosate inhibits the action of the enzyme EPSPS, which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, PCT Publication WO 97/04103. A naturally occurring glyphosate resistant EPSPS may be preferably used, e.g., the CP4 gene isolated from *Agrobacterium* encodes a glyphosate resistant EPSPS (U.S. Pat. No. 5,627,061).

Another example of a herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

To use the bar-bialaphos or the EPSPS-glyphosate selective system, bombarded tissue is cultured for 0–28 days on nonselective medium and subsequently transferred to medium containing from 1–3 mg/l bialaphos or 1–3 mM glyphosate as appropriate. While ranges of 1–3 mg/l bialaphos or 1–3 mM glyphosate will typically be preferred, it is proposed that ranges of 0.1–50 mg/l bialaphos or 0.1–50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

It further is contemplated that the herbicide dalapon, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. Pat. No. 5,780,708).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468 and PCT Publication WO 97/26366.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase may be used as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene (PCT Publication WO 99/60129).

B. Regeneration and Seed Production

Cells that survive the exposure to the selective agent, or cells that have been scored positive in a screening assay, may be cultured in media that supports regeneration of plants. In an exemplary embodiment, MS and N6 media may be modified (see Table 7) by including or removing further substances such as growth regulators. A preferred growth regulator for initiation of plant regeneration is 6-benzylaminopurine. However, other growth regulators may be employed, particularly cytokinins, such as zeatin and kinetin and the like, or abscisic acid. Media improvement in these and like ways has been found to facilitate the growth of cells at specific developmental stages. Tissue may be maintained on a basic media with growth regulators, preferably auxins, until sufficient tissue is available to begin plant regeneration efforts, or following repeated rounds of manual selection, until the morphology of the tissue is suitable for regeneration, then transferred to media conducive to maturation of embryoids. Cultures are transferred approximately every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened off, e.g., in an environmentally controlled chamber at about 85% relative humidity, 600 ppm $CO_2$, and 25–250 microeinsteins $m^{-2}s^{-1}$ of light, prior to transfer to a greenhouse or growth chamber for maturation. Plants are preferably matured either in a growth chamber or greenhouse. Plants are regenerated from about 6 wk to 10 months after a transformant is identified, depending on the initial tissue. During regeneration, cells are grown on solid media in tissue culture vessels. Illustrative embodiments of such vessels are petri dishes, PLANTCONS® (ICN Biomedicals, Inc., Aurora, Ohio) and PHYTATRAYS™ (Sigma Chemicals, St. Louis, Mo.). Regenerating plants are preferably grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10–20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}M$ abscisic acid and then transferred to growth regulator-free medium for germination.

Progeny may be recovered from transformed plants and tested for expression of the exogenous expressible gene by methods known in the art.

C. Characterization

To confirm the presence of the exogenous DNA or "transgene(s)" in the regenerating plants, a variety of assays may be performed. Such assays include, for example, "molecular biological" assays, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

1. DNA Integration, RNA Expression and Inheritance

Genomic DNA may be isolated from callus cell lines or any plant parts to determine the presence of the exogenous gene through the use of techniques well known to those skilled in the art. Note that intact sequences may not always be present, presumably due to rearrangement or deletion of sequences in the cell.

The presence of DNA elements introduced through the methods of this invention may be determined by polymerase chain reaction (PCR). Using this technique discreet fragments of DNA are amplified and detected by gel electrophoresis. This type of analysis permits one to determine whether a gene is present in a stable transformant, but does not prove integration of the introduced gene into the host cell genome. Typically, DNA has been integrated into the genome of all transformants that demonstrate the presence of the gene through PCR analysis.

Positive proof of DNA integration into the host genome and the independent identities of transformants may be determined using the technique of Southern hybridization. Using this technique, specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a gene.

Both PCR and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR techniques also may be used for detection and quantitation of RNA produced from introduced genes. In this application of PCR, or RT-PCR, it is first necessary to reverse transcribe RNA into DNA, using enzymes such as reverse transcriptase, and then, through the use of conventional PCR techniques, amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species. It is contemplated that TAQMan™ methods may be combined with PCR or RT-PCR methods to analyze transgenic cells. Quantitative RT-PCR methods may be employed to determine levels of RNA accumulation in various tissues and/or at varying points in time.

2. Gene Expression

While Southern blotting and PCR may be used to detect the gene(s) in question, they do not provide information as to whether the gene is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following an increase in fluorescence as anthranilate is produced, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

D. Event Specific Transgene Assays

Southern blotting, PCR and RT-PCR techniques can be used to identify the presence or absence of a given transgene but, depending upon experimental design, may not specifically and uniquely identify identical or related transgene constructs located at different insertion points within the recipient genome. To more precisely characterize the presence of transgenic material in a transformed plant, one skilled in the art could identify the point of insertion of the transgene and, using the sequence of the recipient genome flanking the transgene, develop an assay that specifically and uniquely identifies a particular insertion event. Many methods can be used to determine the point of insertion such as, but not limited to, Genome Walker™ technology (CLONTECH, Palo Alto, Calif.), Vectorette™ technology (SIGMA, St. Louis, Mo.), restriction site oligonucleotide PCR (Sarkar et al., 1993; Weber et al., 1998), uneven PCR (Chen and Wu, 1997) and generation of genomic DNA clones containing the transgene of interest in a vector such as, but not limited to, lambda phage.

Once the sequence of the genomic DNA directly adjacent to the transgenic insert on either or both sides has been determined, one skilled in the art can develop an assay to specifically and uniquely identify the insertion event. For example, two oligonucleotide primers can be designed, one wholly contained within the transgene and one wholly contained within the flanking sequence, which can be used together with the PCR technique to generate a PCR product unique to the inserted transgene. In one embodiment, the two oligonucleotide primers for use in PCR could be designed such that one primer is complementary to sequences in both the transgene and adjacent flanking sequence such that said primer spans the junction of the insertion site while the second primer could be homologous to sequences contained wholly within the transgene. In another embodiment, the two oligonucleotide primers for use in PCR could be designed such that one primer is complementary to sequences in both the transgene and adjacent flanking sequence such that said primer spans the junction of the insertion site while the second primer could be homologous to sequences contained wholly within the genomic sequence adjacent to the insertion site. Confirmation of the PCR reaction may be monitored by, but not limited to, size analysis on gel electrophoresis, sequence analysis, hybridization of the PCR product to a specific radiolabeled DNA or RNA probe or to a molecular beacon (Tyagi and Kramer, 1996), or use of the primers in conjugation with a TaqMan™ probe and technology (Applied Biosystems, Foster City, Calif.).

One of skill in the art would recognize that site-directed integration into an insertion site in a genome, such as a lox site, will simplify the development of such event specific transgene assays; once the sequence flanking the target site in the genome is identified, the sequence can be used for developing assays for different DNAs inserted into the target site.

IX. Deletion of Sequences Located within the Transgenic Insert

During the transformation process it is often necessary to include sequences, such as selectable marker or reporter genes, for tracking the presence or absence of a selected trait gene transformed into the plant on the DNA construct. Such sequences, while useful in the generation, monitoring and analysis of a recombination event, often do not contribute to the desired trait or characteristic conferred by the phenotypic trait gene. Homologous recombination is a method by which introduced sequences may be selectively deleted in transgenic plants.

It is known that homologous recombination results in genetic rearrangements of transgenes in plants. Repeated DNA sequences have been shown to lead to deletion of a flanked sequence in various dicot species, e.g. *Arabidopsis thaliana* (Swoboda et al., 1994; Jelesko et al., 1999), *Brassica napus* (Gal et al., 1991; Swoboda et al., 1993) and *Nicotiana tabacum* (Peterhans et al., 1990; Zubko et al., 2000). One of the most widely held models for homologous recombination is the double-strand break repair (DSBR) model (Szostak et al., 1983).

Deletion of sequences by homologous recombination relies upon directly repeated DNA sequences positioned about the region to be excised in which the repeated DNA sequences direct excision utilizing native cellular recombination mechanisms. The first fertile transgenic plants are crossed to produce either hybrid or inbred progeny plants, and from those progeny plants, one or more second fertile transgenic plants are selected which contain a second DNA sequence that has been altered by recombination, preferably resulting in the deletion of ancillary sequences or other undesired sequences. The first fertile plant can be either hemizygous or homozygous for the DNA sequence containing the directly repeated DNA which will drive the recombination event.

The directly repeated sequences are located 5' and 3' to the target sequence in the transgene. As a result of the recombination event, the transgene target sequence may be deleted, amplified or otherwise modified within the plant genome. In the preferred embodiment, a deletion of the target sequence flanked by the directly repeated sequence will result.

An enzymatic recombination system, such as CRE/lox or FLP/frt, is another means of effecting DNA excision known to those of skill in the art. In this case, the sequences to be excised are flanked by lox or frt sites in the same orientation and after contact by CRE or FLP recombinase, respectively, the sequences between the site-specific recombination sites will be deleted.

X. Breeding Plants of the Invention

One of the advantages of the methods of the present invention is that it is possible to achieve site-specific integration of selected DNA sequences without ancillary sequences such as bacterial origins of replication and the like. Therefore, the need to delete sequences via homologous recombination is reduced. In addition to direct transformation of a particular plant genotype with a transformation-ready circular molecule prepared according to the current invention, transgenic plants may be made by crossing a transgenic plant to a second plant lacking the transgenic sequences or to a plant containing different transgene sequences. For example, a selected coding region operably linked to a promoter can be introduced into a particular plant variety by crossing, without the need for ever directly transforming a plant of that given variety. Therefore, the current invention not only encompasses a plant directly regenerated from cells which have been transformed in accordance with the current invention, but also the progeny of such plants. As used herein the term "progeny" denotes the offspring of any generation of a parent plant prepared in accordance with the instant invention, wherein the progeny comprises a construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking said desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring said desired gene, DNA sequence or element from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking said desired DNA sequence may be referred to as an unconverted genotype, line, inbred, or hybrid.

XI. Definitions

Ancillary sequence: A sequence which is not one of the selected sequences desired for transformation into a recipient genome. Ancillary sequences may include, but are not limited to, bacterial origins of replication or associated sequences and antibiotic resistance.

Genetic Transformation: A process of introducing a DNA sequence or construct (e.g., a vector or expression cassette or a transformation-ready circular molecule) into a cell or protoplast in which that exogenous DNA is incorporated into a chromosome or is capable of autonomous replication.

Exogenous gene: A gene which is not normally present in a given host genome in the exogenous gene's present form In this respect, the gene itself may be native to the host genome, however, the exogenous gene will comprise the native gene altered by the addition or deletion of one or more different regulatory elements.

Expression: The combination of intracellular processes, including transcription and translation undergone by a coding DNA molecule such as a structural gene to produce a polypeptide or an RNA product.

Expression cassette: A chimeric, usually linear, DNA molecule which is designed for introduction into a host genome by genetic transformation. Preferred expression cassettes will comprise all of the genetic elements necessary to direct the expression of a selected gene.

Expression unit: Chimeric DNA sequence which comprises genetic elements, including but not limited to a promoter and 3'UTR, and optionally an enhancer element, necessary to direct the expression of a selected coding sequence as well as any sequences needed to direct the encoded protein to the correct subcellular location, e.g., transit and signal peptide encoding sequences.

Expression vector: A vector comprising at least one expression unit or expression cassette.

Non-replicating molecule: A linear or circular molecule, or sequence arrangement, which is not capable of being replicated in a microorganism, such as bacteria and yeast.

Non-mutagenizing oligonucleotide: An oligonucleotide molecule, also called a primer, which is completely complementary to a target sequence; that is, an oligonucleotide used to generate a transformation-ready circular molecule is 100% homologous to the hybridization site on a circular template molecule.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant.

Progeny: Any subsequent generation, including the seeds and plants therefrom, which is derived from a particular parental plant or set of parental plants.

Promoter: A recognition site on a DNA sequence or group of DNA sequences that provides an expression control element for a structural gene and to which RNA polymerase specifically binds and initiates RNA synthesis (transcription) of that gene.

$R_0$ Transgenic Plant: A plant which has been directly transformed with a selected DNA or has been regenerated from a cell or cell cluster which has been transformed with a selected DNA.

Regeneration: The process of growing a plant from a plant cell (e.g., plant protoplast, callus or explant).

Selected DNA: A DNA segment which one desires to introduce into a plant genome by genetic transformation.

Selected Gene: A gene which one desires to have expressed in a transgenic plant, plant cell or plant part. A selected gene may be native or foreign to a host genome, but where the selected gene is present in the host genome, will include one or more regulatory or functional elements which differ from native copies of the gene. A selected gene may include, but is not limited to, genes imparting insect resistance, herbicide resistance, improved agronomic traits, improved quality traits or improved yield, and does not include ancillary sequences.

Selected Sequence: A sequence which one desires to have expressed in a transgenic plant, plant cell or plant part. A selected sequence may be native or foreign to a host genome, but where the selected sequence is present in the host genome, will include one or more regulatory or functional elements which differ from native copies of the sequence. A selected sequence may include, but is not limited to, sequences useful for antisense methodology, or for imparting insect resistance, herbicide resistance, improved agronomic traits, improved quality traits or improved yield, and does not include ancillary sequences.

Source molecules or material: The nucleic acid material which is used to generate the circular template defined above. This may include any type of DNA sequence from which the desired or selected genes or sequences are obtained and used to prepare circular templates.

Starting circular template: A non-replicating, circular nucleic acid molecule which may be single-stranded or double-stranded, which contains the desired or selected DNA sequences of interest and lacks ancillary sequences including, but not limited to, origins of replication. These molecules may be used in a PCR reaction for the preparation of transformation-ready circular molecules of the invention.

Substantially identical: A molecule which is a replicate of a starting template molecule in which non-mutagenizing primers and an amplification process are used to generate the replicated molecule is said to be substantially identical to the starting template, where all changes in the sequence of the copied molecule are the result of errors in the amplification process. Substantially identical molecules may be 90–100% identical, preferably 93–100% identical, more preferably 96–100% identical, even more preferably 98–100% identical and most preferably, 99–100% identical. Substantially identical oligonucleotide primers are designed to be 100% complementary to a sequence on a starting template molecule, and all changes in the sequence of the copied molecule in the sequence homologous to the oligonucleotide primer are the result of errors in the amplification process.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette or a transformation-ready circular molecule.

Transformation-ready circular molecule: A non-replicating, circular DNA molecule that was generated in vitro, that is, by PCR or other synthetic means, which can be used to transform a host genome. Preferred constructs will comprise all of the genetic elements necessary to direct the expression of one or more exogenous, desired or selected genes or sequences, lack ancillary sequences, and contain lox sites.

Transformed cell: A cell, the DNA complement of which has been altered by the introduction of an exogenous DNA molecule into that cell.

Transgene: A segment of DNA which has been incorporated into a host genome or is capable of autonomous replication in a host cell and is capable of causing the expression of one or more cellular products. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not originally present in a non-transgenic plant of the same strain. The transgenic plant may additionally contain sequences which are native to the plant being transformed, but wherein the "exogenous" gene has been altered in order to alter the level or pattern of expression of the gene.

Transit peptide: A polypeptide sequence which is capable of directing a polypeptide to a particular organelle or other location within a cell.

Vector: A DNA molecule capable of replication in a host cell and/or to which another DNA segment can be operatively linked so as to bring about replication of the attached segment. A plasmid is an exemplary vector.

XII. EXAMPLES

The following examples are included to illustrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The current inventors have demonstrated the utility of non-replicating, transformation-ready circular molecules containing selected DNA sequences and single lox sites for site-directed integration into the genome of a plant. Expression and phenotypic effectiveness of transgenic material inserted into a host genome can be influenced by several different factors, including but not limited to, location within the genome, activity of adjacent host sequences, intactness of inserted DNA, ancillary sequences introduced with the transgenic DNA, and number of copies of the exogenous DNA. Additional molecular manipulations are often necessary to remove ancillary sequences, such as bacterial origins of replication, from transformation vectors or cassettes prior to the transformation of the host. It would be advantageous to be able to generate in vitro, an adequate number of transformation-ready circular molecules lacking ancillary sequences that can be inserted into the genome at specific sites, such as lox sites, which are previously known to allow expression of exogenous DNA. Such site-directed insertion would also allow for easier generation of event-specific assays.

EXAMPLE 1

Preparation of Starting Circular Template Molecules

One of skill in the art will recognize from the descriptions herein that a wide variety of transformation-ready circular molecules can be prepared and used for transformation in accordance with the instant invention. For illustrative purposes, examples of particular starting materials are described herein including three particular transformation-ready circular molecules that were prepared therefrom for use in transformation in accordance to the methods of this invention: MON55215; MON55229; MON68602.

For the purposes of this discussion the following nomenclature will be used. Starting nucleic acid molecules, which may be single- or double-stranded, linear or circular DNA and which may contain ancillary sequences in addition to the sequences of interest, will be referred to as smMON### or smDPG###. Circular template molecules, preferably lacking ancillary sequences and containing only the sequences of interest, and that are useful for amplification in a PCR reaction, will be referred to as ctMON###. Products of the PCR reaction, or transformation-ready circular molecules of the invention, will be referred to as trMON###. Other plasmid molecules not utilized for the preparation of the transformation-ready circular molecules of the invention will be referred to as pMON###.

Figure 2A:
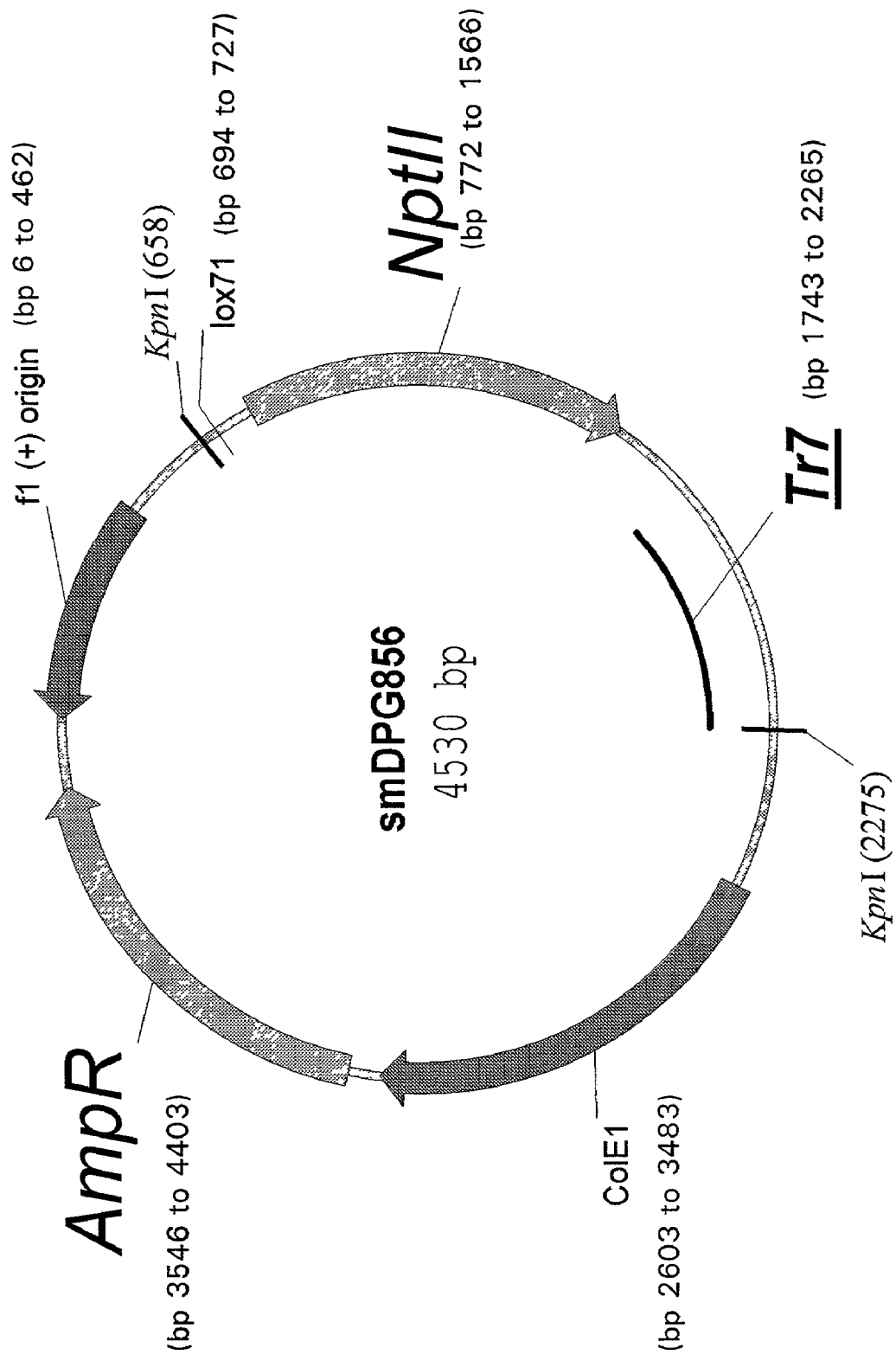
FIGS. 2A–B. (2A) Map of smDPG856. (2B) Map of circular template ctMON52215 and location of non-mutagenizing primers. A map of trMON52215 would appear identical to that of ctMON52215. Sequences are labeled and pertinent restriction sites identified (bp=base pair).
Figure 2B:
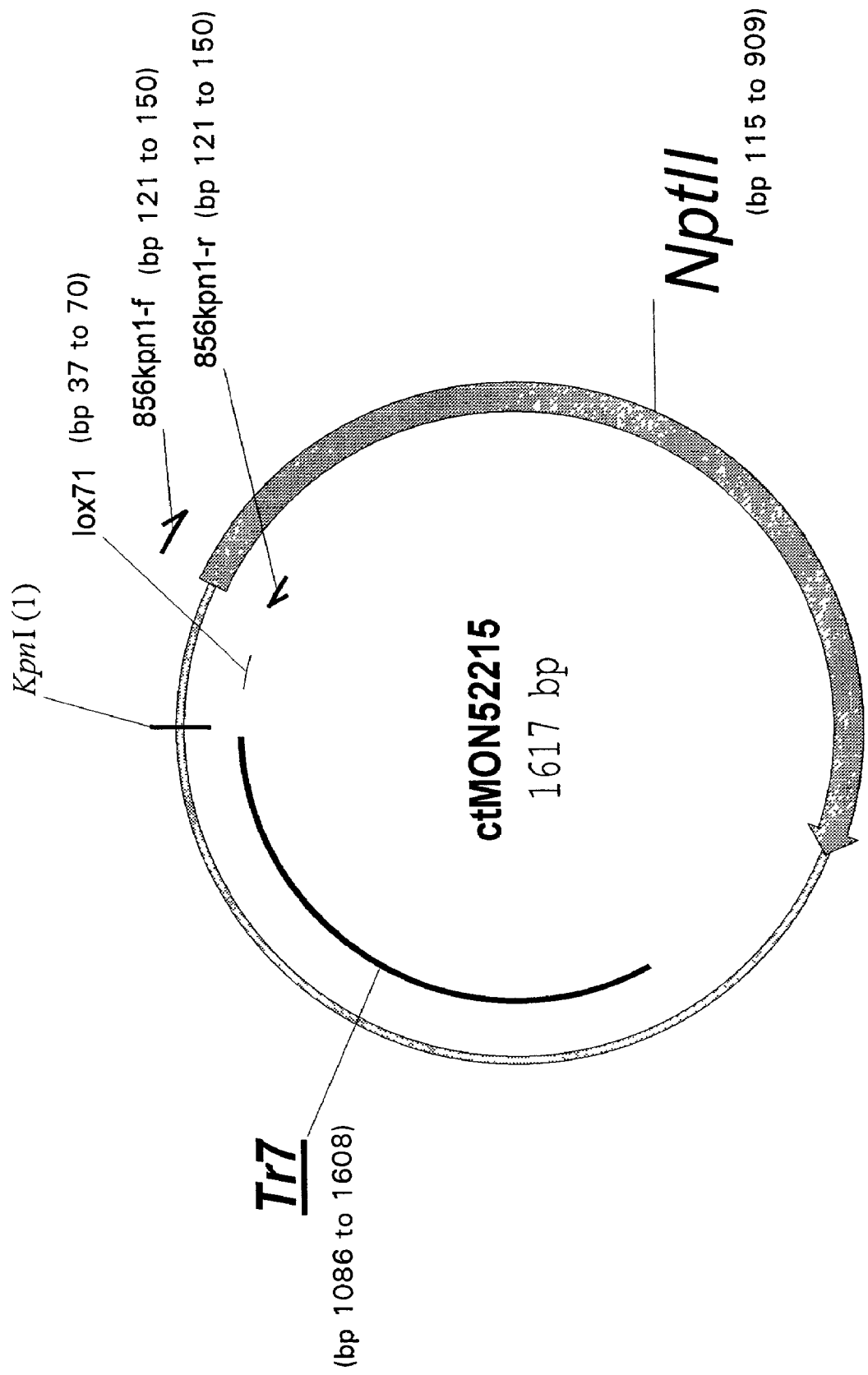

MON55215: The starting nucleic acid molecule for use in preparing ctMON55215 molecules was smDPG856 (about 4.3 kilobases (Kb); FIG. 2A). This starting material was a plasmid capable of replication in a bacterial host and it was necessary to remove ancillary sequences comprising the bacterial origin of replication and providing ampicillin resistance. SmDPG856 comprised sequences for: a replication origin f1(+), ampicillin resistance and an *E. coli* origin of replication isolated as an approximately 1.6 Kb sequence from pBLUESCRIPT (STRATAGENE, La Jolla, Calif.); a single lox71 site (SEQ ID NO:3; 34 basepairs (bp)), a promoterless neomycin phosphotransferase II selectable marker gene (NPT II; Potrykus et al., 1985; 795 bp) and a T7 3'UTR (Dhaese et al., 1983; 554 bp). The selected sequences of interest in ctMON55215 (~1.6 Kb; FIG. 2B) isolated from smDPG856 comprised: the single lox71 site (SEQ ID NO:3; 34 bp), the promoterless neomycin phosphotransferase II selectable marker gene (795 bp) and the T7 3'UTR (554 bp). One of skill in the art could use molecular biology techniques to isolate these or comparable sequences and generate these or other suitable starting material and circular template molecules.

Figure 4A:
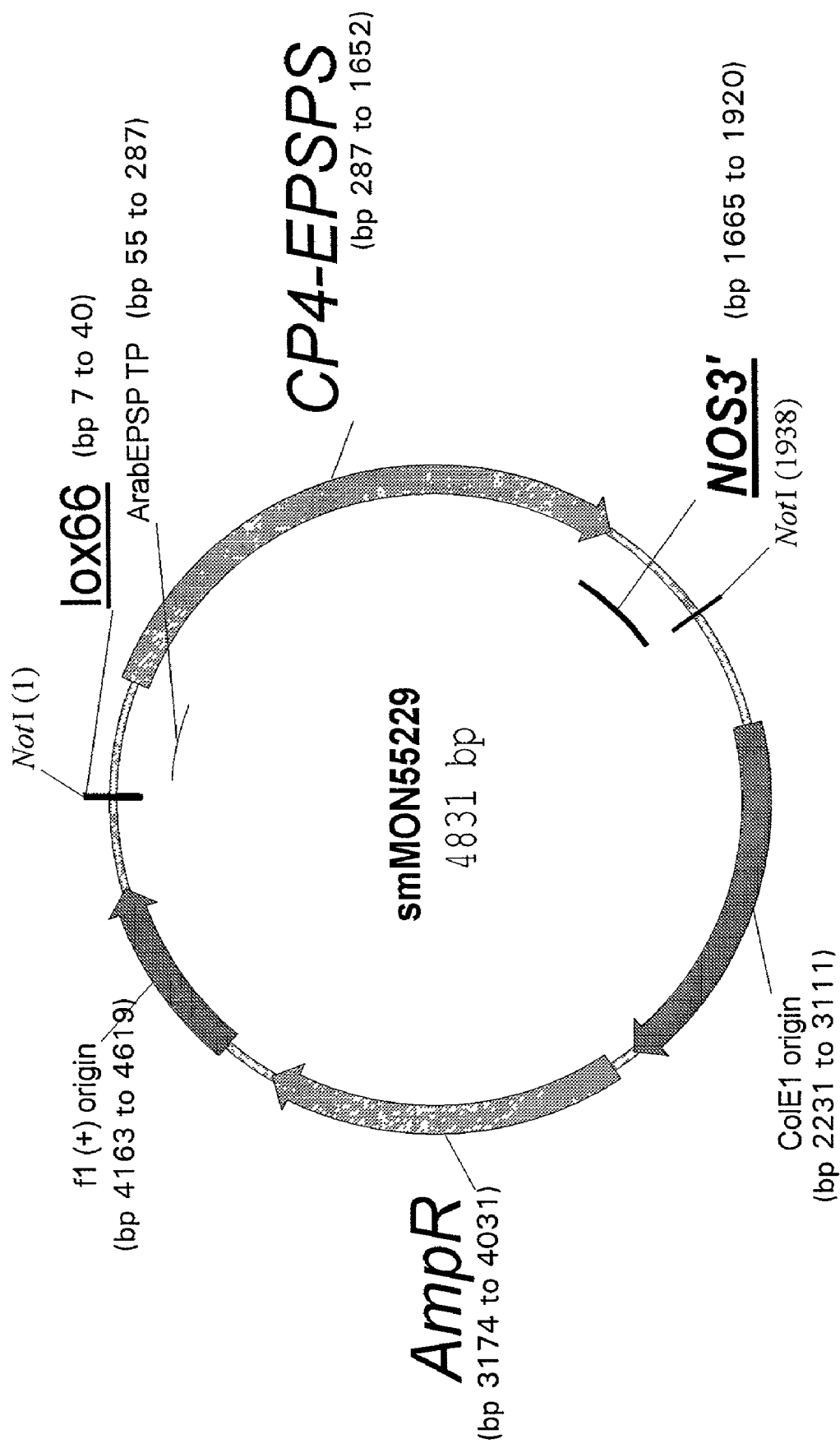
FIGS. 4A–B. (4A) Map of smMON55229. (4B) Map of circular template ctMON55229 and location of non-mutagenizing primers. A map of trMON55229 would appear identical to that of ctMON55229. Sequences are labeled and pertinent restriction sites identified (bp=base pair).
Figure 4B:
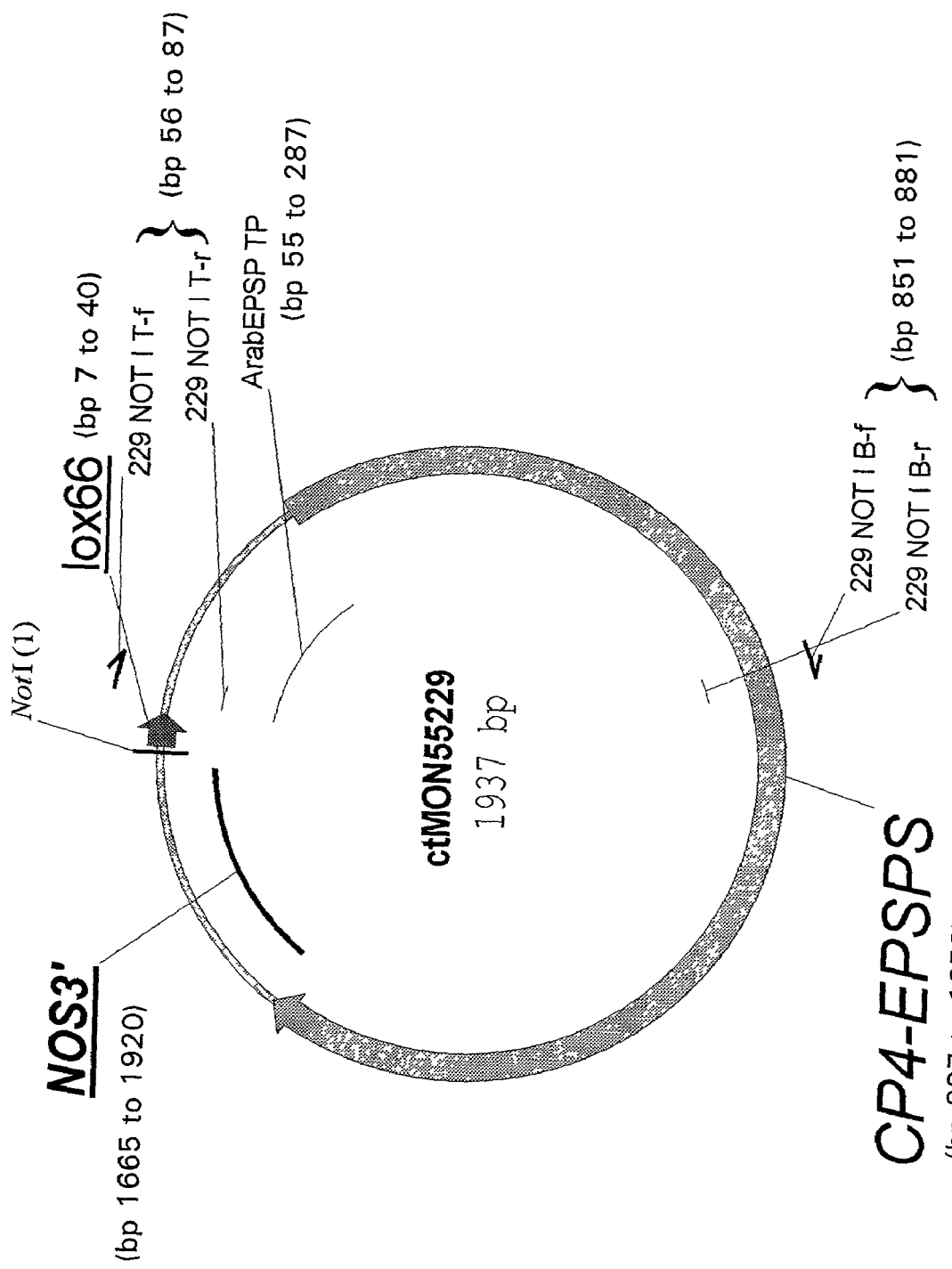

MON55229: The starting nucleic acid molecule for use in preparing ctMON55229 molecules was smMON55229 (about 4.8 Kb; FIG. 4A). The starting material was a plasmid capable of replication in a bacterial host and it was necessary to remove ancillary sequences comprising the bacterial origin of replication and providing ampicillin resistance. SmMON55229 comprised sequences for: a replication origin f1(+), ampicillin resistance and an *E. coli* origin of replication isolated as an approximately 1.6 Kb sequence from pBLUESCRIPT (STRATAGENE, La Jolla, Calif.); a single lox66 site (SEQ ID NO:2; 34 bp), an *Arabidopsis* EPSPS transit peptide (Klee et al., 1987; 233 bp), a promoterless glyphosate resistant EPSPS gene (CP4; U.S. Pat. No. 5,627,061; 1366 bp) and a nos 3'UTR (Bevan et al., 1983; 256 bp). The selected sequences of interest in ctMON55229 (~1.9 Kb; FIG. 4B) isolated from smMON55229 comprised: the single lox66 site (SEQ ID NO:2; 34 bp), the *Arabidopsis* EPSPS transit peptide (233 bp), the promoterless glyphosate resistant EPSPS gene (1366 bp) and the nos 3'UTR (256 bp). One of skill in the art could use molecular biology techniques to isolate these or comparable sequences and generate these or other suitable starting material and circular template molecules.

Figure 6A:
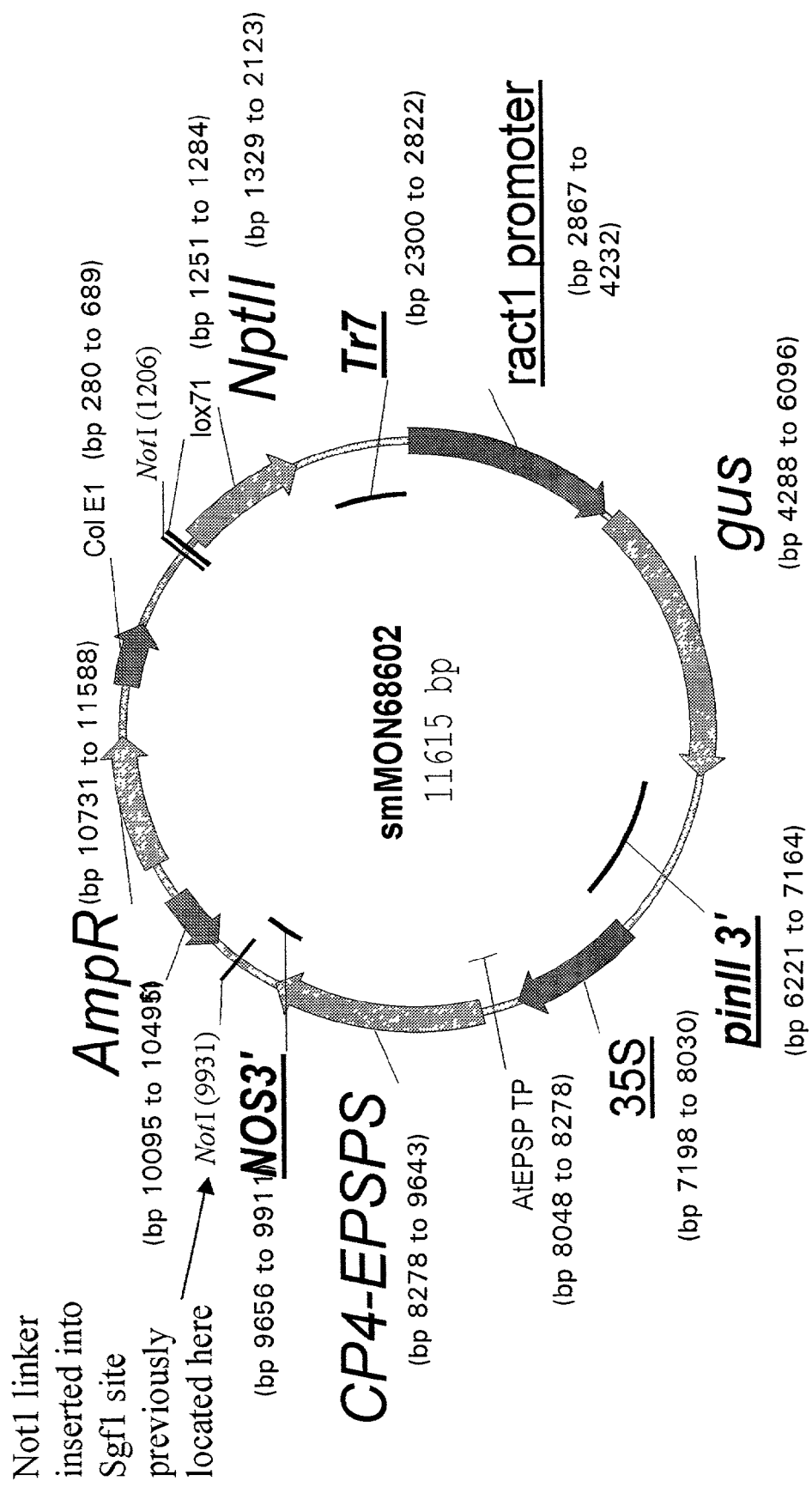
FIGS. 6A–B. (6A) Map of smMON68602. (6B) Map of circular template ctMON68602 and location of non-mutagenizing primers. A map of trMON68602 would appear identical to that of ctMON68602. Sequences are labeled and pertinent restriction sites identified (bp=base pair).
Figure 6B:
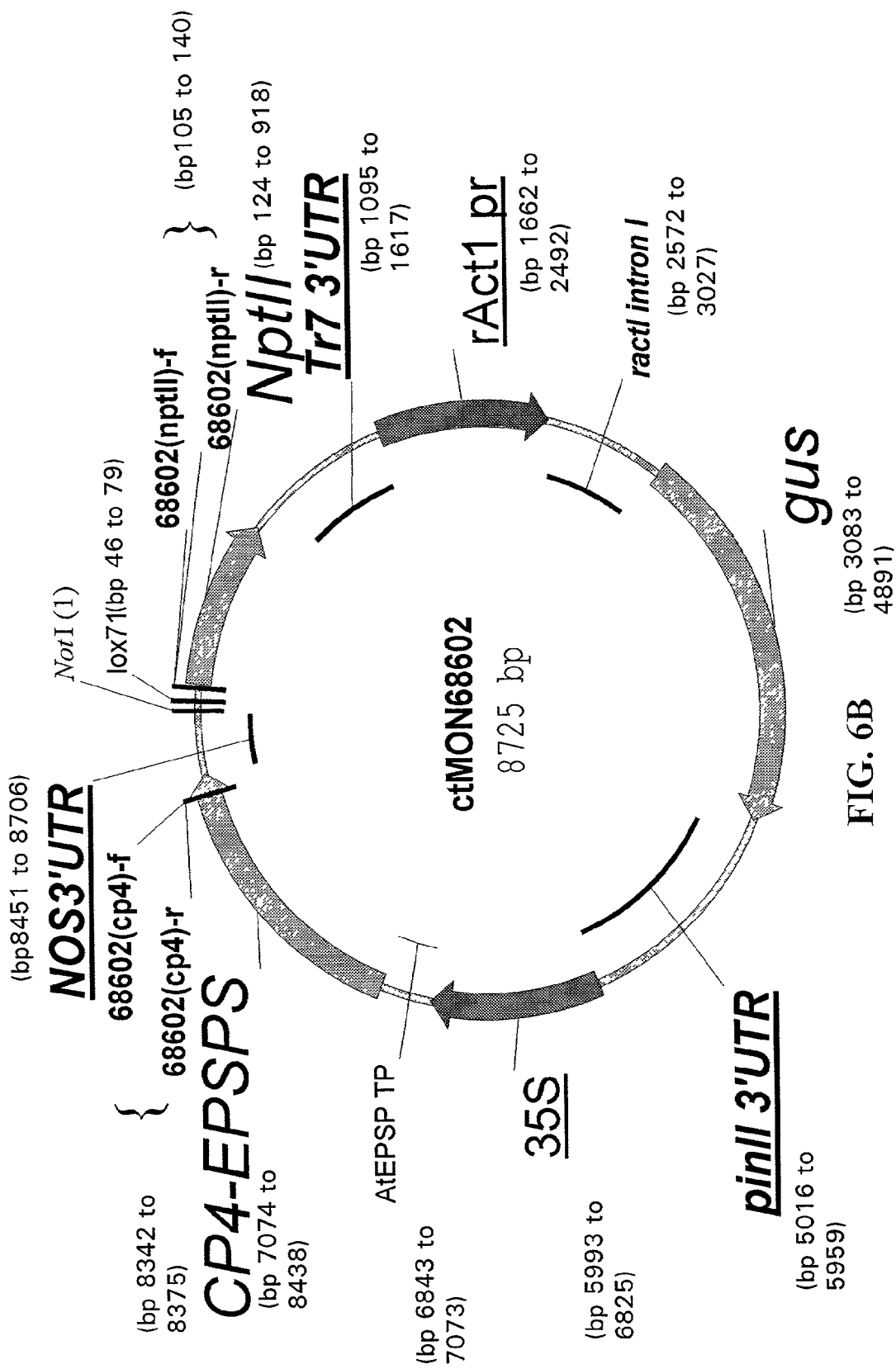

MON68602: The starting nucleic acid molecule for use in preparing ctMON68602 molecules was smMON68602 (about 11.6 Kb; FIG. 6A). The starting material was a plasmid capable of replication in a bacterial host and it was necessary to remove ancillary sequences comprising the bacterial origin of replication and providing ampicillin resistance. SmMON68602 comprised sequences for: replication origin f1(+), ampicillin resistance and *E. coli* origin of replication isolated as an approximately 1.6 Kb sequence from pBLUESCRIPT (STRATAGENE, La Jolla, Calif.); a single lox71 site (SEQ ID NO:3; 34 bp), a promoterless neomycin phosphotransferase II selectable marker gene (NPT II; Potrykus et al., 1985; 795 bp), a T7 3'UTR (Dhaese et al., 1983; 523); a rice actin 1 intron 1 promoter (McElroy et al., 1990; Zhang et al., 1991; Wang et al., 1992; U.S. Pat. No. 5,641,876; 1366 bp) operably linked to a β-glucuronidase screenable marker gene (uidA gene; Jefferson et al., 1986; the protein product is commonly referred to as GUS; 1809 bp), a pinII 3'UTR (Graham et al., 1986; 944 bp), and a glyphosate resistant EPSPS gene (CP4; U.S. Pat. No. 5,627,061; 1366 bp) operably linked to a 35S promoter (Odell et al., 1985; 833 bp), an *Arabidopsis* EPSPS transit peptide (Klee et al., 1987; 231 bp), and a nos 3'UTR (Bevan et al., 1983; 256 bp). The selected sequences of interest in ctMON68602 (~8.7 Kb; FIG. 6B) isolated from smMON68602 comprised: the single lox71 site (SEQ ID NO:3; 34 bp), the promoterless neomycin phosphotransferase II selectable marker gene (795 bp), the T7 3'UTR (523 bp); the rice actin 1 intron 1 promoter (1366 bp) operably linked to the β-glucuronidase screenable marker gene (1809 bp), the pinII 3'UTR (944 bp), and the glyphosate resistant EPSPS gene (1366 bp) operably linked to the 35S promoter (833 bp), the *Arabidopsis* EPSPS transit peptide (231 bp), and the nos 3'UTR (256 bp). One of skill in the art could use molecular biology techniques to isolate these or comparable sequences and generate these or other suitable starting material and circular template molecules.

Plasmid pMON68601 was the precursor plasmid used to generate smMON68602. pMON68601 lacked convenient restriction enzyme sites which allowed for both 1) the isolation of selected sequences of interest away from ancillary sequences and 2) provided compatible ends for subsequent self-ligation of the selected sequences to form a circular template. pMON68601 comprised a single, unique Not I site and was modified to comprise a second NotI site. A linker containing the sequence for NotI having Sgf I compatible ends with the following sequence

```
5'   CGC GCG GCC GCC TCG AGA T 3'
3' TA GCG CGC CGG CGG AGC TC    5'
``` was generated by hybridizing two oligonucleotides together (SEQ ID NO:10 and SEQ ID NO:11) and ligating the double-stranded product into the unique SgfI site of pMON68601 to generate smMON68602. As a result of the addition of the linker, NotI sites were located on either side of the desired sequences in smMON68602 such that digestion with NotI released the selected sequences on a single fragment with compatible ends for self-ligation and subsequent formation of circular templates.

Approximately 10 μg of starting nucleic acid molecules was digested with the appropriate restriction enzyme to liberate a fragment containing only the selected DNA sequences. SmDPG856 was digested with KpnI, and sm55229 and sm68602 were digested with NotI restriction enzymes, each according to manufacturer's directions (Roche Molecular Biochemicals, Indianapolis, Ind.). Products of the digestion were separated on a 0.8% agarose gel, the desired band sliced out of the gel, and the selected DNA purified from the gel slice using a QIAquick Gel Extraction kit according to the manufacturer's recommendations, using approximately 30–100 μl water for the final elution, preferably 30 to 80 μl and most preferably 50 μl (QIAGEN Inc., Valencia, Calif.). Ten to forty μl of the isolated fragment was then subjected to a standard ligation reaction using $T_4$ DNA ligase (New England BioLabs, Inc., Beverly, Mass.), by which circular template molecules containing only the sequences of interest could be generated. In one embodiment of the invention, linear fragments or concatamers of linear fragments may be removed from the reaction mixture by the addition of an exonuclease such as lambda exonuclease (New England BioLabs, Inc., Beverly, Mass.). QIAquick Nucleotide Purification kit (QIAGEN Inc., Valencia, Calif.) was utilized according to manufacturer's recommendations to purify the ligation or nuclease treated reaction containing the circular templates prior to utilization in a PCR reaction. The templates were suspended in 30–100 μl elution buffer, preferably 30 to 80 μl and most preferably 50 μl (10 mM Tris, pH 8.0 provided by the manufacturer) and quantitated. Typical concentrations of eluted product ranged from 5 to 70 ng/μl, most typically 15 to 30 ng/μl of eluted product. Alternatively, an aliquot of unpurified ligation reaction may be added directly to the PCR reaction.

EXAMPLE 2

Design of Oligonucleotides

It is known to those of ordinary skill in the art that a variety of oligonucleotide primers can be designed and used in PCR. Several parameters can influence the effectiveness of a primer such as, but not limited to, length, sequence, location on the template sequence, melting temperature ($T_m$) or G/C content. Of particular interest to the instant invention are the parameters of length, $T_m$ and placement of the non-mutagenizing oligonucleotides on the circular template molecule.

Non-mutagenizing oligonucleotides were designed such that the $T_m$ of the oligonucleotides was calculated to be at least 65° C. One of skill in the art will recognize that several different calculations exist for determining the $T_m$ of a particular oligonucleotide. A calculation based upon nearest neighbor analysis was utilized to calculate oligonucleotide $T_m$ (see, for example, Rychlik et al., 1990). The length of the non-mutagenizing oligonucleotides typically varied between 30 to 40 bases, although molecules could be shorter or longer as needed.

It is the belief of the current inventors that non-mutagenizing oligonucleotide pairs sharing 100% homology, i.e., are completely complementary, may be placed in various locations on the circular template for the generation of transformation-ready circular molecules. It is also the belief of the current inventors that non-mutagenizing oligonucleotides of 36 base pairs in length that shared 100% homology over 17 nucleotides at each 5' end generated what appeared to be a linear rather than circular PCR product. The primers may be placed 5' or 3' to the restriction and ligation site as well as opposite of the restriction and ligation site on the circular template. For example, non-mutagenizing oligonucleotides comprising sequences in SEQ ID NO:5 and SEQ ID NO:6 hybridized to a location approximately 120 base pairs 3' of the KpnI ligation site in ctMON52215 (see FIG. 2B). Alternatively, non-mutagenizing oligonucleotides comprising sequences in SEQ ID NO:9 and SEQ ID NO:10 hybridized to a location approximately 850 base pairs 3' of the NotI ligation site in ctMON55229 (see FIG. 4B). It is contemplated that non-mutagenizing oligonucleotides homologous to the restriction and ligation site may also be employed although one of skill in the art would commonly avoid palindromic sequences in oligonucleotides.

Exemplary non-mutagenizing oligonucleotides utilized in the practice of this invention can be found in SEQ ID NO:5, SEQ ID NO:6, SEQ ID NO:7, SEQ ID NO:8, SEQ ID NO:9, SEQ ID NO:10, SEQ ID NO:13, SEQ ID NO:14, SEQ ID NO:15 and SEQ ID NO:16.

EXAMPLE 3

PCR of Circular Template to Prepare Transformation-Ready Circular Molecules Generally, PCR cycling conditions comprise a denaturation step, an annealing step and an extension step in which the thermostable DNA polymerase, beginning at the double-stranded region of DNA resulting from the annealing of a primer, synthesizes a nascent strand of DNA complementary to the template strand. One of skill in the art would recognize that a number of parameters contribute to the generation of PCR product including but not limited to, temperature, incubation time at each step, numbers of steps, nucleotides, choice of thermostable DNA polymerase, primers and template molecules. One of ordinary skill in the art would also recognize that conditions may be optimized for individual template and primer combinations, or a plurality of templates and primer combinations.

Analysis and purification of the PCR reactions were carried out using methods familiar to one of skill in the art. Bacterial cells (*E. coli*) were transformed with an aliquot of the PCR reaction and no colonies were recovered. Aliquots of the PCR reaction were analyzed for product on agarose gels or by spectrophotometric measure. Products of the PCR reactions were purified directly using a High Pure PCR kit (Roche Molecular Biochemicals, Indianapolis, Ind.). Alternatively, PCR products are separated on agarose gels, and the transformation-ready circular molecules excised and purified using a QIAquick Gel Extraction kit (QIAGEN Inc., Valencia, Calif.) or using other purification methods known in the art. Concentrations of the purified transformation-ready circular molecules recovered ranged from approximately 5 to 200 ng/µl, more often approximately 5 to 100 ng/µl. One of skill in the art would realize that various standard methods could be used to concentrate or dilute the purified non-replicating, circular molecules to a desired concentration for use in transformation.

PCR Conditions for ctpMON52215 (~1.6 Kb) were as Follows:

The non-mutagenizing oligonucleotide primers (SEQ ID NO:5 and SEQ ID NO:6) that were used hybridize to a location approximately 120 bases 3', or downstream, to the KpnI ligation site (FIG. 2B).
1. 95° C. for 30 seconds
2. 59° C. for 30 seconds (alternatively, 1 minute)
3. 72° C. for 2 minutes and 24 seconds
Cycle from steps 1 to 3 for 25 times.

Taq polymerase (Roche Molecular Biochemicals, Indianapolis, Ind.) was used according to manufacturer's recommendations, in a 260 µl reaction volume with 7.8 µl of circular template; a range of approximately 4 to 105 ng of template was found to work under these PCR conditions. RedTaq DNA polymerase (SIGMA, St. Louis, Mo.) was also used to amplify transformation-ready circular molecules from ctpMON52215. From a PCR reaction initiated with approximately 4.2 ng of starting circular templates, approximately 1,625 ng of transformation-ready circular molecules were recovered. From a PCR reaction initiated with approximately 21 ng of starting circular templates, approximately 4,625 ng of transformation-ready circular molecules were recovered.

PCR Conditions for ctpMON55229 (~1.9 Kb) were as Follows:

The non-mutagenizing oligonucleotide primers (SEQ ID NO:7 and SEQ ID NO:8) that were used hybridize to a location approximately 50 bases 3', or downstream, to the NotI ligation site (FIG. 4B). Other non-mutagenizing oligonucleotide primers (SEQ ID NO:9 and SEQ ID NO:10) that were used hybridize to a location approximately 850 bases 3' to the NotI ligation site (FIG. 4B).
1. 95° C. for 30 seconds
2. 59° C. for 30 seconds
3. 72° C. for 3 minutes and 48 seconds
Cycle from steps 1 to 3 for 20 times.

KlenTaq polymerase (SIGMA, St. Loius, Mo.) was used according to manufacturer's recommendations in a 260 µl reaction volume with 10 µl of circular template.

Alternatively, transformation-ready circular molecules were prepared using the following PCR conditions:
1. 95° C. for 30 seconds
2. 59° C. for 1 minute
3. 72° C. for 3 minutes and 24 seconds
Cycle from steps 1 to 3 for 25 times.

REDAccu Taq La DNA polymerase or KlenTaq LA DNA polymerase mix (SIGMA, St. Loius, Mo.) were used according to manufacturer's recommendations in a 260 µl reaction volume with 5.0 µl of circular template.

Alternatively, transformation-ready circular molecules were prepared using a two-step PCR as follows:
1. 95° C. for 30 seconds
2. 68° C. for 3 minutes and 52 seconds
Cycle from steps 1 to 2 for 25 times.

REDAccu Taq La DNA polymerase or KlenTaq LA DNA polymerase mix (SIGMA, St. Louis, Mo.) were used according to manufacturer's recommendations in a 260 µl reaction volume with 5.0 µl of circular template.

PCR Conditions for ctpMON68602 (~8.7 Kb) are as Follows:

The non-mutagenizing oligonucleotide primers (SEQ ID NO:13 and SEQ ID NO:14) hybridize to a location approximately 100 bases 3', or downstream, to the NotI ligation site (FIG. 6B). Other non-mutagenizing oligonucleotide primers (SEQ ID NO:15 and SEQ ID NO:16) that may be useful hybridize to a location approximately 380 bases 3' to the NotI ligation site (FIG. 6B).
1. 95° C. for 1 minute
2. 95° C. for 30 seconds
3. 68° C. for 10 minutes
Cycle from steps 2 to 3 for 19 times.
4. 68° C. for 10 minutes
Expand Taq Polymerase (Roche Molecular Biochemicals, Indianapolis, Ind.), REDAccuTaq La DNA polymerase or KlenTaq LA DNA polymerase mix (SIGMA, St. Louis, Mo.) is used according to manufacturer's recommendations in a 50 µl reaction volume with 6.0 µl of circular template.

EXAMPLE 4

Stable Transformation of Maize with Transformation-Ready Circular Molecules

The transformation-ready circular molecules of the invention were transformed into two different maize lines, H99 and Hi-II. The site-specific target site in the two maize backgrounds comprised, from 5' to 3', a 35S promoter (Odell et al., 1985), a lox66 site (SEQ ID NO:2), a bar selectable marker gene (U.S. Pat. No. 5,550,318) and a T7 3'UTR sequence (Dhaese et al., 1983). This target site is referred to as NN03 (see FIG. 1). In this case, insertion of the transformation-ready circular molecules into the lox66 site operably linked the selected DNA to the 35S promoter.

Linear cassette control DNA was prepared for transformation as follows. SmDPG856 was digested with Kpn1, and smMON55229 or smMON68602 were digested with NotI according to manufacturer's recommendations (Roche Molecular Biochemicals, Indianapolis, Ind.). The digestion products were dephosphorylated, preferably using calf alkaline intestinal phosphatase (Roche Molecular Biochemicals, Indianapolis, Ind.), and purified using QIAQuick Nucleotide cleanup kit according to manufacturer's instructions (QIAGEN Inc., Valencia, Calif.). The ends of the molecule were then made blunt by using Klenow enzyme in the presence of all four nucleotides and conditions as recommended by the manufacturer (Roche Molecular Biochemicals, Indianapolis, Ind.). The products were separated on a 0.8% agarose gel and the fragment containing the selected sequences was isolated. The DNA was purified away from the agarose support using QIAquick Gel Elution kit (QIAGEN Inc., Valencia, Calif.). The eluted DNA was quantitated and subsequently used for transformation.

Plasmid control DNA comprised smDPG856, smMON55229 and smMON68601, each of which contained ancillary sequences in addition to the selected sequences of interest. These molecules were capable of replication in a bacterial host and were grown, isolated, purified and quantitated using standard molecular biology techniques familiar to one of skill in the art.

Figure 8:
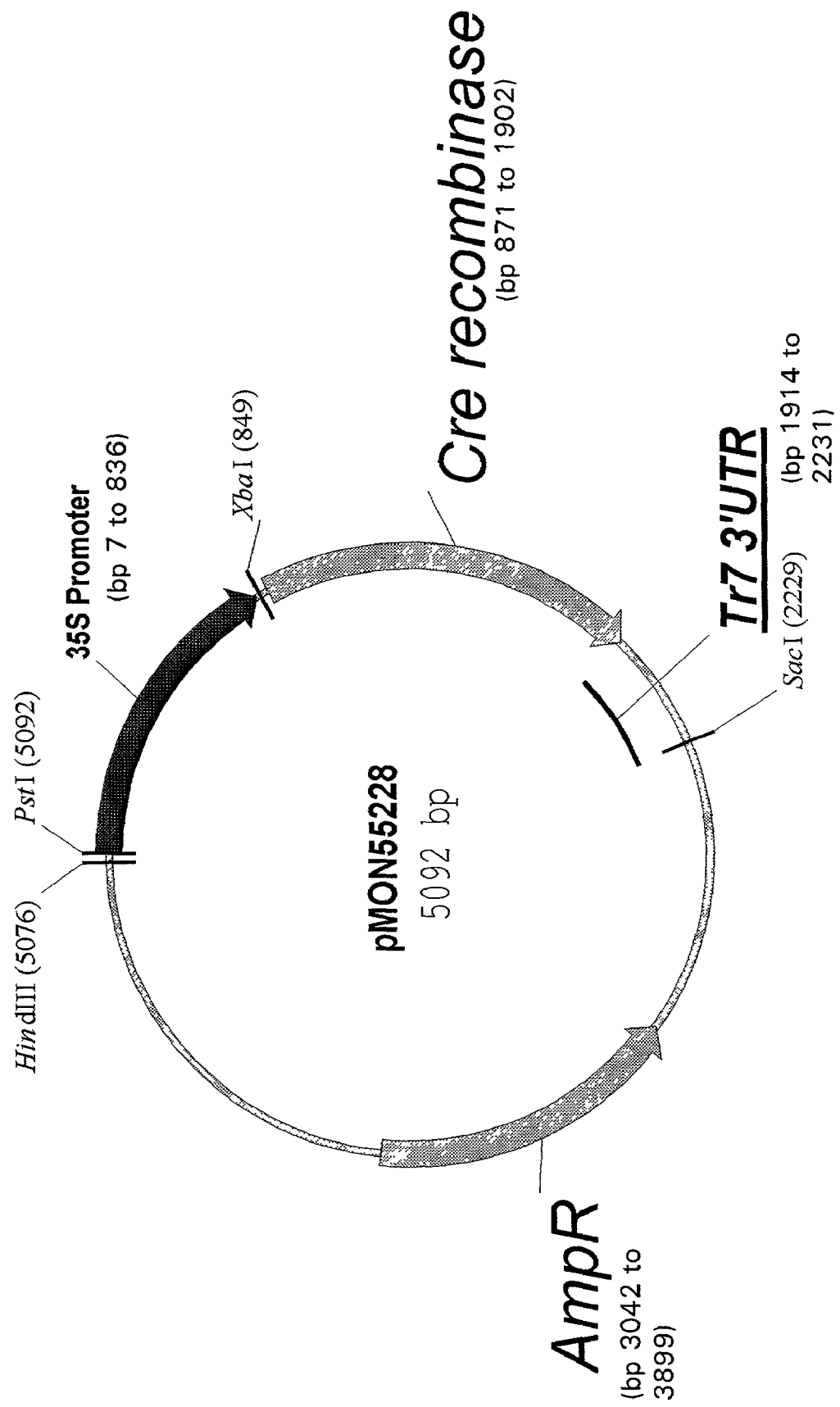
FIG. 8. Map of CRE-recombinase providing vector pMON55228.

All starting nucleic acid molecules and transformation-ready circular molecules of the invention comprised first single lox sites. To effect site-directed integration into second single target lox sites already residing in the host genome, it was necessary to provide CRE-recombinase. CRE-recombinase was provided from a plasmid vector which comprised a CRE coding sequence (Sternberg et al., 1986) operably linked to a 35S promoter (Odell et al., 1985) and a Tr7 3'UTR (Dhaese et al., 1983; pMON55228; FIG. 8). For co-bombardment transformation, approximately 5000 to 1000 ng, preferably 3000 to 1000 ng, or more preferably 1500 to 1000 ng, or most preferably 1000 ng of transformation-ready circular molecules, starting material controls or linear cassette controls were mixed with approximately 200 ng of pMON55228. The concentration of pMON55228 was approximately 5-fold less than that of the other molecules and it is contemplated that pMON55228 molecules provided CRE-recombinase by transient expression from the plasmid molecules.

After transformation with trMON52215/pMON55228, paromomycin resistant calli representing up to seven different transformation events were isolated. As the antibiotic paromomycin is toxic to plant cells, only cells containing an NPTII sequence, or other appropriate antibiotic resistance sequence, would be resistant and able to survive in the presence of the antibiotic; thus, one would expect to obtain resistant callus only if the cells contained the appropriate transgene. The circular molecule used for transformation comprised a lox site, NPTII sequence and 3'UTR; the molecule lacked a promoter sequence. The NN03 target site in the recipient genome contained a 35S promoter designed such that integration into the NN03 lox site would operably link a selected sequence to the promoter sequence. The recovery of paromomycin resistant calli indicates that site directed integration occurred, operably linking the promoterless NPTII gene of the transformation-ready circular molecule with the 35S promoter of the NN03 target site. Three plantlets from one event matured and were crossed to a non-transformed maize line for seed production. All three plants produced $R_1$ seed. Seed were collected.

$R_1$ seed were planted and seedlings assayed for NPT II susceptibility using a leaf whorl assay. The leaf whorl assay is carried out by the surface application of paromomycin to the leaf and visual inspection for bleaching of the tissue; tissue expressing the NPT II gene will remain green while tissue lacking NPT II gene expression will bleach or turn yellow/white in color. One liter of NPT II whorl assay buffer (NWB) was prepared using 1 g kanamycin, 1 g paromomycin (both from SIGMA Chemicals, St. Louis, Mo.) and 0.06% Silwet L-77 (polyalkyleneoxide modified heptamethyl-trisilane; OSi Specialties, Norwalk, CT) in distilled water. One liter of control whorl assay buffer was prepared using 0.06% Silwet L-77 in distilled water (CWB). Depending upon the age of the plant, 10–100 µl of NWB or CWB is applied to the whorl of the plant with younger plants receiving a smaller dose than larger plants. Plants were treated with 60 µl of NWB at approximately V5 stage and scored for bleaching. All of the tested plants showed antibiotic induced bleaching. However, the bleached plants were regenerated from paromomycin resistant calli and Southern blot analysis demonstrated the presence of the NPTII gene in $R_0$ plants. Therefore, the plants assayed for antibiotic resistance are believed to contain the NPT II gene. Standard molecular biology techniques, including but not limited to, Southern analysis, PCR, or RT-PCR are utilized to characterize the insertion of the NPTII sequences into the target site of the plant genome.

Figure 3:
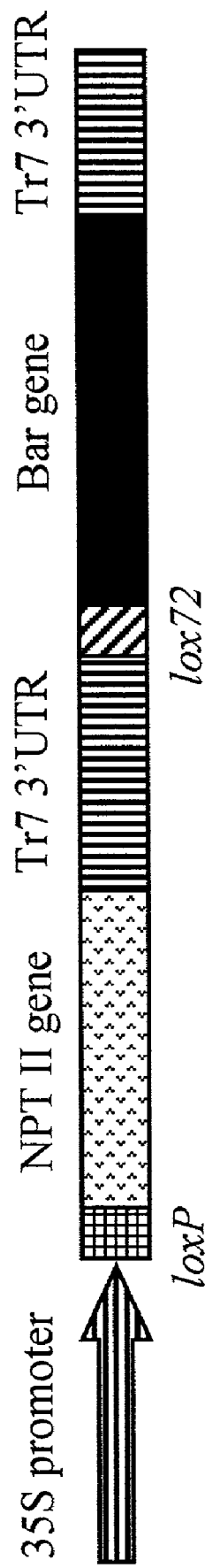
FIG. 3. Schematic of trMON52215 circular molecule inserted into the lox66 site (SEQ ID NO:2) of NN03.
Figure 5:
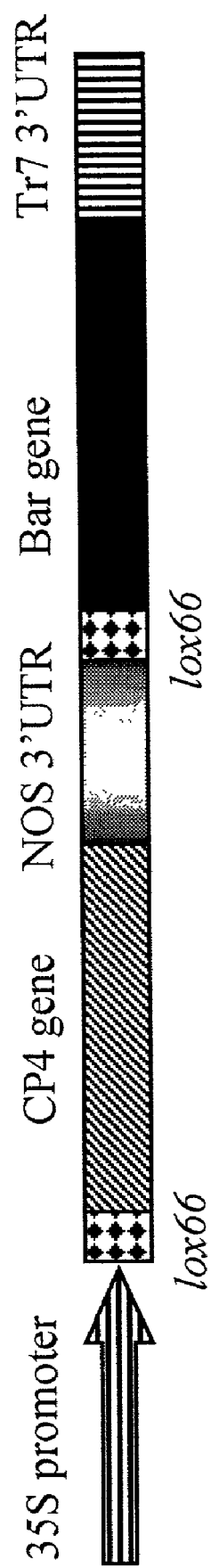
FIG. 5. Schematic of trMON55229 circular molecule inserted into the lox66 site (SEQ ID NO:2) of NN03.
Figure 7:
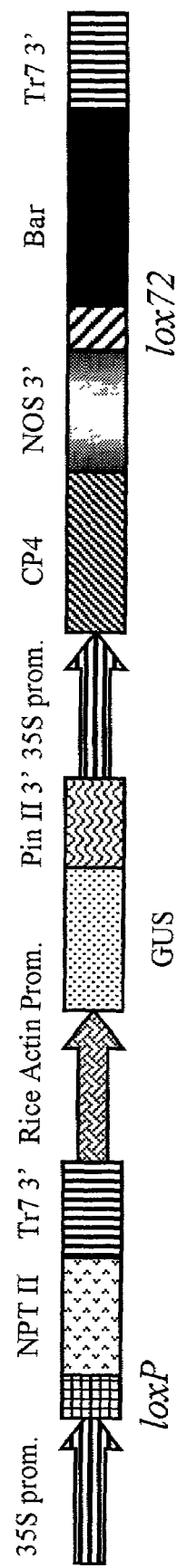
FIG. 7. Schematic of trMON68602 circular molecule inserted into the lox66 site (SEQ ID NO:2) of NN03.

FIGS. 3, 5 and 7 provide illustrations of the insertion products of a single transformation-ready circular molecule of trMON52215, trMON55229 or trMON68602 into the NN03 lox66 target site.

EXAMPLE 5

Preparation of Microprojectiles

Microprojectiles were prepared for use with the helium gun by adding 60 mg of 0.6 µm gold particles (BioRad, cat. no. 165-2262) to 1000 µl absolute ethanol and incubating for at least 3 hours at room temperature followed by storage at −20° C. Twenty to thirty five µl of the sterile gold particles or more preferably 30 to 35 μl of gold particles (30 μl contains 1.8 mg of particles) were centrifuged in a microcentrifuge for up to 1 to 5 min. The supernatant was removed and the particles carefully washed in one ml sterile water. Microprojectile particles were resuspended in 30 μl of DNA solution containing about 1000 ng of transformation-ready circular molecules, starting material control molecules or linear cassette, and about 200 ng of plasmid pMON55228.

Two hundred twenty microliters sterile water, 250 μl 2.5 M $CaCl_2$ and 50 μl stock spermidine (14 μl spermidine in 986 μl water; 0.1M) were then added to the particle containing solution. The solution was then thoroughly mixed and placed on ice, followed by vortexing at 4° C. for 10 minutes and centrifugation at 500 to 700 rpm for 5 to 7 minutes. The supernatant was removed and the pellet resuspended in 600 μl absolute ethanol. Following centrifugation at 500 to 700 rpm for 5 to 7 minutes, the pellet was resuspended in 36–38 μl of absolute ethanol, vortexed for approximately 20 seconds, and sonicated for 10–30 seconds. At this stage the particles were typically allowed to sit for 0–5 minutes, after which 5–10 μl of the supernatant was removed and dispensed on the surface of a flyer disk and the ethanol was allowed to dry completely. Alternatively, particles may be removed directly after resuspension and vortexing 20 to 30 seconds in 36 μl–38 μl of ethanol, placed on the flyer disk and allowed to dry as done for the settled treatment. The bombardment chamber was then evacuated to approximately 28 in. Hg prior to bombardment. The particles were then used for bombardment by a helium blast of approximately 1100 psi using the DuPont Biolistics PDS1000He particle bombardment device.

Microprojectiles were prepared for use with the electric gun by suspending 10 mg of 0.6 μm gold particles (BioRad) in 50 μL buffer (150 mM NaCl, 10 mM Tris-HCl, pH 8.0). About 1500 ng of transformation-ready circular molecules, starting material control molecules or linear cassette, and about 600 ng of plasmid pMON55228 were added to the suspension of gold particles and gently vortexed for about five seconds.

Seventy five μL of 0.1 M spermidine was added and the solution vortexed gently for about 5 seconds. Seventy five μL of a 25% solution of polyethylene glycol (3000–4000 molecular weight, American Type Culture Collection) was added and the solution was gently vortexed for five seconds. Seventy five μL of 2.5 M $CaCl_2$ was added and the solution vortexed for five seconds. Following the addition of $CaCl_2$, the solution was incubated at room temperature for 10 to 15 minutes. The suspension was subsequently centrifuged for 20 seconds at 12,000 rpm (Sorval MC-12V centrifuge) and the supernatant discarded. The gold particle/DNA pellet was washed twice with one ml 100% ethanol and resuspended to a total volume of 10 ml in 100% ethanol. The gold particle/DNA preparation was stored at −20° C. for up to two weeks.

DNA was introduced into maize cells using the electric discharge particle acceleration gene delivery device (U.S. Pat. No. 5,015,580). The gold particle/DNA suspension was coated on Mylar sheets (Du Pont Mylar polyester film type SMMC2, aluminum coated on one side, over coated with PVDC co-polymer on both sides, cut to 18 mm square) by dispersion of 310 to 320 μl of the gold particle/DNA suspension on a sheet. After the gold particle suspension settled for one to three minutes, excess ethanol was removed and the sheets were air dried. Microprojectile bombardment of maize tissue was conducted as described in U.S. Pat. No. 5,015,580. AC voltage may be varied in the electric discharge particle delivery device. For microprojectile bombardment of Hi-II or H99 pre-cultured immature embryos, 30% to 40% of maximum voltage was preferably used. Following microprojectile bombardment, tissue was cultured in the dark at 27° C.

EXAMPLE 6

Bombardment of Hi-II Immature Embryos

Immature embryos (1.2–3.0 mm in length) of the corn genotype Hi-II are excised from surface-sterilized, greenhouse-grown ears of Hi-II 9 to 16 days post-pollination, preferably 10–12 days post-pollination. The Hi-II genotype was developed from an A188×B73 cross (Armstrong et al., 1991). Approximately 30 embryos per petri dish are plated axis side down (that is, scutellar side up) on a modified N6 medium containing 1 mg/L 2,4-D, 100 mg/L casein hydrolysate, 2.9 g/L L-proline, 16.9 mg/L silver nitrate, 2 mg/L L-glycine, and 2% sucrose solidified with 2 g/L Gelgro, pH 5.8 (#201V medium). An alternative modified N6 medium that may be used is #211 with appropriate supplements (see Table 7). Embryos are cultured in the dark for 2 to 6 days at 26–28° C.

Approximately 3–4 hours prior to bombardment, embryos are transferred to the above culture media with the sucrose concentration increased from 2% up to 12% (media #201SV). When embryos are transferred to the high osmoticum medium they are arranged in nickel-sized, concentric circles on the plate, starting 1 cm from the center of the dish, positioned such that they are scutellar side up and their coleorhizal end is orientated toward the center of the dish. Usually one concentric circle is formed with 25–35 embryos per plate, although it is also possible to prepare a plate with two circles of embryos.

The plates containing embryos are placed on the third shelf from the bottom, 5 cm below the stopping screen. The 1100 psi rupture discs are used for bombardment. Each plate of embryos is bombarded once with the DuPont Biolistics PDS1000He particle gun. Following bombardment, embryos are allowed to recover on high osmoticum medium (#201SV, 12% sucrose) overnight (16–24 hours) and are then transferred to the appropriate selection medium For glyphosate selection, embryos are maintained in the dark at 26° to 28° C. and typically form Type II callus during the selection process. After bombardment, embryos are allowed to incubate on media #201V for 1 to 7 days. Following this delay, the tissue is transferred to media #201JV, containing 1 mM glyphosate. After approximately 2 weeks, tissues are transferred to fresh #201K selection media (supplemented with 3 mM glyphosate). After approximately 2–6 more weeks, calli are transferred to fresh #201K media. Subsequent rounds of transfers are carried out approximately every 2 weeks onto media with 3mM glyphosate, for a total of 12–16 weeks of selection. Southern, Northern, TaqMAN™, PCR, RT-PCR, or other types of molecular techniques, can then be used for analysis of transformants and of gene expression.

For paromomycin selection, embryos are maintained in the dark at 26° to 28° C. and typically form Type II callus during the selection process. After bombardment, embryos are allowed to incubate on media #211V (or #201V) for 1 to 7 days. After this delay on the initial selection plate, tissue is transferred to #211HV media with 25 mg/L paromomycin. Approximately 2 weeks later, tissue is transferred to media #211G supplemented with 50 mg/L paromomycin. After approximately another 2 weeks, the tissue is transferred to media #211T containing 100 mg/L paromomycin. After approximately 2–4weeks, the tissue is transferred to fresh

211T media. A total of 7–15 weeks selection is typically sufficient, followed by regeneration of plants (see Example 8). Kanamycin selection may be performed in a similar manner. Following a delay period on media #211V (or #201V), tissue is transferred to media #211EE (100 mg/L kanamycin). After approximately 2 weeks, tissue is transferred to media #211F (200 mg/L kanamycin) for a period of 2–4 weeks. Tissue is then transferred to fresh #211F for an additional 2–4 weeks. A total of 7–15 weeks selection is typically sufficient, followed by regeneration of plants (see Example 8). One of skill in the art would also recognize that media supplemented with a mix of kanamycin and paromomycin may also be used for this selection scheme. Southern, Northern, TaqMan™, PCR, RT-PCR, or other types of molecular techniques, can then be used for analysis of transformants and of gene expression.

EXAMPLE 7

Transformation of H99 Immature Embryo or Callus and Selection with Paromomycin

Maize immature embryos (1.2–3.0 mm, 10–14 days post pollination) were isolated from greenhouse grown H99 plants that had been self or sib pollinated. Immature embryos were cultured on #211V medium in the dark at approximately 27° C. Immature embryos were bombarded 0–6 days after isolation. Prior to bombardment, the immature embryos were transferred to 211 medium containing 12% sucrose for 3–6 hours. Following bombardment, carried out as described in Example 6, tissue cultures were incubated overnight and transferred to #211 medium for approximately 1 week. Following this, tissues were transferred to #211T medium (100 mg/L paromomycin) for approximately 2–3 weeks. Tissues were then transferred to #211L medium (500 mg/L paromomycin). Every 2–3 weeks, callus was subdivided into small pieces (approximately 2–4 mm in diameter) and transferred to fresh selection medium (211L; 500 mg/L paromomycin). This subculture step was repeated at 2–3 week intervals for up to about 3–15 weeks post-bombardment, typically 6 to 9 weeks, with subdivision and visual selection for healthy, growing callus.

Alternatively, immature embryos could be cultured to produce embryogenic callus that can be used for bombardment. Embryogenic callus is expanded and maintained by subculturing at 2–3 week intervals to fresh #211 medium. Prior to bombardment, embryogenic callus (subdivided in approximately 2–4 mm clumps) or, preferably cultured embryos, are transferred to 211 medium containing 12% sucrose for 3–6 hours. As described above for immature embryos, the bombed callus is transferred to medium with increasing amounts of paromomycin to select for transformed tissue.

EXAMPLE 8

Regeneration of Fertile Transgenic Plants

Fertile transgenic plants were produced from transformed H99 maize cells. Transformed callus was transferred to maturation medium 217 (N6 salts, 1 mg/L thiamine-HCl, 0.5 mg/L niacin, 3.52 mg/L benzylaminopurine, 0.91 mg/L L-asparagine monohydrate, 100 mg/L myo-inositol, 0.5 g/L MES, 1.6 g/L $MgCl_2\cdot 6H_2O$, 100 mg/L casein hydrolysate, 0.69 g/L L-proline, 20 g/L sucrose, 2 g/L GELGRO™, pH 5.8) for five to nine days in the dark at 26°–28° C., whereupon somatic embryos mature and shoot regeneration begins. Tissue was transferred to medium 127T (MS salts, 0.65 mg/L niacin, 0.125 mg/L pyridoxine-HCl, 0.125 mg/L thiamine-HCl, 0.125 mg/L Ca pantothenate, 150 mg/L L-asparagine, 100 mg/L myo-inositol, 10 g/L glucose, 20 g/L L-maltose, 100 mg/L paromomycin, 5.5 g PHYTAGAR™, pH 5.8) for shoot development. Tissue on medium 127T was cultured in the light at 400–600 lux at 26° C. Plantlets were transferred to soil about 3 to 6 weeks after transfer to 127T medium when the plantlets were about 3 inches tall and had roots. Plantlets were grown further in a growth chamber and fully matured in a greenhouse.

Fertile transgenic plants are produced from transformed Hi-II maize cells. Regeneration of plants is initiated by transfer of callus from the final selection media to MS medium containing 0.04 mg/L NAA and 3 mg/L BAP (medium #105). Tissue is cultured in the dark for two weeks, followed by two weeks of culture on fresh medium #105 in low light. Tissue is subsequently transferred to MS medium with 6% sucrose without growth regulators (medium #110) and cultured in low light for approximately 2 weeks. Tissue is then subcultured to #110 medium in PHYTATRAYS™ or PLANTCONS®. Tissue in PHYTATRAYS™ or PLANT-CONS® is grown under high light in a growth chamber. Regenerated plants are transferred from PHYTATRAYS™ or PLANTCONS® to soil when the plantlets are about 3 inches tall and have roots. Plantlets are grown further in a growth chamber or greenhouse.

EXAMPLE 9

Methods for Microprojectile Bombardment

Many variations in techniques for microprojectile bombardment are well known in the art and therefore deemed useful with the current invention. Exemplary procedures for bombardment are discussed in, for example, PCT Publication No. WO 95/06128, the disclosure of which is specifically incorporated herein by reference in its entirety. Examples of target tissues which may be used with the current invention include immature embryos, Type I callus, Type II callus, Type III callus, suspension cultures and meristematic tissue (PCT Publication WO 96/04392). Some genotypes which are especially useful for maize transformation are specifically disclosed herein above, as well as in, for example, PCT Publication WO 95/06128. Preferred genotypes will be those which are readily transformable and which also may be regenerated to yield a fertile transgenic plant.

Any method for acceleration of microprojectiles may potentially be used to transform a plant cell with the current invention. A preferred method will be a gas-driven particle gun such as the DuPont Biolistics PDS1000He particle bombardment device. Exemplary particles for bombardment include those comprised of tungsten, gold, platinum, and the like. Gold particles are deemed particularly useful in the current invention, with 0.6 μm or 0.7 μm gold particles being preferred and 0.6 μm particles most preferred. The most preferred particles will be DNA coated and have a mean size between 0.6 μm and 1.0 μm. Alternatively, particles may be allowed to settle for 2–5 minutes following precipitation of DNA onto particles. Particles are then removed from the supernatant and used for microprojectile bombardment. It is believed that the settling step enriches for a population of particles coated with DNA in which fewer aggregates of particles are present.

As disclosed herein, any DNA sequence may potentially be used for transformation. The DNA segments or transformation-ready circular molecules used for transformation will preferably include one or more selectable, secretable or screenable markers. Many examples of such are well known in the art and are specifically disclosed herein. In the case of selectable markers, selection may be in solid or liquid media. The DNA segments or transformation-ready circular molecules used will preferably also include one or more genes which confer, either individually or in combination with other sequences, a desired phenotype on the transformed plant. Exemplary genes for transformation and the corresponding phenotypes these sequences may confer on the transformed plant are disclosed herein.

EXAMPLE 10

Introgression of Transgenes into Elite Varieties

Backcrossing can be used to improve a starting plant. Backcrossing transfers a specific desirable trait from one source to an inbred or other plant that lacks that trait. This can be accomplished, for example, by first crossing a superior inbred (A) (recurrent parent) to a donor inbred (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent, then the selected progeny are mated back to the superior recurrent parent (A). After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e. one or more transformation events.

Therefore, through a series a breeding manipulations, a selected transgene may be moved from one line into an entirely different line without the need for further recombinant manipulation. Transgenes are valuable in that they typically behave genetically as any other gene and can be manipulated by breeding techniques in a manner identical to any other corn gene. Therefore, one may produce inbred plants which are true breeding for one or more transgenes. By crossing different inbred plants, one may produce a large number of different hybrids with different combinations of transgenes. In this way, plants may be produced which have the desirable agronomic properties frequently associated with hybrids ("hybrid vigor"), as well as the desirable characteristics imparted by one or more transgene(s).

EXAMPLE 11

Marker Assisted Selection

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

In the process of marker assisted breeding, DNA sequences are used to follow desirable agronomic traits in the process of plant breeding (Tanksley et al., 1989). Marker assisted breeding may be undertaken as follows. Seed of plants with the desired trait are planted in soil in the greenhouse or in the field. Leaf tissue is harvested from the plant for preparation of DNA at any point in growth at which approximately one gram of leaf tissue can be removed from the plant without compromising the viability of the plant. Genomic DNA is isolated using a procedure modified from Shure et al. (1983). Approximately one gram of leaf tissue from a seedling is lyophilized (freeze-dried) overnight in 15 ml polypropylene tubes. Freeze-dried tissue is ground to a powder in the tube using a glass rod. Powdered tissue is mixed thoroughly with 3 ml extraction buffer (7.0 urea, 0.35 M NaCl, 0.05 M Tris-HCl pH 8.0, 0.01 M EDTA, 1% sarcosine). Tissue/buffer homogenate is extracted with 3 ml phenol/chloroform. The aqueous phase is separated by centrifugation, and precipitated twice using $\frac{1}{10}$ volume of 4.4 M ammonium acetate pH 5.2, and an equal volume of isopropanol. The precipitate is washed with 75% ethanol and resuspended in 100–500 µl TE (0.01 M Tris-HCl, 0.001 M EDTA, pH 8.0).

Genomic DNA is then digested with a 3-fold excess of restriction enzymes, electrophoresed through 0.8% agarose (FMC), and transferred (Southern, 1975) to Nytran using 10×SCP (20 SCP: 2M NaCl, 0.6 M disodium phosphate, 0.02 M disodium EDTA). The filters are prehybridized in 6×SCP, 10% dextran sulfate, 2% sarcosine, and 500 µg/ml denatured salmon sperm DNA and $^{32}$P-labeled probe generated by random priming (Feinberg & Vogelstein, 1983). Hybridized filters are washed in 2×SCP, 1% SDS at 65° C. for 30 minutes and visualized by autoradiography using Kodak XAR5 film. Genetic polymorphisms which are genetically linked to traits of interest are thereby used to predict the presence or absence of the traits of interest.

Those of skill in the art will recognize that there are many different ways to isolate DNA from plant tissues and that there are many different protocols for Southern hybridization that will produce identical results. Those of skill in the art will recognize that a Southern blot can be stripped of radioactive probe following autoradiography and re-probed with a different probe. In this manner one may identify each of the various transgenes that are present in the plant. One of skill in the art would also realize that non-radioactive detection technologies for Southerns are readily available for use. Further, one of skill in the art will recognize that any type of genetic marker which is polymorphic at the region(s) of interest may be used for the purpose of identifying the relative presence or absence of a trait, and that such information may be used for marker assisted breeding.

Each lane of a Southern blot represents DNA isolated from one plant. Through the use of multiplicity of gene integration events as probes on the same genomic DNA blot, the integration event composition of each plant may be determined. Correlations may be established between the contributions of particular integration events to the phenotype of the plant. Only those plants that contain a desired combination of integration events may be advanced to maturity and used for pollination. DNA probes corresponding to particular transgene integration events are useful markers during the course of plant breeding to identify and combine particular integration events without having to grow the plants and assay the plants for agronomic performance.

It is expected that one or more restriction enzymes will be used to digest genomic DNA, either singly or in combinations. One of skill in the art will recognize that many different restriction enzymes will be useful and the choice of restriction enzyme will depend on the DNA sequence of the transgene integration event that is used as a probe and the DNA sequences in the genome surrounding the transgene. For a probe, one will want to use DNA or RNA sequences which will hybridize to the DNA used for transformation. One will select a restriction enzyme that produces a DNA fragment following hybridization that is identifiable as the transgene integration event. Thus, particularly useful restriction enzymes will be those which reveal polymorphisms that are genetically linked to specific transgenes or traits of interest.

EXAMPLE 12

General Methods for Assays

DNA analysis of transformed plants is performed as follows. Genomic DNA is isolated using a procedure modified from Shure et al., 1983. Approximately 1 gm callus or leaf tissue is ground to a fine powder in liquid nitrogen using a mortar and pestle. Powdered tissue is mixed thoroughly with 4 ml extraction buffer (7.0 M urea, 0.35 M NaCl, 0.05 M Tris-HCl pH 8.0, 0.01 M EDTA, 1% sarcosine). Tissue/buffer homogenate is extracted with 4 ml phenol/chloroform. The aqueous phase is separated by centrifugation, passed through Miracloth, and precipitated twice using $\frac{1}{10}$ volume of 4.4 M ammonium acetate, pH 5.2 and an equal volume of isopropanol. The precipitate is washed with 70% ethanol and resuspended in 200–500 µl TE (0.01 M Tris-HCl, 0.001 M EDTA, pH 8.0).

The presence of a DNA sequence in a transformed cell may be detected through the use of polymerase chain reaction (PCR). Using this technique specific fragments of DNA can be amplified and detected following agarose gel electrophoresis. For example, 20 ng to 1000 ng genomic DNA is added to a reaction mix containing 10 mM Tris-HCl pH 8.3, 1.5 mM $MgCl_2$, 50 mM KCl, 0.1 mg/ml gelatin, 200 µM each dATP, dCTP, dGTP, dTTP, 0.5 µM each forward and reverse DNA primers, 20% glycerol, and 2.5 units Taq DNA polymerase. The reaction is run in a thermal cycling machine as follows: 3 minutes at 94° C., 39 repeats of the cycle 1 minute at 94° C., 1 minute at 50° C., 30 seconds at 72° C., followed by 5 minutes at 72° C. Twenty µl of each reaction mix is run on a 3.5% NuSieve gel in TBE buffer (90 mM Tris-borate, 2 mM EDTA) at 50V for two to four hours. Using this procedure, for example, one may detect the presence of the uidA gene. Primers for any of the components in any of the transformation-ready circular molecules can be readily prepared by one of skill in the art.

A method to detect the presence of phosphinothricin acetyl transferase (PAT) involves the use of an in vitro enzyme reaction followed by thin layer chromatography, as described in U.S. Pat. No. 5,990,890 (specifically incorporated herein by reference in its entirety). The procedure is conducted by preparing various protein extracts from homogenates of potentially transformed cells, and from control cells that have neither been transformed nor exposed to bialaphos selection, and then assaying by incubation with PPT and $^{14}$C-Acetyl Coenzyme A followed by thin layer chromatography. The results of this assay provide confirmation of the expression of the bar gene which codes for phosphinothricin acetyl transferase (PAT).

For Southern blot analysis genomic DNA is digested with a 3-fold excess of restriction enzymes, electrophoresed through 0.8% agarose (FMC), and transferred (Southern, 1975) to Nytran using 10×SCP (20×SCP: 2 M NaCl, 0.6 M disodium phosphate, 0.02 M disodium EDTA). Probes are labeled with $^{32}$P using the random priming method (Boehringer Mannheim) and purified using Quik-Sep® spin columns (Isolab Inc., Akron, Ohio). Filters are prehybridized at 65° C. in 6×SCP, 10% dextran sulfate, 2% sarcosine, and 500 µg/ml heparin (Chomet et al., 1987) for 15 min. Filters then are hybridized overnight at 65° C. in 6×SCP containing 100 µg/ml denatured salmon sperm DNA and $^{32}$P-labeled probe. Filters are washed in 2×SCP, 1% SDS at 65° C. for 30 min. and visualized by autoradiography using Kodak XAR5 film. For rehybridization, the filters are boiled for 10 min. in distilled $H_2O$ to remove the first probe and then prehybridized as described above.

One of skill in the art would realize that the above methods are general in nature and many variants of these methods may be employed to generate identical or similar results suitable for use with the practice of this invention.

EXAMPLE 13

Utilization of Transgenic Crops

The ultimate goal in plant transformation is to produce plants which are useful to man. In this respect, transgenic plants created in accordance with the current invention may be used for virtually any purpose deemed of value to the grower or to the consumer. For example, one may wish to harvest seed from transgenic plants. This seed may in turn be used for a wide variety of purposes. The seed may be sold to farmers for planting in the field or may be directly used as food, either for animals or humans. Alternatively, products may be made from the seed itself Examples of products which may be made from the seed include, oil, starch, animal or human food, pharmaceuticals, and various industrial products. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, also is used extensively as livestock feed, primarily for beef cattle, dairy cattle, hogs, and poultry. Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize also are used in industry, for example, stalks and husks are made into paper and wallboard and cobs are used for fuel and to make charcoal. Other means for utilizing plants, such as those that may be made with the current invention, have been well known since the dawn of agriculture and will be known to those of skill in the art in light of the instant disclosure. Specific methods for crop utilization may be found in, for example, Sprague and Dudley (1988), and Watson and Ramstad (1987).

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 4,959,317
U.S. Pat. No. 5,015,580
U.S. Pat. No. 5,134,074
U.S. Pat. No. 5,168,053
U.S. Pat. No. 5,188,642
U.S. Pat. No. 5,254,801
U.S. Pat. No. 5,268,526
U.S. Pat. No. 5,302,523
U.S. Pat. No. 5,322,783
U.S. Pat. No. 5,354,855
U.S. Pat. No. 5,384,253
U.S. Pat. No. 5,464,765
U.S. Pat. No. 5,489,520
U.S. Pat. No. 5,500,365
U.S. Pat. No. 5,508,184
U.S. Pat. No. 5,508,468
U.S. Pat. No. 5,510,471
U.S. Pat. No. 5,527,695
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,563,324
U.S. Pat. No. 5,591,616
U.S. Pat. No. 5,610,042
U.S. Pat. No. 5,624,824
U.S. Pat. No. 5,625,047
U.S. Pat. No. 5,627,061
U.S. Pat. No. 5,633,448
U.S. Pat. No. 5,641,876
U.S. Pat. No. 5,658,772
U.S. Pat. No. 5,689,052
U.S. Pat. No. 5,728,925
U.S. Pat. No. 5,780,708
U.S. Pat. No. 5,780,709
U.S. Pat. No. 5,831,011
U.S. Pat. No. 5,929,301
U.S. Pat. No. 5,990,890
U.S. Pat. No. 6,040,497
U.S. Pat. No. 6,153,811
U.S. Pat. No. 6,175,058
U.S. Pat. No. 6,187,994
U.S. Pat. No. 6,262,341
EP 0 154 204
EP 1 035 208
PCT Publication WO 92/17598
PCT Publication WO 95/06128
PCT Publication WO 96/04392
PCT Publication WO 97/04103
PCT Publication WO 97/26366
PCT Publication WO 97/41228
PCT Publication WO 98/26064
PCT Publication WO 99/58659
PCT Publication WO 99/60129
PCT Publication WO 00/70066
PCT Publication WO 00/70067
PCT Publication WO 01/11058
PCT Publication WO 01/21768
PCT Publication WO 01/29241
PCT Publication WO 01/40492

Abdullah et al., *Biotechnology*, 4:1087, 1986.
Abel et al., *Science*, 232:738–743, 1986.
Abremski et al., *Cell*, 32:1301–1311, 1983.
Albert et al., *Plant J.*, 7(4):649–659, 1995.
Araki et al., *J. Mol. Biol.* 225(1):25–37, 1992.
Araki et al., *Nuc. Acids Res.*, 25(4):868–872, 1997.
Armstrong et al., *Maize Genetics Coop Newsletter*, 65:92–93, 1991.
Ausubel et al., Current Protocols in Molecular Biology, pub. John Wiley & Sons, Inc., 1987, including updates to Winter 2001.
Barkai-Golan et al., *Arch. Microbiol.*, 116:119–124, 1978.
Bates, *Mol. Biotechnol.*, 2(2):135–145, 1994.
Battraw and Hall, *Theor. App. Genet.*, 82(2):161–168, 1991.
Bellus, *J. Macromol. Sci. Pure Appl. Chem.*, 1(1):1355–1376, 1994.
Bernal-Lugo and Leopold, *Plant Physiol.*, 98:1207–1210, 1992.
Berzal-Herranz et al., *Genes and Devel.*, 6:129–134, 1992.
Bevan et al., *Nuc. Acids Res.*, 11(2):369–385, 1983.
Bhattacharjee et al., *J. Plant Bioch. and Biotech.* 6, (2): 69–73. 1997.
Blackman et al., *Plant Physiol.*, 100:225–230, 1992.
Bol et al., *Annu. Rev. Phytopath.*, 28:113–138, 1990.
Bottjer et al., *Experimental Parasitology*, 60:239–244, 1985.
Bouchez et al., *EMBO Journal*, 8(13):4197–4204, 1989.
Bower et al., *The Plant Journal*, 2:409–416. 1992.
Bowler et al., *Ann Rev. Plant Physiol.*, 43:83–116, 1992.
Branson and Guss, *Proceedings North Central Branch Entomological Society of America*, 27:91–95, 1972.
Broakaert et al., *Science*, 245:1100–1102, 1989.
Buchanan-Wollaston et al., *Plant Cell Reports*, 11:627–631, 1992.
Buising and Benbow, *Mol Gen Genet*, 243(1):71–81. 1994.
Callis et al., *Genes Dev.*, 1:1183–1200, 1987.
Campbell (ed.), In: Avermectin and Abamectin, 1989.
Capaldi et al., *Biochem. Biophys. Res. Comm.*, 74(2):425–433, 1977.
Casa et al., *Proc. Nat'l Acad. Sci. USA*, 90(23):11212–11216, 1993.
Cech et al., *Cell*, 27:487–496, 1981.
Chau et al., *Science*, 244:174–181, 1989.
Chen and Wu, *Gene*, 185:195–199, 1997.
Cheng et al., *Proc. Nat. Acad. Sci. USA*, 91:5695–5699, 1994.
Choi et al., *Nuc. Acids Res.*, 28(7):e19, 2000.
Chomet et al., *EMBO J.*, 6:295–302, 1987.
Chowrira et al., *J. Biol. Chem.*, 268:19458–62, 1993.
Chowrira et al., *J. Biol. Chem.*, 269:25856–25864, 1994.
Christou et al., *Proc. Nat'l Acad. Sci. USA*, 84(12):3962–3966, 1987.
Chu et al., *Scientia Sinica*, 18:659–668, 1975.
Cline et al., *Nuc. Acids Res.* 24(18):3546–3551, 1996.
Coe et al., In: Corn and Corn Improvement, 81–258, 1988.
Comai et al., *Nature*, 317:741–744, 1985.
Cox, *Proc. Nat. Acad. Sci. USA*, 80:4223–4227, 1983.
Coxson et al., *Biotropica*, 24:121–133, 1992.
Craig, *Ann. Rev. Genetics*, 22:77–105, 1988.
Cuozzo et al., *Bio/Technology*, 6:549–553, 1988.
Cutler et al., *J. Plant Physiol.*, 135:351–354, 1989.
Czapla and Lang, *J. Econ. Entomol.*, 83:2480–2485, 1990.

Dale and Ow, *Proc. Natl. Acad. Sci. USA*, 88:10558–10562, 1991.
Davies et al., *Plant Physiol.*, 93:588–595, 1990.
Day et al., *Genes & Dev.*, 14:2869–2880, 2000.
De Block et al., *The EMBO Journal*, 6(9):25 13–2518, 1987.
De Block et al., *Plant Physiol.*, 91:694–701, 1989.
Dellaporta et al., In: Chromosome Structure and Function: Impact of New Concepts, 18th Stadler Genetics Symposium, 11:263–282, 1988.
Dennis et al., *Nucl. Acids Res.*, 12(9):3983–4000, 1984.
Depicker et al., *Plant Cell Reports*, 7:63–66, 1988.
Dhaese et al., *EMBO Journal*, 2(3):419–426, 1983.
D'Halluin et al., *Plant Cell*, 4(12):1495–1505, 1992.
Dure et al., *Plant Mol. Biol.*, 12:475–486, 1989.
Eckert and Kunkel, *PCR Methods and Applications*, 1:17–24, 1991.
Ellis et al., *EMBO Journal*, 6(11):3203–3208, 1987.
Enomoto, et al., *J. Bacteriol.*, 156(2):663–668, 1983.
Ehrenshaft et al., *Current Genetics*, 34(6):478–485, 1999.
Fang et al., *J. Virological Meth.*, 76(1–2):139–148, 1998.
Feinberg and Vogelstein, *Anal. Biochem.*, 132:6–13, 1983.
Finkle et al., *Plant Sci.*, 42:133–140, 1985.
Erdmann et al., *Mol. Jour. Gen. Micro.*, 138:363–368, 1992.
Fitzpatrick, *Gen. Engineering News*, 22:7, 1993.
Forster and Symons, *Cell*, 49:211–220, 1987.
Fransz et al., *Plant Cell Reports*, 8:67–70, 1989.
Fromm et al., *Nature* 319:791–793, 1986.
Fukushige and Sauer, *Proc. Nat. Acad. Sci. USA*, 89:7905–7909, 1992.
Futcher, *Yeast*, 4(1):27–40, 1988.
Gal et al., *EMBO J.*, 10:1571–1578, 1991.
Gatehouse et al., *J. Sci. Food. Agric.*, 35:373–380, 1984.
Gelvin et al., In: Plant Molecular Biology Manual, 1990.
Gerlach et al., *Nature* 328:802–805, 1987.
Gietz and Woods, *BioTechniques*, 30(4):816–831, 2001.
Golic, *Genetics*, 137:551–563, 1994.
Golic and Lindquist, *Cell*, 59:499–509, 1989.
Goring et al., *Proc. Natl. Acad. Sci. USA*, 88:1770–1774, 1991.
Ghosh-Biswas et al., *J. Biotechnol.*, 32(1):1–10, 1994.
Graham et al., *Mol. Cell. Biol.*, 2:1044–1051, 1986.
Guerrero et al., *Plant Mol. Biol.*, 15:11–26, 1990.
Gupta et al., *Proc. Natl. Acad. Sci. USA*, 90:1629–1633, 1993.
Hagio et al., *Plant Cell Rep.*, 10(5):260–264, 1991.
Hammock et al., *Nature*, 344:458–461, 1990.
Haseloff et al., *Proc. Natl. Acad. Sci. USA*, 94(6):2122–2127, 1997.
Haseloff and Gerlach, *Nature*, 334:585–591, 1988.
He et al., *Plant Cell Reports*, 14 (2–3): 192–196, 1994.
Hemenway et al., *The EMBO J.*, 7:1273–1280, 1988.
Hensgens et al., *Plant Mol. Biol.*, 22(6):1101–1127, 1993.
Hilder et al., *Nature*, 330:160–163, 1987.
Hinchee et al., *Bio/technol.*, 6:915–922, 1988.
Hoess et al., *Proc. Natl. Acad. Sci. USA*, 79:3398–3402, 1982.
Hoess et al., *Nuc. Acids Res.*, 14:2287–2300, 1986.
Holmberg et al., *Nature Biotechnology*, 15(3):244–247, 1997.
Hou and Lin, *Plant Physiology*, 111(2 Supp.): 166, 1996.
Huang et al., *Nuc. Acids Res.*, 19(3):443–448, 1991.
Huang et al., *J. of Bacteriology*, 179(19):6076–6083, 1997.
Ikeda et al., *J. Bacteriol.*, 169:5615–5621, 1987.
Ikuta et al., *Bio/technol.*, 8:241–242, 1990.
Ito et al., *Nuc. Acid Res.*, 10: 1755, 1982.
Jefferson et al., *Proc. Natl. Acad. Sci. USA*, 83(22):8447–8451, 1986.
Jefferson, *Plant Mol. Biol. Rep.*, 5:387–405, 1987.
Jelesko et al., *Proc. Natl. Acad. Sci. USA*, 96:10302–10307, 1999.
Johnson et al., *Proc. Natl. Acad. Sci. USA*, 86:9871–9875, 1989.
Joshi, *Nucleic Acids Res.*, 15:6643–6653, 1987.
Joyce, *Nature*, 338:217–244, 1989.
Kaasen et al., *J. Bacteriology*, 174:889–898, 1992.
Kaeppler et al., *Plant Cell Reports* 9: 415–418, 1990.
Kaeppler et al., *Theor. Appl. Genet.*, 84(5–6):560–566, 1992.
Karsten et al., *Botanica Marina*, 35:11–19, 1992.
Katz et al., *J. Gen. Microbiol.*, 129:2703–2714, 1983.
Keller et al., *EMBO J.*, 8(5):1309–1314, 1989.
Kim and Cech, *Proc. Natl. Acad. Sci. USA*, 84:8788–8792, 1987.
Klee et al., *Mol. Gen. Genet.*, 210(3):437–442, 1987.
Knittel et al., *Plant Cell Reports*, 14(2–3):81–86, 1994.
Kohler et al., *Plant Mol. Biol.*, 29(6): 1293–1298, 1995.
Koster and Leopold, *Plant Physiol.*, 88:829–832, 1988.
Lazzeri, *Methods Mol. Biol.*, 49:95–106, 1995.
Lee et al., *Korean J. Genet.*, 1 1(2):65–72, 1989.
Lee and Saier, *J. of Bacteriol.*, 153(2):685–692, 1983.
Lee and Saito, *Gene*, 216:55–65, 1988.
Levings, *Science*, 250:942–947, 1990.
Lieber and Strauss, *Mol. Cell. Biol.*, 15: 540–551, 1995.
Lindberg and Andersson, *J. Virological Meth.*, 77(2): 131–137, 1999.
Loomis et al., *J. Expt. Zoology*, 252:9–15, 1989.
Lorz et al., *Mol. Gen Genet*, 199:178–182, 1985.
Lundberg et al., *Gene*, 108:1–6, 1991.
Lyznik et al., *Nuc. Acids Res.*, 24(19):3784–3789, 1996.
Ma et al., *Nature*, 334:631–633, 1988.
Maeser et al., *Mol. Gen. Genet.*, 230(1–2): 170–176, 1991.
Marcotte et al., *Nature*, 335:454–457, 1988.
Mariani et al., *Nature*, 347:737–741, 1990.
Martinez et al., *J. Mol. Biol.*, 208(4):551–565, 1989.
Matilla et al., *Nuc. Acids Res.*,19(18):4967–4973, 1991.
McElroy et al., *Plant Cell*, 2:163–171, 1990.
McCabe and Martinell, *Bio-Technology*, 11(5):596–598, 1993.
Medberry et al., *Nuc. Acids Res.*, 23(3):485–490, 1995.
Meyer-Leon et al., *Cold Spring Harb Symp Quant Biol.*, 49:797–804, 1984.
Michel and Westhof, *J. Mol. Biol.*, 216:585–610, 1990.
Mundy and Chua, *The EMBO J.*, 7:2279–2286, 1988.
Murakami et al., *Mol. Gen. Genet.*, 205:42–50, 1986.
Murdock et al., *Phytochemistry*, 29:85–89, 1990.
Murashige and Skoog, *Physiol. Plant.*, 15:473–497, 1962.
Nagatani et al., *Biotech. Tech.*, 11(7):471–473, 1997.
Napoli et al., *Plant Cell*, 2:279–289, 1990.
Odell et al., *Nature*, 313:810–812, 1985.
Ogawa et al., *Sci. Rep.*, 13:42–48, 1973.
Ogilvie et al., *Science*, 214:270, 1981.
O'Gorman et al., *Science*, 251:1351–1355, 1991.
Ohler and Rose, *PCR Methods and Applications*, 2:51–59, 1992.
Omirulleh et al., *Plant Mol. Biol.*, 21(3):415–428, 1993.
Onouchi et al., *Nuc. Acids Res.*, 19:6373–6378, 1991.
Ow, *Curr. Op. Biotech.*, 7:181–186, 1996.
Ow et al., *Science*, 234:856–859, 1986.
Paszkowski et al., *EMBO J.*, 3:2717–2722, 1984.
Palukaitis et al., *Virology*, 99:145–151, 1979.
Pearce et al., *Science*, 253:895–898, 1991.
Perlak et al., *Proc. Natl. Acad. Sci. USA*, 88:3324–3328, 1991.
Perriman et al., *Gene*, 113:157–163, 1992.
Peterhans et al., *EMBO J.*, 9(11):3437–3445, 1990.

Phi-Van et al., *Mol. Cell. Biol.*, 10:2302–2307, 1990.
Piatkowski et al., *Plant Physiol.*, 94:1682–1688, 1990.
Potrykus et al., *Mol. Gen. Genet.*, 199:183–188, 1985.
Prasher et al., *Biochem. Biophys. Res. Commun.*, 126(3): 1259–1268, 1985.
Prody et al., *Science*, 231:1577–1580, 1986.
Quigley et al., *J. Mol. Evol.*, 29(5):412–421, 1989.
Raymond et al., *BioTechniques*, 27:892–894, 1999.
Reed et al., *J. Gen. Microbiology*, 130:1–4, 1984.
Reichel et al., *Proc. Natl. Acad. Sci. USA*, 93(12):5888–5893, 1996.
Reinhold-Hurek and Shub, *Nature*, 357:173–176, 1992.
Rensburg et al., *J. Plant Physiol.*, 141:188–194, 1993.
Rhodes et al., *Methods Mol. Biol.*, 55:121–131, 1995.
Ritala et al., *Plant Mol. Biol.*, 24(2):317–325, 1994.
Rychlik et al., *Nuc. Acids Res.* 18(21):6409–6412, 1990.
Sadowski, *Progress in Nuc. Acid Res. and Mol. Biol.*, 51:53–91, 1995.
Sambrook and Russell in *Molecular Cloning: A Laboratory Manual*, Third Edition, Cold Spring Harbor Laboratory, Cold Spring Harbor, N.Y., 2001.
Sarkar et al., *PCR Methods Appl.*, 2:318–322, 1993.
Sauer, *Mol. Cell Biol.*, 7(6):2087–2096,1987.
Sauer, *Methods*, 14:381–392, 1998.
Sauer, *Curr. Op. Biotech.*, 5:521–527, 1994.
Sauer and Henderson, *Proc. Natl. Acad. Sci. USA.*, 85(14): 5166–5170, 1988.
Senecoff et al., *J. Mol. Biol.*, 201:405–421, 1988.
Shagan and Bar-Zvi, *Plant Physiol.*, 101: 1397–1398, 1993.
Shapiro, In: *Mobile Genetic Elements*, 1983
Sheen et al., *Plant Journal*, 8(5):777–784, 1995.
Shure et al., *Cell*, 35:225–233, 1983.
Singsit et al., *Transgenic Res.*, 6(2):169–176, 1997.
Smith et al., *Mol. Gen. Genet.*, 224:447–481, 1990.
Southern, *J. Mol. Biol.*, 98:503–517, 1975.
Spencer et al., *Plant Molecular Biology*, 18:201–210, 1992.
Sprague and Dudley, eds., *Corn and Improvement*, 3rd ed, 1988.
Stalker et al., *Science*, 242:419–422, 1988.
Sternberg et al., *J. Mol. Biol.*, 187:197–212, 1986.
Stief et al., *Nature* 341:343–345, 1989.
Stiefel et al., *Plant Cell*, 2(8):785–793, 1990.
Sutcliffe, *Proc. Natl. Acad. Sci. USA*, 75:3737–3741, 1978.
Swoboda et al., *Mol. Gen. Gen.*, 237:33–40, 1993.
Swoboda et al., *EMBO J.*, 13:484–489, 1994.
Symons, *Nucl. Acids Res.*, 9(23):6527–6537, 1981.
Symons, *Annu. Rev. Biochem.*, 61:641–671, 1992.
Szostak et al., *Cell*, 33:25–35, 1983.
Takita et al., *Yeast*, 13:763–768, 1997.
Tanksley et al., *Bio/Technology*, 7:257–264, 1989.
Tarczynski et al., *Proc. Natl. Acad. Sci. USA*, 89:1–5, 1992.
Tarczynski et al., *Science*, 259:508–510, 1993.
Thillet et al., *J. Biol. Chem.*, 263:12500–12508, 1988.
Thompson et al., *The EMBO Journal*, 6(9):2519–2523, 1987.
Thompson et al., *Euphytica*, 85(1–3):75–80, 1995.
Tian et al., *Plant Cell Rep.*, 16:267–271, 1997.
Timmermans et al., *J. Biotechnol.*, 14:333–344, 1990.
Tomes et al., *Plant. Mol. Biol.* 14(2):261–268, 1990.
Torbet et al., *Crop Science*, 38(1):226–23 1, 1998.
Torbet et al., *Plant Cell Reports*, 14(10):635–640, 1995.
Toriyama et al., *Theor Appl. Genet.*, 73:16, 1986.
Trinh and Morrison, *J. Immunological Methods*, 244:185–193, 2000.
Tsukada et al., *Plant Cell Physiol.*, 30(4):599–604, 1989.
Tyagi and Kramer, *Nature Biotech.*, 14:303–308, 1996.
Uchimiya et al., *Mol. Gen. Genet.*, 204:204–207, 1986.
Van der Krol et al., *Plant Cell*, 2:291–299, 1990.
Van Eck et al., *Plant Cell Reports*, 14(5):299–304, 1995.
Vasil et al., *Plant Physiol.*, 91:1575–1579, 1989.
Vernon and Bohnert, *The EMBO J.*, 11:2077–2085, 1992.
Vogel et al., *J. Cell. Biochem.*, (Suppl. 0) 13:Part D, 1989.
Wallace et al., *Nuc. Acids Res.*, 28(6):1455–1464, 2000.
Wang et al., *Molecular and Cellular Biology*, 12(8):3399–3406, 1992.
Watrud et al., In: *Engineered Organisms and the Environment*, 1985.
Watson and Ramstad, eds., *Corn: Chemistry and Technology*, 1987.
Weber et al., *BioTechniques*, 25(3):415–419, 1988.
Withers and King, *Plant Physiol.*, 64:675–678, 1979.
Wolter et al., *The EMBO J.*, 1 1(13):4685–4692, 1992.
Xiang and Guerra, *Plant Physiol.*, 102:287–293, 1993.
Xu et al., *Plant Physiol.*, 110:249–257, 1996.
Yamada et al., *Plant Cell Rep.*, 4:85–88, 1986.
Yamaguchi-Shinozaki et al., *Plant Cell Physiol.*, 33:217–224, 1992.
Yuan and Altman, *Science*, 263:1269–1273, 1994.
Yuan et al., *Proc. Natl. Acad Sci. USA*, 89:8006–8010, 1992.
Zhang et al., *The Plant Cell*, 3:1155–1165, 1991.
Zheng and Edwards, *J. Gen. Virol.*, 71:1865–1868, 1990.
Zhou et al., *Plant Cell Reports*, 12(11):612–616, 1993.
Zubko et al., *Nature Biotech.*, 18:442–445, 2000.
Zukowsky et al., *Proc. Natl. Acad. Sci. USA*, 80:1101–1105, 1983.

What is claimed is:

1. A method of preparing a non-replicating, circular DNA molecule comprising the steps of:
   a) providing a starting non-replicating circular DNA molecule which comprises a lox site-specific recombination sequence, and
   b) producing a non-replicating, circular DNA molecule by amplifying the starting circular DNA molecule in vitro, wherein the amplifying comprises PCR amplification using a first non-mutagenizing oligonucleotide primer with a nucleic acid sequence complementary to a selected sequence of the starting circular DNA molecule.

2. The method of claim 1, wherein the non-replicating, circular DNA molecule has a sequence substantially identical to the starting circular DNA molecule.

3. The method of claim 1, wherein amplifying further comprises using a second non-mutagenizing oligonucleotide primer.

4. The method of claim 1, wherein the lox sequence is selected from the group consisting of SEQ ID NO:1, SEQ ID NO:2, SEQ ID NO:3 and SEQ ID NO:4.

5. A method of preparing a transgenic plant cell comprising:
   a) providing a non-replicating circular DNA molecule produced by the method of claim 1, wherein said DNA molecule comprises a selected DNA sequence;
   b) contacting a plant cell with the non-replicating circular DNA molecule under conditions wherein the plant cell acquires the circular DNA molecule; and
   c) identifying a transgenic plant cell comprising the selected DNA sequence.

6. The method of claim 5, wherein contacting comprises a method selected from the group consisting of microprojectile bombardment, PEG mediated transformation of protoplasts, electroporation, and silicon carbide fiber mediated transformation.

7. The method of claim 5, wherein contacting comprises microprojectile bombardment.

8. The method of claim 5, wherein the genome of the plant cell comprises a lox site-specific recombination sequence.

9. The method of claim 8, wherein the lox sequence is selected from the group consisting of SEQ ID NO:1, SEQ ID NO:2, SEQ ID NO:3 and SEQ ID NO:4.

10. The method of claim 5, wherein the transgenic is plant cell derived from a dicotyledonous plant.

11. The method of claim 10, wherein the dicotyledonous plant is selected from the group consisting of tobacco, tomato, potato, soybean, cotton, canola, alfalfa and sunflower.

12. The method of claim 11, wherein the dicotyledonous plant is soybean.

13. The method of claim 5, wherein the transgenic is plant cell derived from a monocotyledonous plant.

14. The method of claim 13, wherein the monocotyledonous plant is selected from the group consisting of wheat, maize, rye, rice, oat, barley, turfgrass, sorghum, millet and sugarcane.

15. The method of claim 14, wherein the monocotyledonous plant is maize.

16. The method of claim 5, wherein the non-replicating circular DNA molecule comprises a selected DNA sequence encoding a protein conferring a trait selected from the group consisting of insect resistance, bacterial disease resistance, fungal disease resistance, viral disease resistance, nematode disease resistance, herbicide resistance, enhanced grain composition or quality, enhanced nutrient utilization, enhanced environment or stress resistance, reduced mycotoxin contamination, male sterility, a selectable marker phenotype, a screenable marker phenotype, a negative selectable marker phenotype, and altered plant agronomic characteristics.

17. The method of claim 16, wherein the selected DNA sequence encodes a protein imparting a selectable marker phenotype, wherein the protein is selected from the group consisting of phosphinothricin acetyltransferase, glyphosate resistant EPSPS, aminoglycoside phosphotransferase, hygromycin phosphotransferase, neomycin phosphotransferase, dalapon dehalogenase, bromoxynil resistant nitrilase, anthranilate synthase and glyphosate oxidoreductase.

18. A method of preparing a fertile transgenic plant comprising:
   a) providing a non-replicating circular DNA molecule produced by the method of claim 1, wherein said DNA molecule comprises a selected DNA sequence;
   b) contacting a plant cell with the non-replicating circular DNA molecule under conditions wherein the plant cell acquires the circular DNA molecule;
   c) identifying a transgenic plant cell comprising the selected DNA sequence; and
   d) regenerating a fertile transgenic plant comprising said selected DNA sequence.

19. The method of claim 18, wherein contacting comprises a method selected from the group consisting of microprojectile bombardment, PEG mediated transformation of protoplasts, electroporation, and silicon carbide fiber mediated transformation.

20. The method of claim 18, wherein contacting comprises microprojectile bombardment.

21. The method of claim 18, wherein the genome of the plant cell comprises a lox site-specific recombination sequence.

22. The method of claim 21, wherein the lox sequence is selected from the group consisting of SEQ ID NO:1, SEQ ID NO:2, SEQ ID NO:3 and SEQ ID NO:4.

23. The method of claim 18, wherein the fertile transgenic plant is a dicotyledonous plant.

24. The method of claim 23, wherein the fertile transgenic dicotyledonous plant is selected from the group consisting of tobacco, tomato, potato, soybean, cotton, canola, alfalfa and sunflower.

25. The method of claim 24, wherein the fertile transgenic dicotyledonous plant is soybean.

26. The method of claim 18, wherein the fertile transgenic plant is a monocotyledonous plant.

27. The method of claim 26, wherein the fertile transgenic monocotyledonous plant is selected from the group consisting of wheat, maize, rye, rice, oat, barley, turfgrass, sorghum, millet and sugarcane.

28. The method of claim 27, wherein the fertile transgenic monocotyledonous plant is maize.

29. The method of claim 18, further comprising producing progeny of any generation.

30. The method of claim 18, wherein the non-replicating circular DNA molecule comprises a selected DNA sequence encoding a protein conferring a trait selected from the group consisting of insect resistance, bacterial disease resistance, fungal disease resistance, viral disease resistance, nematode disease resistance, herbicide resistance, enhanced grain composition or quality, enhanced nutrient utilization, enhanced environment or stress resistance, reduced mycotoxin contamination, male sterility, a selectable marker phenotype, a screenable marker phenotype, a negative selectable marker phenotype, and altered plant agronomic characteristics.

31. The method of claim 30, wherein the selected DNA sequence encodes a protein imparting a selectable marker phenotype, wherein the protein is selected from the group consisting of phosphinothricin acetyltransferase, glyphosate resistant EPSPS, aminoglycoside phosphotransferase, hygromycin phosphotransferase, neomycin phosphotransferase, dalapon dehalogenase, bromoxynil resistant nitrilase, anthranilate synthase and glyphosate oxidoreductase.

32. A method of preparing a crossed, fertile transgenic plant comprising:
   a) providing a non-replicating circular DNA molecule produced by the method of claim 1, wherein said DNA molecule comprises a selected DNA sequence;
   b) contacting a plant cell with the non-replicating circular DNA molecule under conditions wherein the plant cell acquires the circular DNA molecule;
   c) identifying a transgenic plant cell comprising the selected DNA sequence;
   d) regenerating a fertile transgenic plant comprising said selected DNA sequence; and
   e) crossing said fertile transgenic plant with itself or with a second plant to prepare a seed of a crossed fertile transgenic plant, wherein said seed comprises said selected DNA sequence.

33. The method of claim 32, further comprising producing a crossed fertile transgenic progeny plant of any generation.

34. The method of claim 32, wherein the second plant lacks the selected DNA sequence.

35. The method of claim 32, wherein the plant is a monocotyledonous plant.

36. The method of claim 35, wherein the monocotyledonous plant is selected from the group consisting of wheat, oat, barley, maize, rye, rice, turfgrass, sorghum, millet and sugarcane.

37. The method of claim 36, wherein the monocotyledonous plant is a maize plant.

38. The method of claim 32, wherein the plant is a dicotyledonous plant.

39. The method of claim 38, wherein the dicotyledonous plant is selected from the group consisting of tobacco, tomato, potato, soybean, canola, alfalfa, sunflower and cotton.

40. The method of claim 39, wherein the dicotyledonous plant is a soybean plant.

41. The method of claim 32, wherein the selected DNA sequences encodes a protein selected from the group consisting of a protein imparting insect resistance, bacterial disease resistance, fungal disease resistance, viral disease resistance, nematode disease resistance, herbicide resistance, enhanced grain composition or quality, enhanced nutrient utilization, enhanced environment or stress resistance, reduced mycotoxin contamination, male sterility, a selectable marker phenotype, a screenable marker phenotype, a negative selectable marker phenotype, and altered plant agronomic characteristics.

42. The method of claim 41, wherein the selected DNA sequences encodes a protein imparting a selectable marker phenotype, wherein the protein is selected from the group consisting of phosphinothricin acetyltransferase, glyphosate resistant EPSPS, aminoglycoside phosphotransferase, hygromycin phosphotransferase, neomycin phosphotransferase, dalapon dehalogenase, bromoxynil resistant nitrilase, anthranilate synthase and glyphosate oxidoreductase.

43. The method of claim 42 wherein the selected DNA sequence encodes glyphosate resistant EPSPS.

44. The method of claim 42 wherein the selected sequence comprises Npt II.

45. The method of claim 32, further defined as a progeny plant of any generation of a crossed fertile transgenic plant.

* * * * *

UNITED STATES PATENT AND TRADEMARK OFFICE
CERTIFICATE OF CORRECTION

PATENT NO. : 7,122,715 B2 Page 1 of 1
APPLICATION NO. : 09/957660
DATED : October 17, 2006
INVENTOR(S) : Korte et al.

It is certified that error appears in the above-identified patent and that said Letters Patent is hereby corrected as shown below:

Column 92, line 48, delete "is plant" and insert --is-- therefor.

Column 92, line 56, delete "is plant" and insert --is-- therefor.

Column 94, line 50, delete "sequences" and insert --sequence-- therefor.

Column 94, line 61, delete "sequences" and insert --sequence-- therefor.

Signed and Sealed this

Twenty-seventh Day of February, 2007

JON W. DUDAS
*Director of the United States Patent and Trademark Office*

SEQUENCE LISTING

```
<160> NUMBER OF SEQ ID NOS: 16

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 1
ataacttcgt atagcataca ttatacgaag ttat                                         34
```

```
<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
ataacttcgt atagcataca ttatacgaac ggta                              34

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
taccgttcgt atagcataca ttatacgaag ttat                              34

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
taccgttcgt atagcataca ttatacgaac ggta                              34

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
cggagaacca gcgtgcaatc catcttgttc                                   30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gaacaagatg gattgcacgc tggttctccg                                   30

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
catggcgcaa gttagcagaa tctgcaatgg tg                                32
```

```
<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
caccattgca gattctgcta acttgcgcca tg                                    32

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
catcacgacg gtcatcgagc cgatcatgac g                                     31

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
cgtcatgatc ggctcgatga ccgtcgtgat g                                     31

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
cgcgcggccg cctcgagat                                                   19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
ctcgaggcgg ccgcgcgat                                                   19

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
attccccgga tcgtttcgca tgattgaaca agatgg                                36
```

```
<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
ccatcttgtt caatcatgcg aaacgatccg gggaat                                 36

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
cgatgccacg atgatcgcca cgagcttccc ggag                                   34

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
ctccgggaag ctcgtggcga tcatcgtggc atcg                                   34
```